(12) United States Patent
Takayama et al.

(10) Patent No.: US 11,649,281 B2
(45) Date of Patent: May 16, 2023

(54) ANTIBODY AGAINST HUMAN PROSTAGLANDIN E2 RECEPTOR EP4

(71) Applicant: NB Health Laboratory Co., Ltd., Sapporo (JP)

(72) Inventors: Kiyoshi Takayama, Sapporo (JP); Tomoko Shimizu, Sapporo (JP); Yuji Urushibata, Sapporo (JP); Yukihiko Sugimoto, Kumamoto (JP)

(73) Assignee: NB HEALTH LABORATORY CO., LTD., Hokkaido (JP)

( * ) Notice: Subject to any disclaimer, the term of this patent is extended or adjusted under 35 U.S.C. 154(b) by 732 days.

(21) Appl. No.: 16/555,524

(22) Filed: Aug. 29, 2019

(65) Prior Publication Data

US 2019/0389949 A1 Dec. 26, 2019

Related U.S. Application Data

(62) Division of application No. 14/864,707, filed on Sep. 24, 2015, now Pat. No. 10,435,465, which is a division of application No. 13/876,763, filed as application No. PCT/JP2011/072190 on Sep. 28, 2011, now Pat. No. 9,175,080.

(30) Foreign Application Priority Data

Sep. 29, 2010 (JP) ................. 2010-218158

(51) Int. Cl.
*C07K 16/28* (2006.01)
*C07K 17/00* (2006.01)
*G01N 33/88* (2006.01)

(52) U.S. Cl.
CPC .......... *C07K 16/28* (2013.01); *C07K 16/2869* (2013.01); *C07K 17/00* (2013.01); *G01N 33/88* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| 6,911,531 | B2 | 6/2005 | Regan et al. |
| 2004/0210040 | A1 | 10/2004 | Landolfi et al. |
| 2010/0040537 | A1 | 2/2010 | Gu et al. |

FOREIGN PATENT DOCUMENTS

| EP | 2 322 220 A1 | 5/2011 |
| JP | 3118460 B2 | 12/2000 |
| SE | 9202892 | 2/1992 |
| WO | 94/07920 A1 | 4/1994 |
| WO | 95/06664 A1 | 3/1995 |
| WO | 03/099857 A1 | 12/2003 |
| WO | 2004/073589 A2 | 9/2004 |
| WO | 2010/013498 A1 | 2/2010 |

OTHER PUBLICATIONS

Wu, Nie, Huse, and Watkins. Humanization of a murine monoclonal antibody by simultaneous optimization of framework and CDR residues. Journal of Molecular Biology, 1999. vol. 294, pp. 151-162.*
Skolnick and Fetrow. From genes to protein structure and function: novel applications of computational approaches in the genomic era. Trends in Biotechnology, 2000. vol. 18, pp. 34-39.*
Paul (1993) Fundamental Immunology, #rd edition, pp. 292-295.*
Bendig (1995) Methods: a companion. Methods in Enzymology 8: 83-93.*
MacCallum et al. (1996) J. Mol. Biol. 262: 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Fortier, I. et al., "Immunolocalization of the prostaglandin E2 receptor subtypes in human bone tissue: differences in foetal, adult normal, osteoporotic and pagetic bone", Prostaglandins, Leukotrienes and Essential Fatty Acids, 2004, pp. 431-439, vol. 70; cited in ISR and Japanese Office Action dated Jan. 15, 2013.
Biswas, Sumana et al., "Prostaglandin E2 receptor subtypes, EP1, EP2, EP3 and EP4 in human and mouse ocular tissues—a comparative immunohistochemical study", Prostaglandins, Leukotrienes and Essential Fatty Acids, 2004, pp. 277-288, vol. 71; cited in ISR and Japanese Office Action dated Jan. 15, 2013.
Stillman, Brett A. et al., "A conserved threonine in the second extracellular loop of the human EP2 and EP4 receptors is required for ligand binding", European Journal of Pharmacology, 1998, pp. 73-82, vol. 357; cited in ISR and Japanese Office Action dated Jan. 15, 2013.
Fedyk, Eric R. et al., "Prostaglandin E2 receptors of the EP2 and EP4 subtypes regulate activation and differentiation of mouse B lymphocytes to IgE-secreting cells", Proc. Natl. Acad. Sci. USA, Oct. 1996, pp. 10978-10983, vol. 93; cited in ISR and Japanese Office Action dated Jan. 15, 2013.
Takita, Morichika et al., "Prostaglandin E receptor EP4 antagonist suppresses osteolysis due to bone metastasis of mouse malignant melanoma cells", FEBS Letters, 2007, pp. 565-571, vol. 581; cited in ISR and Japanese Office Action dated Jan. 15, 2013.
Martinet, Ludovic et al., "PGE2 inhibits natural killer and gd T cell cytotoxicity triggered by NKR and TCR through a cAMP-mediated PKA type I-dependent signaling", Biochemical Pharmacology, 2010, pp. 838-845, vol. 80; cited in specification.

(Continued)

*Primary Examiner* — Michael D Pak
(74) *Attorney, Agent, or Firm* — Wenderoth, Lind & Ponack, L.L.P.

(57) ABSTRACT

It is an object of the present invention to provide an antibody that binds to a human $PGE_2$ receptor subtype EP4 and inhibits the function of EP4, or a functional fragment thereof. It is another object of the present invention to provide a medicament comprising the aforementioned antibody or a functional fragment thereof. Mice were immunized with the human $PGE_2$ receptor subtype EP4, and a monoclonal antibody that suppresses the intracellular cAMP level increase induced by EP4 was screened. In addition, the CDR sequences of the obtained monoclonal antibody were determined.

9 Claims, 9 Drawing Sheets

Specification includes a Sequence Listing.

(56) References Cited

OTHER PUBLICATIONS

Sharma, Som D. et al., "Proanthocyanidins Inhibit In vitro and In vivo Growth of Human Non-Small Cell Lung Cancer Cells by Inhibiting the Prostaglandin E2 and Prostaglandin E2 Receptors", Molecular Cancer Therapeutics, 2010, pp. 569-580, vol. 9; cited in specification.
Sharma, Sherven et al., "Tumor Cyclooxygenase-2/Prostaglandin E2-Dependent Promotion of FOXP3 Expression and CD4+CD25+ T Regulatory Cell Activities in Lung Cancer", Cancer Research, 2005, pp. 5211-5220, vol. 65; cited in specification.
Sugimoto, Yukihiko et al., "Prostaglandin E Receptors", Journal of Biological Chemistry, 2007, pp. 11613-11617, vol. 282; cited in specification.
Yao, Chengcan et al., "Prostaglandin E2-EP4 signaling promotes immune inflammation through TH1 cell differentiation and TH17 cell expansion", Nature Medicine, 2009, pp. 633-640, vol. 15; cited in specification.
Japanese Office Action dated Jan. 15, 2013, issued in Japanese Patent Application No. 2012-536508. (6 Pages).
International Search Report of PCT/JP2011/072190, dated Oct. 25, 2011. (13 pages).
Lin, Chung-Ren et al., "Prostaglandin E2 Receptor EP4 Contributes to Inflammatory Pain Hypersensitivity", The Journal of Pharmacology and Experimental Therapeutics, 2006, pp. 1096-1103, vol. 319 No. 3; cited in specification, ISR, and Japanese Office Action dated Jan. 15, 2013.
Popp, Laura et al., "Comparison of nociceptive behavior in prostaglandin E, F, D, prostacyclin and thromboxanse receptor knockout mice", European Journal of Pain, 2009, pp. 691-703, vol. 13; cited in specification.
Robertson, Fredika et al., "Differenlial Regulation of the Aggressive Phenotype of lnflammtory Breast Cancer Cells by Prostanoid Receptors EP3 and EP4", Cancer, 2010, pp. 2806-2814, vol. 116; cited in specification.
Sakata, Daiji et al., "Prostaglandin E2, an Immunoactivator", Journal of Pharmacological Sciences, 2010, pp. 1-5, vol. 112; cited in specification.
GENcompare, "Prostaglandin E Receptor (EP1, EP2. EPa, and EP4) Antibodies", Web URL: http://www.gencompare.com/prostaglandin_e_receptor_%28ep1,_ep2,_ep3,_and_ep4%29.htm, published on Apr. 1, 2002 (3 pages); cited in Office Action dated in Jul. 31, 2013.
Office Action dated Jul. 31, 2013, issued in New Zealand Patent Application No. 609887.
Extended European Search Repon dated Oct. 10, 2013, in European Application No. 11829187.1. (9 pages).
K. G. Halvorson et al.; "A Blocking Antibody to Nerve Growth Factor Attenuates Skeletal Pain Induced by Prostate Tumor Cells Growing in Bone", Cancer Research, (pp. 9435-04356) cited in EESR dated Oct. 10, 2013.
European examination report(Communication pursuant to Article 94(3) EPC) dated May 19, 2014, issued in corresponding European Patent Application No. 11829187.1 (9 pages).
L. B. A. Van De Putte et al., "Efficacy and safety of the fully human anti-tumour necrosis factor a monoclonal antibody adalimumab (D2E7) in DMARD refractory patients with rheumatoid arthritis: a 12 week, phase II study";—Ann Rheum Dis 2003, vol. 62, pp. 1168-1110, cited in the European Examination Report dated May 19, 2014 and the Extended European Search Report dated Oct. 10, 2014, which was previously submitted in the IDS on Nov. 27, 2013.
B. Kashiwagi et al., "Positive Effect of Prostaglandin on Regulation of Prostatic Blood Flow", Urology, vol. 68, No. 3, pp. 682-686, Sep. 1, 2006, cited in the European Examination Report dated May 19, 2014 and the Extended European Search Report dated Oct. 10, 2014.
Chinese Office Action dated May 30, 2014, issued in Chinese Patent Application No. 201180046998.3 (8 pages).
English translation of Chinese Office Action dated May 30, 2014, issued in Chinese Patent Application No. 201180046998.3 (8 pages).
Schneider, J. et al., "Production of the amino acids L-glutamate, L-lysine, L-ornithine and L-arginine from arabinose by recombinant Corynebacterium glutamicum", Journal of Biotechnology, 2011, pp. 191-198; cited in Indian Examination Report.
Examination Report dated Mar. 23, 2018, issued in Indian Patent Application No. 766/MIMNP/2013 related to counterpart U.S. Appl. No. 13/876,763, with English translation. (7 pages).
Paul, W.E. Fundamental Immunology, 3rd edition, pp. 292-295 (1993).
Bendig, M.M. Humanizalion of Rodent monoclonal anitbodies by CDR grafting. Methods: A Companion to Methods in Enzymology, 1995; vol. 8, p. 83-93.
MacCallum R.M. et al, Antibody-antigen Interactions: Contract analysis and binding site topography. J. Mpl. Biol., 1998 vol. 262: p. 732-745.
Vajdos, Adams, Breece, Presta, De Vos, and Sidhu. Comprehensive functional maps of the antigen-binding site of an anti-ErBb2 antibody obtained with Shotgun scanning mutagenesis. Journal of Molecular Biology, 2002. vol. 20, pp. 415-428.
Casset, F.et al. A peptide mimetic of an anti-CD4 monoclonal antibody by rational design. Biochemical and Biophysical Research Communications, 2003. vol. 307, pp. 198-205.
Wu, Nie, Huse, and Watkins. Humanizalion of a murine monoclonal anitbody by simultaneous optimization of framework and CDR residues. Journal of Molecular Biology, 1999. vol. 294, pp. 151-162.
R. Morath et al.; Immunolocalization of the Four Prostaglandin E2 Receptor Proteins EP1, EP2, EP3, and EP4 in Human Kidney, J Am Soc, vol. 10, pp. 1851-1860, 1999, cited in EESR dated Oct. 10, 2013.
Cayman Chemical, "EP4 Recepton (N-term) Polyclonal Antiserum"; Product Information item #101770, Oct. 10, 2011, cited in EESR dated Oct. 10, 2013. (1 page).
Cayman Chemical, "EPA Receptor (C-Term) Polyclonal Antiserum"; item #10175, May 28, 2013, cited in EESR dated Oct. 10, 20136. (1 page).
Stillman, Brett A. et al., "A conserved threonine in the second extracellular loop of the human EP2 and EP4 Yeceptors is required for ligand binding", European Journal of Pharmacology, 1998, pp. 73-82, vol. 357; cited in ISR and Japanese Office Action dated Jan. 15, 2013.
Martinet, Ludovic et al., "PGE2 inhibits natural killer and gd T cell cytotoxicity triggered by NKR and TCR through a cAMP-mediated PKA type l-dependent signaling", Biochemical Pharmacology, 2010, pp. 838-845, vol. 80; cited in specification.
Sharma, Som D. et al., "Proanthocyanidins Inhibit In vitro and In vivo Growth of Human Non-Small Cell Lung Cancer Dells by Inhibiting the Prostaglandin E2 and Prostaglandin E2 Receptors", Molecular Cancer Therapeutics, 2010, pp. 569-580, vol. 9; cited in specification.
Sharma, Sherven et al., "Tumor Cyclooxygenase-2/Prostaglandin E2-Dependent Promotion of FOXP3 Expression and CD4 +CD25+ T Regulatory Cell Activities in Lung Cancer", Cancer Research, 2005, pp. 5211-5220, vol. 65; cited n specification.
Yao, Chengcan et al., "Prostaglandin E2-EP4 signaling promotes immune inflammation through TH1 cell iifferentiation and TH17 cell expansion". Nature Medicine, 2009, pp. 633-640, vol. 15; cited in specification.
Popp, Laura et al., "Comparison of nociceptive behavior in prostaglandin E, F, D, prostacyclin and thromboxanse Yeceptor knockout mice", European Journal of Pain, 2009, pp. 691-703, vol. 13; cited in specification.
Robertson, Fredika et al., "Differential Regulation of the Aggressive Phenotype of Inflammtory Breast Cancer Cells ay Prostanoid Receptors EP3 and EP4", Cancer, 2010, pp. 2806-2814, vol. 116; cited in specification.
Sakata, Daiji et al., "Prostaglandin E2, an Immunoactivator", Journal of Pharmocological Sciences, 2010, pp. 1-5, vol. 112; cited in specification.
Gencompare, "Prostaglandin E Receptor (EP1, EP2, EP3, and EP4) Antibodies", Web URL: http://www.gencompare.com/prostaglandin_e_receptor_%28ep1,_ep2,_ep3,_and_ep4%29.htm, published on Apr. 1, 2002 (3 pages); cited in Office Action dated in Jul. 31, 2013.

(56) References Cited

OTHER PUBLICATIONS

Office Action dated in Jul. 31, 2013, issued in New Zealand Patent Application No. 609887.
Extended European Search Report dated Oct. 10, 2013, in European Application No. 11829187.1. (9 pages).
Bendig, M.M. Humanization of Rodent monoclonal anitbodies by CDR grafting. Methods: A Companion to Methods in Enzymology, 1995; vol. 8, p. 83-93.
Vajdos, Adams, Breece, Presta, De Vos, and Sidhu. Comprehensive functional maps of the antigen-binding site of an anti-ErBb2 antibody obtained with Shotgun scanning mutagenesis. Journal of Molecular Biology, 2002. vol. 320, pp. 415-428.
Dasset, F. et al. A peptide mimetic of an anti-CD4 monoclonal antibody by rational design. Biochemical and Biophysical Research Communications, 2003. vol. 307, pp. 198-205.
Nu, Nie, Huse, and Watkins. Humanization of a murine monoclonal anitbody by simultaneous optimization of framework and CDR residues Journal of Molecular Biology, 1999. vol. 294, pp. 151-162.
Dayman Chemical, "EP4 Recepton (N-term) Polyclonal Antiserum"; Product Information item #101770, Oct. 10, 2011, cited in EESR dated Oct. 10, 2013. (1 page).
Dayman Chemical, "EPA Recepton (C-Term) Polyclonal Antiserum"; item #10175, May 28, 2013, cited in EESR dated Oct. 10, 20136. (1 page).

\* cited by examiner

[Figure 1]
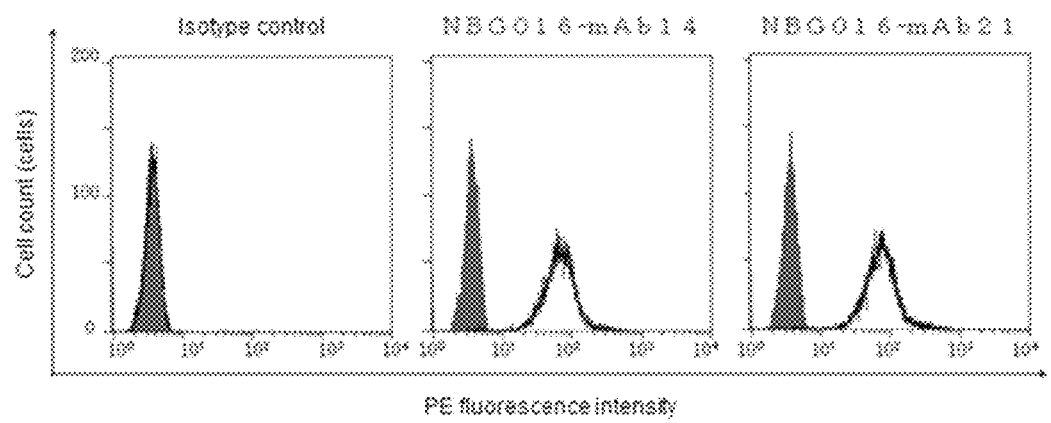
[Figure 2]
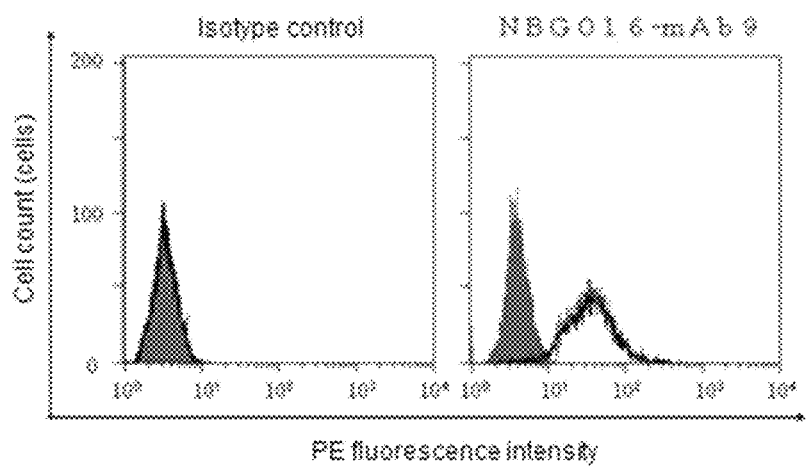

[Figure 3]
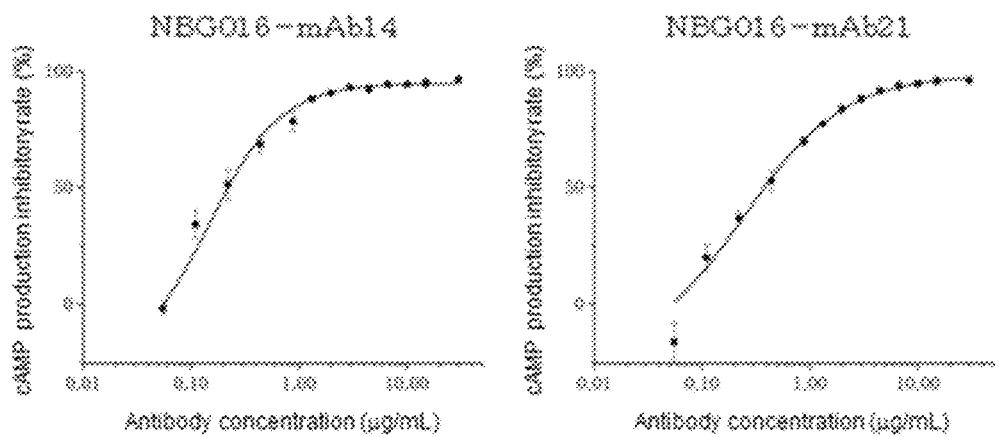
[Figure 4]
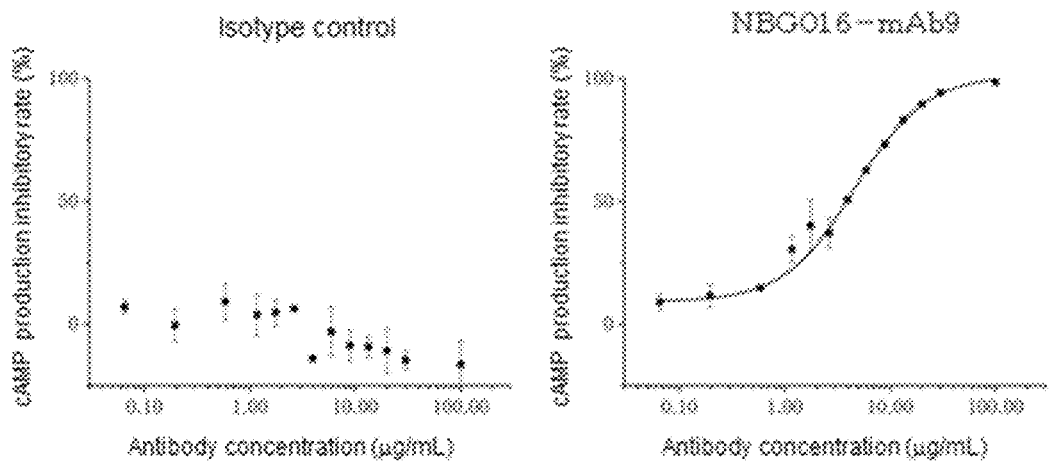

[Figure 5]
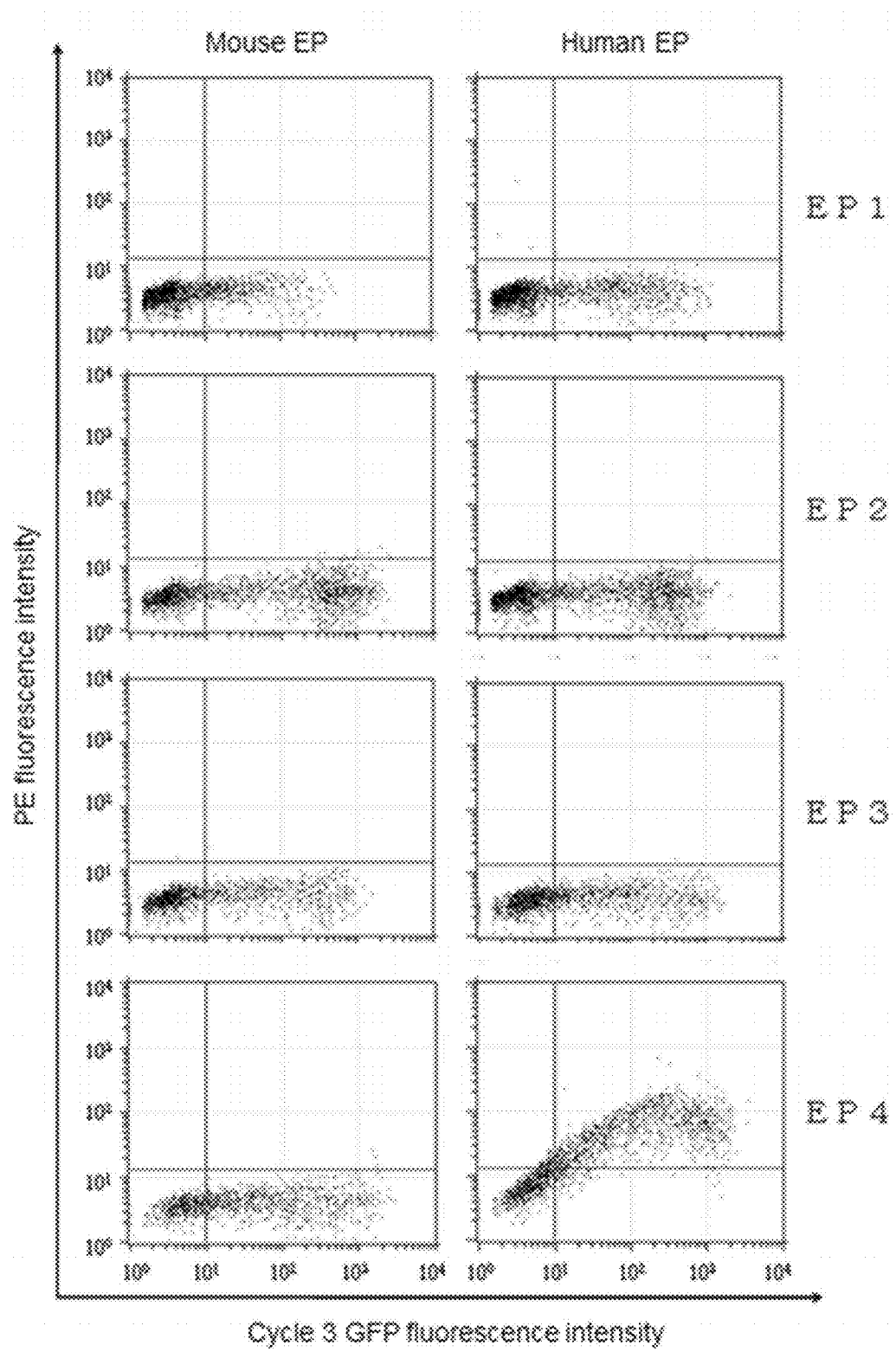

[Figure 6]
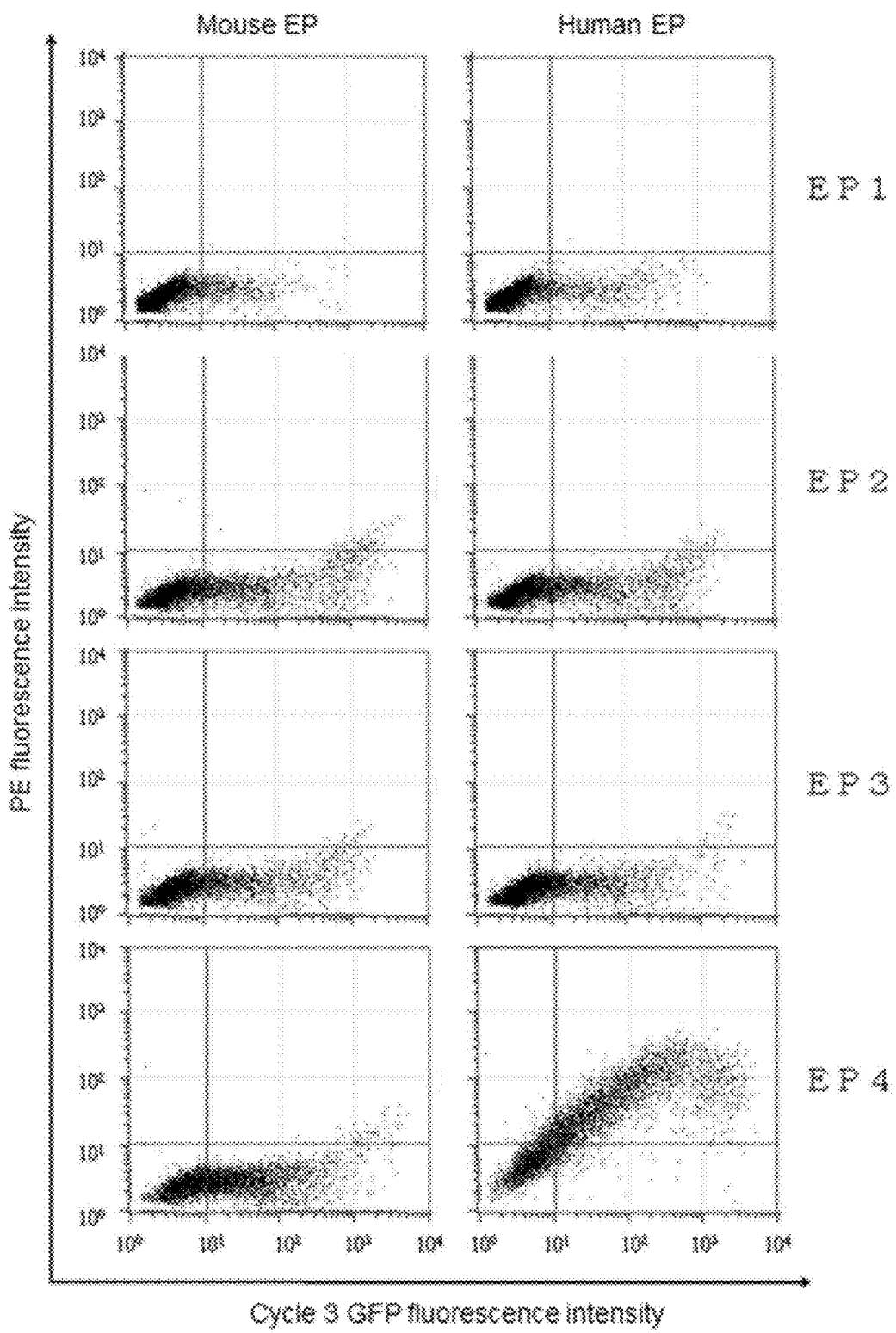

[Figure 7]
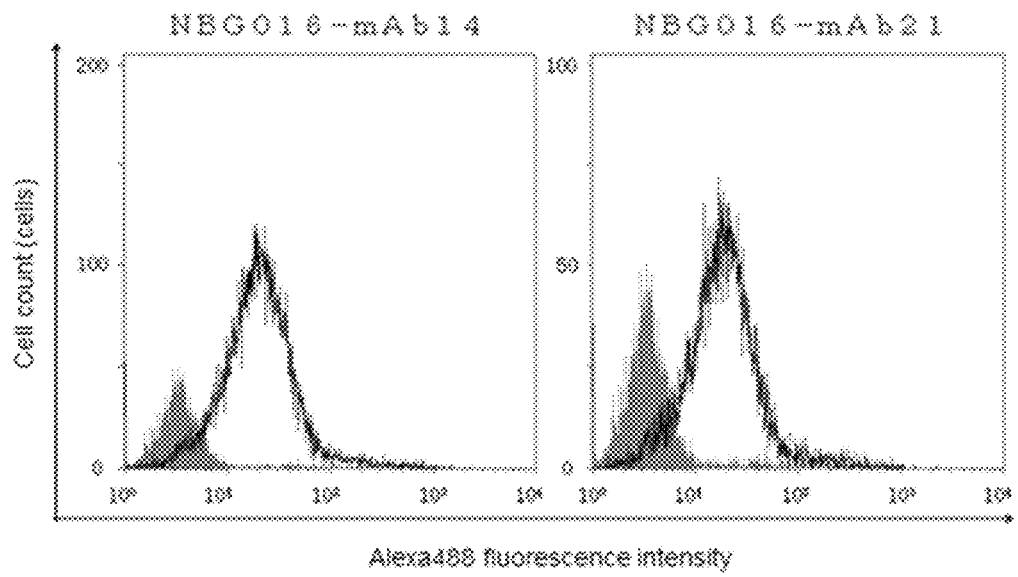
[Figure 8]
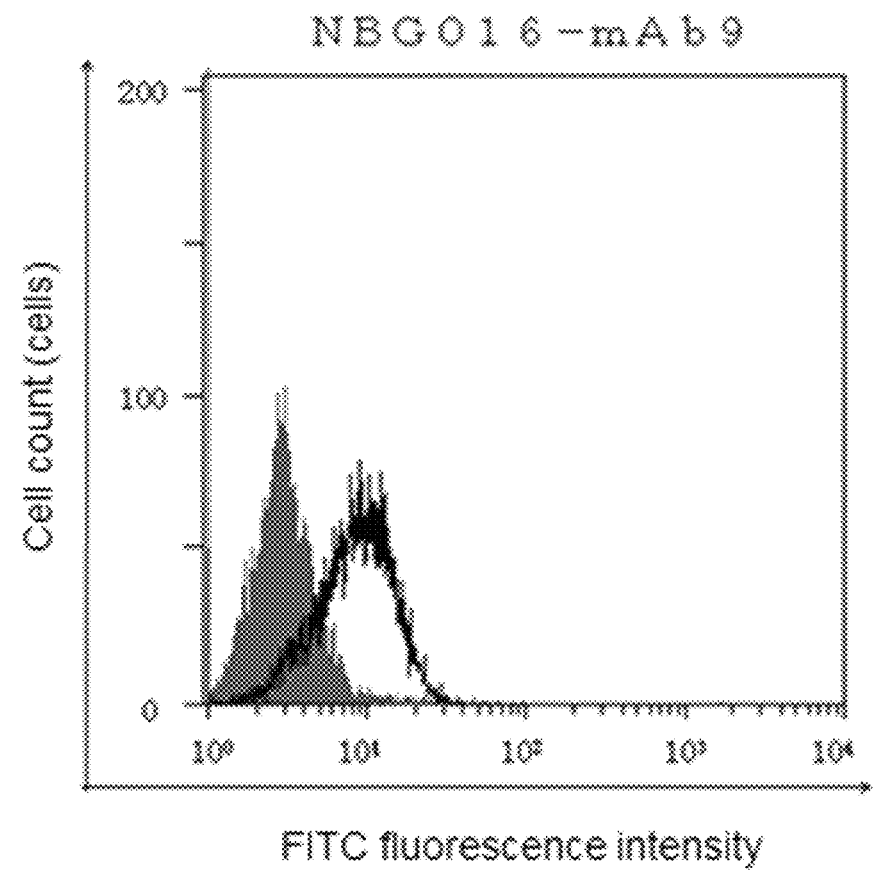

[Figure 9]
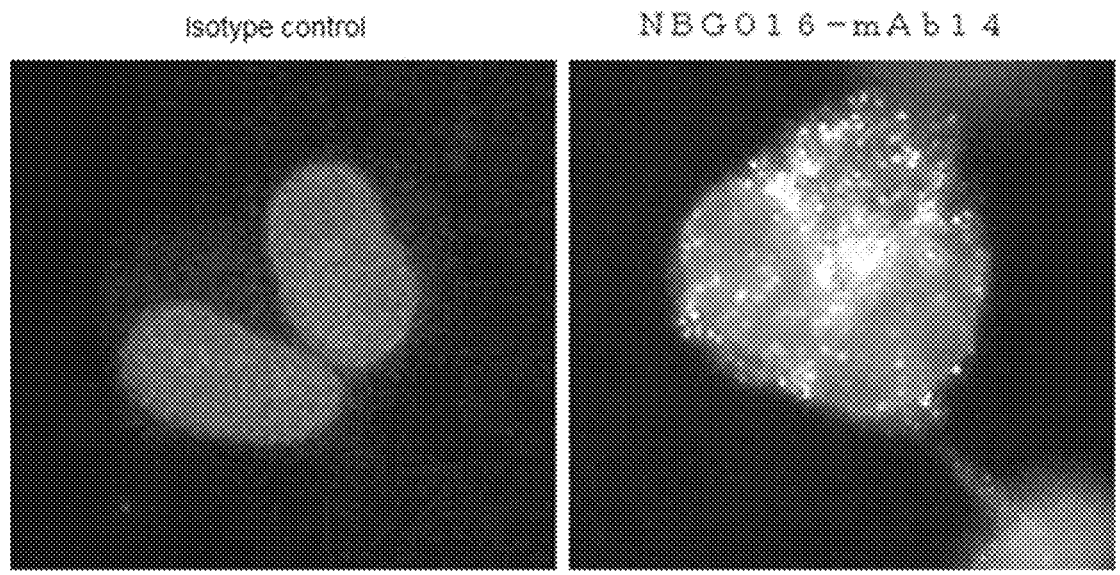
[Figure 10]
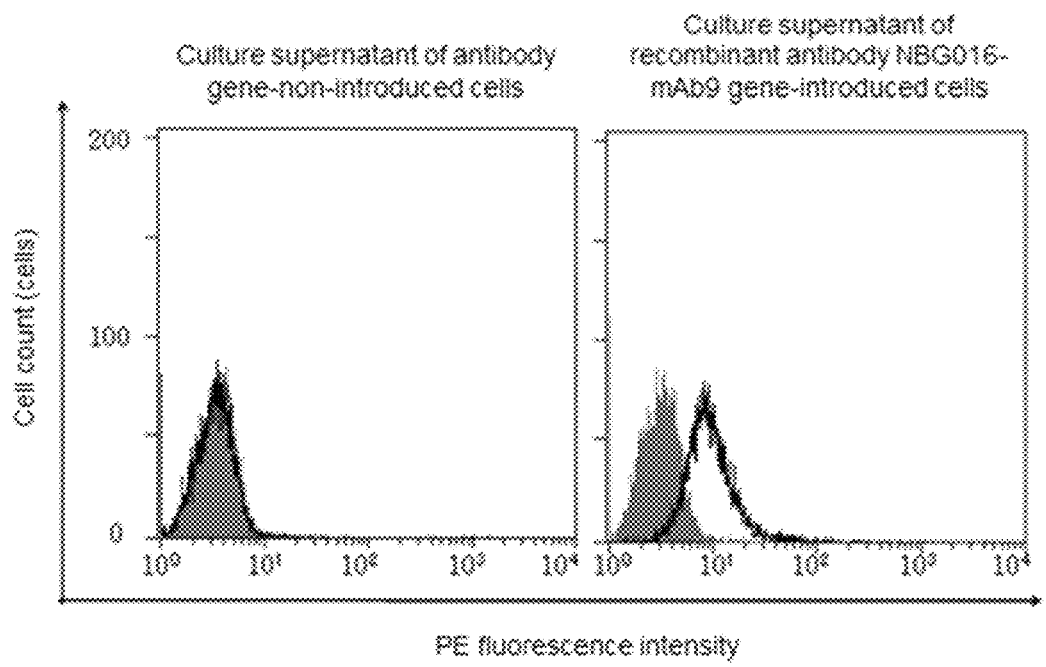

[Figure 11]
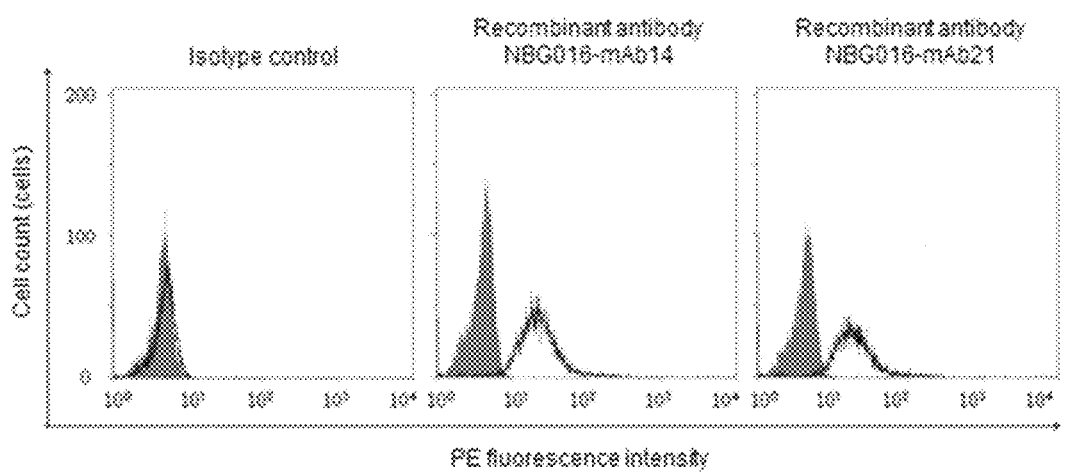

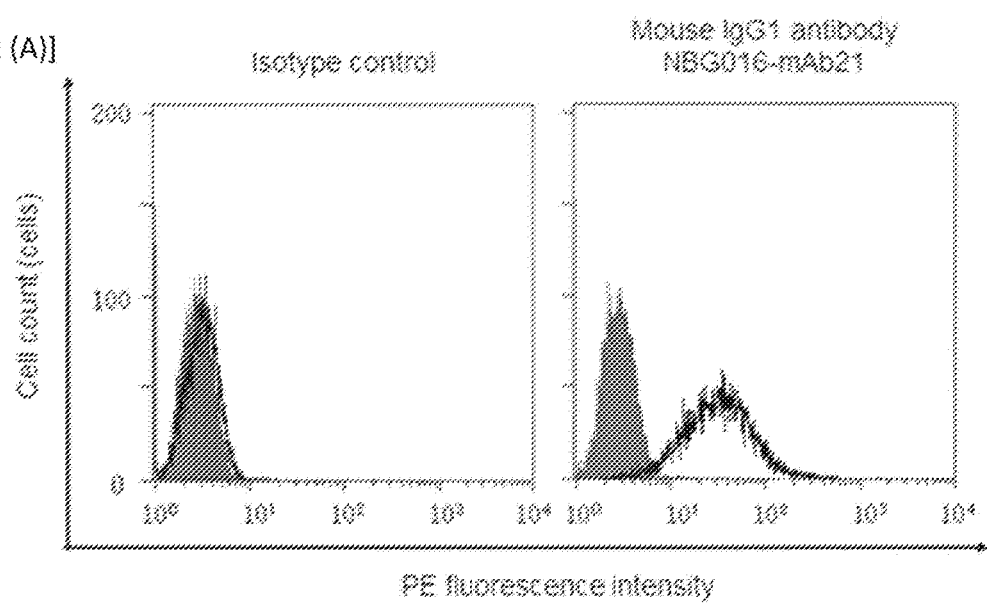
[Fig. 12 (A)]
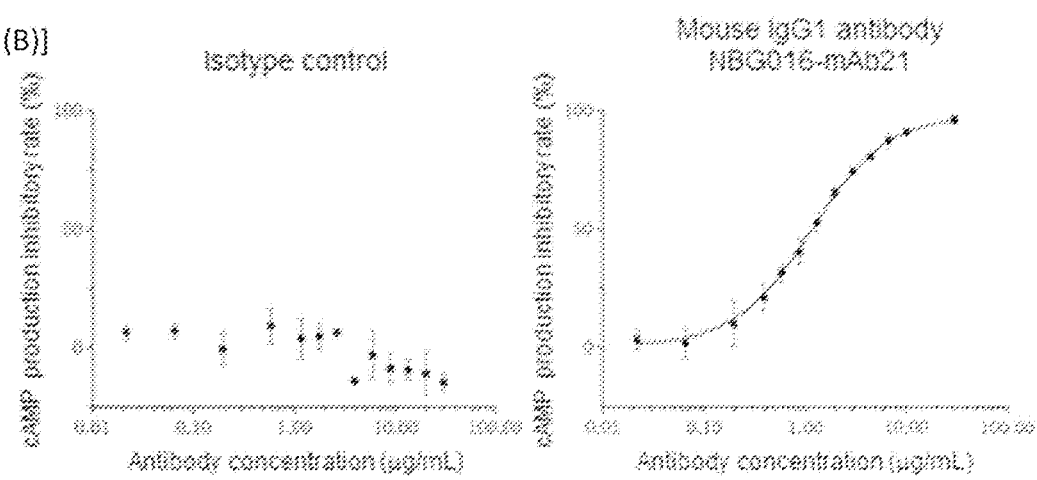
[Fig. 12 (B)]

[Figure 13]
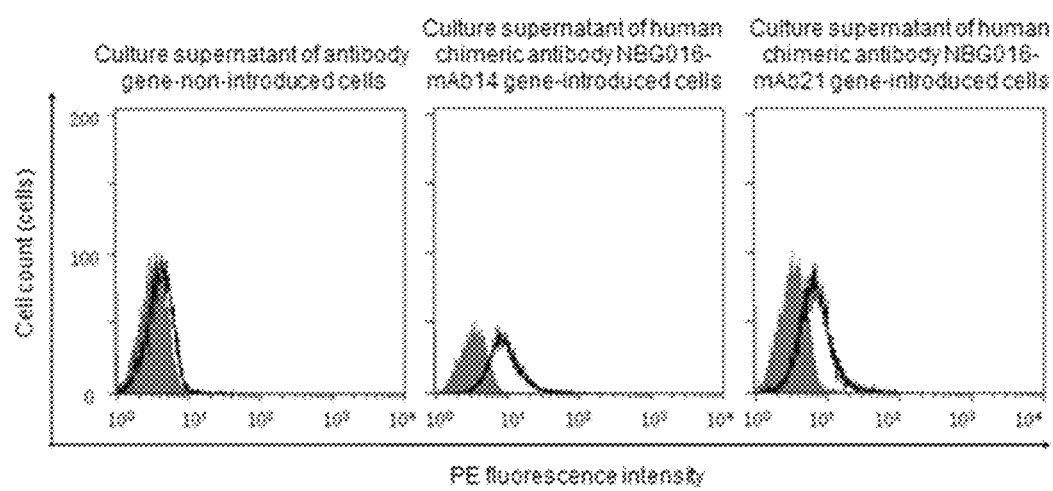

SEQUENCE LISTING

<160> NUMBER OF SEQ ID NOS: 63

<210> SEQ ID NO 1
<211> LENGTH: 435
<212> TYPE: DNA
<213> ORGANISM: Mus musculus

<400> SEQUENCE: 1
atggaatgga gatggatctt tctcttcctc ctgtcaggaa ctacaggtgt ccactctgag    60

```
atccagctgc agcagtctgg acctgaactg gtgaagcctg ggcttcagt gaaggtatca      120 tgcaaggctt ctggttttcc attttctacc tacaacatat actgggtgat ccagagccat     180
ggaaagcgcc ttgagtggat tggatatatt gatccttaca atggtggtac ttcctacaac     240
cagaagttca gggcaaggc cacattgact gttgacaagt cctccagcac agcctacatg      300
catctcaaca gactgacttc tgaggactct gcagtctatt actgtgcaag aagatggtat     360
acttacgacg gggactggtt tgcttactgg ggccaaggga ctctggtcac tgtctctgca     420
gccaaaacaa cagcc                                                      435
```

<210> SEQ ID NO 2
<211> LENGTH: 145
<212> TYPE: PRT
<213> ORGANISM: Mus musculus

<400> SEQUENCE: 2

```
Met Glu Trp Arg Trp Ile Phe Leu Phe Leu Leu Ser Gly Thr Thr Gly
1               5                   10                  15

Val His Ser Glu Ile Gln Leu Gln Gln Pro Gly Pro Glu Leu Val Lys
            20                  25                  30

Pro Gly Ala Ser Val Lys Val Ser Cys Lys Ala Ser Gly Phe Pro Phe
        35                  40                  45

Ser Thr Tyr Asn Ile Tyr Trp Val Ile Gln Ser His Gly Lys Arg Leu
    50                  55                  60

Glu Trp Ile Gly Tyr Ile Asp Pro Tyr Asn Gly Gly Thr Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met His Leu Asn Arg Leu Thr Ser Glu Asp Ser Ala Val
            100                 105                 110

Tyr Tyr Cys Ala Arg Arg Trp Tyr Thr Tyr Asp Gly Asp Trp Phe Ala
        115                 120                 125

Tyr Trp Gly Gln Gly Thr Leu Val Thr Val Ser Ala Ala Lys Thr Thr
    130                 135                 140

Ala
145
```

<210> SEQ ID NO 3
<211> LENGTH: 415
<212> TYPE: DNA
<213> ORGANISM: Mus musculus

<400> SEQUENCE: 3

```
atggacatga ggccccctgc tcagtttctt ggaatcttgt tgctctggtt tccaggtatc       60
aaatgtgaca tcaagatgac ccagtctcca tcttccatgt atgtatctct aggagagaga     120
gtcactatca cttgcaaggc gagtcaggac attaataggt atttaagctg gttccagcag     180
aaaccaggga aatctcctaa gaccctgatc tatcgtgcaa acagattgtt agatggagtc     240
ccatcaaggt tcagtggcag tggatctggg ctagattatt ctctcaccat cagcagcctg     300
gagtatgaag atatgggaaa ttattattgt ctacagtatg atgagtttcc attcacgttc     360
ggctcgggga caaagttgga aataaaacgg gctgatgctg caccaactgt atcca          415
```

<210> SEQ ID NO 4
<211> LENGTH: 138
<212> TYPE: PRT
<213> ORGANISM: Mus musculus

<400> SEQUENCE: 4

Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
            20                  25                  30

Met Tyr Val Ser Leu Gly Glu Arg Val Thr Ile Thr Cys Lys Ala Ser
        35                  40                  45

Gln Asp Ile Asn Arg Tyr Leu Ser Trp Phe Gln Gln Lys Pro Gly Lys
    50                  55                  60

Ser Pro Lys Thr Leu Ile Tyr Arg Ala Asn Arg Leu Leu Asp Gly Val
65                  70                  75                  80

Pro Ser Arg Phe Ser Gly Ser Gly Ser Gly Leu Asp Tyr Ser Leu Thr
                85                  90                  95

Ile Ser Ser Leu Glu Tyr Glu Asp Met Gly Asn Tyr Tyr Cys Leu Gln
            100                 105                 110

Tyr Asp Glu Phe Pro Phe Thr Phe Gly Ser Gly Thr Lys Leu Glu Ile
        115                 120                 125

Lys Arg Ala Asp Ala Ala Pro Thr Val Ser
    130                 135

<210> SEQ ID NO 5
<211> LENGTH: 5
<212> TYPE: PRT
<213> ORGANISM: Mus musculus

<400> SEQUENCE: 5

Thr Tyr Asn Ile Tyr
1               5

<210> SEQ ID NO 6
<211> LENGTH: 17
<212> TYPE: PRT
<213> ORGANISM: Mus musculus

<400> SEQUENCE: 6

Tyr Ile Asp Pro Tyr Asn Gly Gly Thr Ser Tyr Asn Gln Lys Phe Arg
1               5                   10                  15

Gly

<210> SEQ ID NO 7
<211> LENGTH: 12
<212> TYPE: PRT
<213> ORGANISM: Mus musculus

<400> SEQUENCE: 7

Arg Trp Tyr Thr Tyr Asp Gly Asp Trp Phe Ala Tyr
1               5                   10

<210> SEQ ID NO 8
<211> LENGTH: 11
<212> TYPE: PRT
<213> ORGANISM: Mus musculus

<400> SEQUENCE: 8

Lys Ala Ser Gln Asp Ile Asn Arg Tyr Leu Ser
1               5                   10

<210> SEQ ID NO 9
<211> LENGTH: 7

```
<212> TYPE: PRT
<213> ORGANISM: Mus musculus

<400> SEQUENCE: 9

Arg Ala Asn Arg Leu Leu Asp
1               5

<210> SEQ ID NO 10
<211> LENGTH: 9
<212> TYPE: PRT
<213> ORGANISM: Mus musculus

<400> SEQUENCE: 10

Leu Gln Tyr Asp Glu Phe Pro Phe Thr
1               5

<210> SEQ ID NO 11
<211> LENGTH: 435
<212> TYPE: DNA
<213> ORGANISM: Mus musculus

<400> SEQUENCE: 11
atggaatgga gatggatctt tctcttcctc ctgtcaggaa ctacaggtgt ccactctgag     60
atccagctgc agcagtctgg acctgaactg gtgaagcctg ggcttcagt gaaggtatca    120 tgcaaggctt ctggttttcc attctctacc tacaacatat actgggtgat ccagagccat    180
ggaaagagcc ttgagtggat tggatatatt gatccttaca atggtggtac ttcctacaac    240
cagaaattca gggcaaggc cacattgact gttgacaagt cctccagcac agcctacatg    300
catctcaaca gcctgacttc tgaggactct gcagtctatt actgtgcaag aagatggtat    360
acttacgacg gggactggtt tgcttactgg ggccaaggga ctctggtcac tgtctctgca    420
gccaaaacaa cagcc                                                     435

<210> SEQ ID NO 12
<211> LENGTH: 145
<212> TYPE: PRT
<213> ORGANISM: Mus musculus
<220> FEATURE:
<221> NAME/KEY: DOMAIN
<222> LOCATION: (50)..(54)
<223> OTHER INFORMATION: CDR1
<220> FEATURE:
<221> NAME/KEY: DOMAIN
<222> LOCATION: (69)..(85)
<223> OTHER INFORMATION: CDR2
<220> FEATURE:
<221> NAME/KEY: DOMAIN
<222> LOCATION: (118)..(129)
<223> OTHER INFORMATION: CDR3

<400> SEQUENCE: 12

Met Glu Trp Arg Trp Ile Phe Leu Phe Leu Leu Ser Gly Thr Thr Gly
1               5                   10                  15

Val His Ser Glu Ile Gln Leu Gln Gln Ser Gly Pro Glu Leu Val Lys
            20                  25                  30

Pro Gly Ala Ser Val Lys Val Ser Cys Lys Ala Ser Gly Phe Pro Phe
        35                  40                  45

Ser Thr Tyr Asn Ile Tyr Trp Val Ile Gln Ser His Gly Lys Ser Leu
    50                  55                  60

Glu Trp Ile Gly Tyr Ile Asp Pro Tyr Asn Gly Gly Thr Ser Tyr Asn
65                  70                  75                  80

Gln Lys Phe Arg Gly Lys Ala Thr Leu Thr Val Asp Lys Ser Ser Ser
```

Thr Ala Tyr Met His Leu Asn Ser Leu Thr Ser Glu Asp Ser Ala Val
            85                  90                  95
                100                 105                 110

Tyr Tyr Cys Ala Arg Arg Trp Tyr Thr Tyr Asp Gly Asp Trp Phe Ala
                115                 120                 125

Tyr Trp Gly Gln Gly Thr Leu Val Thr Val Ser Ala Ala Lys Thr Thr
        130                 135                 140

Ala
145

<210> SEQ ID NO 13
<211> LENGTH: 415
<212> TYPE: DNA
<213> ORGANISM: Mus musculus

<400> SEQUENCE: 13
atggacatga ggacccctgc tcagtttctt ggaatcttgt tgctctggtt tccaggtatc      60
aaatgtgaca tcaagatgac ccagtctcca tcttccatgt atgtatctct aggagagaga     120
gtcactatca cttgcaaggc gagtcaggac attaatagat atttaagctg gttccagcag     180
aaaccaggga atctcctaa gaccctgatc tatcgtgcaa acagaatgtt agatggggtc      240
ccatcaaggt tcagtggcag tggatctggg caagattatt ctctcaccat cagcagcctg     300
gaatacgaag atatgggaaa ttattattgt ctacagtatg atgagtttcc tttcacgttc     360
ggctcgggga caaagttgga aataaaacgg gctgatgctg caccaactgt atcca          415

<210> SEQ ID NO 14
<211> LENGTH: 138
<212> TYPE: PRT
<213> ORGANISM: Mus musculus
<220> FEATURE:
<221> NAME/KEY: DOMAIN
<222> LOCATION: (46)..(56)
<223> OTHER INFORMATION: CDR1
<220> FEATURE:
<221> NAME/KEY: DOMAIN
<222> LOCATION: (72)..(78)
<223> OTHER INFORMATION: CDR2
<220> FEATURE:
<221> NAME/KEY: DOMAIN
<222> LOCATION: (111)..(119)
<223> OTHER INFORMATION: CDR3

<400> SEQUENCE: 14

Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
                20                  25                  30

Met Tyr Val Ser Leu Gly Glu Arg Val Thr Ile Thr Cys Lys Ala Ser
            35                  40                  45

Gln Asp Ile Asn Arg Tyr Leu Ser Trp Phe Gln Gln Lys Pro Gly Lys
        50                  55                  60

Ser Pro Lys Thr Leu Ile Tyr Arg Ala Asn Arg Met Leu Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Glu Asp Met Gly Asn Tyr Tyr Cys Leu Gln
            100                 105                 110

Tyr Asp Glu Phe Pro Phe Thr Phe Gly Ser Gly Thr Lys Leu Glu Ile
        115                 120                 125

```
Lys Arg Ala Asp Ala Ala Pro Thr Val Ser
    130                 135

<210> SEQ ID NO 15
<211> LENGTH: 5
<212> TYPE: PRT
<213> ORGANISM: Mus musculus

<400> SEQUENCE: 15

Thr Tyr Asn Ile Tyr
1               5

<210> SEQ ID NO 16
<211> LENGTH: 17
<212> TYPE: PRT
<213> ORGANISM: Mus musculus

<400> SEQUENCE: 16

Tyr Ile Asp Pro Tyr Asn Gly Gly Thr Ser Tyr Asn Gln Lys Phe Arg
1               5                   10                  15

Gly

<210> SEQ ID NO 17
<211> LENGTH: 12
<212> TYPE: PRT
<213> ORGANISM: Mus musculus

<400> SEQUENCE: 17

Arg Trp Tyr Thr Tyr Asp Gly Asp Trp Phe Ala Tyr
1               5                   10

<210> SEQ ID NO 18
<211> LENGTH: 11
<212> TYPE: PRT
<213> ORGANISM: Mus musculus

<400> SEQUENCE: 18

Lys Ala Ser Gln Asp Ile Asn Arg Tyr Leu Ser
1               5                   10

<210> SEQ ID NO 19
<211> LENGTH: 7
<212> TYPE: PRT
<213> ORGANISM: Mus musculus

<400> SEQUENCE: 19

Arg Ala Asn Arg Met Leu Asp
1               5

<210> SEQ ID NO 20
<211> LENGTH: 9
<212> TYPE: PRT
<213> ORGANISM: Mus musculus

<400> SEQUENCE: 20

Leu Gln Tyr Asp Glu Phe Pro Phe Thr
1               5

<210> SEQ ID NO 21
<211> LENGTH: 488
<212> TYPE: PRT
<213> ORGANISM: Homo sapiens

<400> SEQUENCE: 21
```

```
Met Ser Thr Pro Gly Val Asn Ser Ala Ser Leu Ser Pro Asp Arg
1               5                   10                  15

Leu Asn Ser Pro Val Thr Ile Pro Ala Val Met Phe Ile Phe Gly Val
            20                  25                  30

Val Gly Asn Leu Val Ala Ile Val Val Leu Cys Lys Ser Arg Lys Glu
        35                  40                  45

Gln Lys Glu Thr Thr Phe Tyr Thr Leu Val Cys Gly Leu Ala Val Thr
50                      55                  60

Asp Leu Leu Gly Thr Leu Val Ser Pro Val Thr Ile Ala Thr Tyr
65                  70                  75                  80

Met Lys Gly Gln Trp Pro Gly Gly Gln Pro Leu Cys Glu Tyr Ser Thr
                85                  90                  95

Phe Ile Leu Leu Phe Phe Ser Leu Ser Gly Leu Ser Ile Ile Cys Ala
                100                 105                 110

Met Ser Val Glu Arg Tyr Leu Ala Ile Asn His Ala Tyr Phe Tyr Ser
        115                 120                 125

His Tyr Val Asp Lys Arg Leu Ala Gly Leu Thr Leu Phe Ala Val Tyr
    130                 135                 140

Ala Ser Asn Val Leu Phe Cys Ala Leu Pro Asn Met Gly Leu Gly Ser
145                 150                 155                 160

Ser Arg Leu Gln Tyr Pro Asp Thr Trp Cys Phe Ile Asp Trp Thr Thr
                165                 170                 175

Asn Val Thr Ala His Ala Ala Tyr Ser Tyr Met Tyr Ala Gly Phe Ser
                180                 185                 190

Ser Phe Leu Ile Leu Ala Thr Val Leu Cys Asn Val Leu Val Cys Gly
            195                 200                 205

Ala Leu Leu Arg Met His Arg Gln Phe Met Arg Thr Ser Leu Gly
            210                 215                 220

Thr Glu Gln His His Ala Ala Ala Ala Ser Val Ala Ser Arg Gly
225                 230                 235                 240

His Pro Ala Ala Ser Pro Ala Leu Pro Arg Leu Ser Asp Phe Arg Arg
                245                 250                 255

Arg Arg Ser Phe Arg Arg Ile Ala Gly Ala Glu Ile Gln Met Val Ile
            260                 265                 270

Leu Leu Ile Ala Thr Ser Leu Val Val Leu Ile Cys Ser Ile Pro Leu
            275                 280                 285

Val Val Arg Val Phe Val Asn Gln Leu Tyr Gln Pro Ser Leu Glu Arg
        290                 295                 300

Glu Val Ser Lys Asn Pro Asp Leu Gln Ala Ile Arg Ile Ala Ser Val
305                 310                 315                 320

Asn Pro Ile Leu Asp Pro Trp Ile Tyr Ile Leu Leu Arg Lys Thr Val
                325                 330                 335

Leu Ser Lys Ala Ile Glu Lys Ile Lys Cys Leu Phe Cys Arg Ile Gly
            340                 345                 350

Gly Ser Arg Arg Glu Arg Ser Gly Gln His Cys Ser Asp Ser Gln Arg
        355                 360                 365

Thr Ser Ser Ala Met Ser Gly His Ser Arg Ser Phe Ile Ser Arg Glu
    370                 375                 380

Leu Lys Glu Ile Ser Ser Thr Ser Gln Thr Leu Leu Pro Asp Leu Ser
385                 390                 395                 400

Leu Pro Asp Leu Ser Glu Asn Gly Leu Gly Gly Arg Asn Leu Leu Pro
                405                 410                 415
```

Gly Val Pro Gly Met Gly Leu Ala Gln Glu Asp Thr Thr Ser Leu Arg
                420                 425                 430

Thr Leu Arg Ile Ser Glu Thr Ser Asp Ser Ser Gln Gly Gln Asp Ser
            435                 440                 445

Glu Ser Val Leu Leu Val Asp Glu Ala Gly Gly Ser Gly Arg Ala Gly
        450                 455                 460

Pro Ala Pro Lys Gly Ser Ser Leu Gln Val Thr Phe Pro Ser Glu Thr
465                 470                 475                 480

Leu Asn Leu Ser Glu Lys Cys Ile
                485

<210> SEQ ID NO 22
<211> LENGTH: 1413
<212> TYPE: DNA
<213> ORGANISM: Mus musculus

<400> SEQUENCE: 22

```
atggaatgga gatggatctt tctcttcctc ctgtcaggaa ctacaggtgt ccactctgag    60
atccagctgc agcagtctgg acctgaactg gtgaagcctg ggcttcagt gaaggtatca   120
tgcaaggctt ctggttttcc attttctacc tacaacatat actgggtgat ccagagccat   180
ggaaagcgcc ttgagtggat tggatatatt gatccttaca atggtggtac ttcctacaac   240
cagaagttca gggcaaggc cacattgact gttgacaagt cctccagcac agcctacatg   300
catctcaaca gactgacttc tgaggactct gcagtctatt actgtgcaag aagatggtat   360
acttacgacg gggactggtt tgcttactgg ggccaaggga ctctggtcac tgtctctgca   420
gccaaaacaa cagccccatc ggtctatcca ctggcccctg tgtgtggaga tacaactggc   480
tcctcggtga ctctaggatg cctggtcaag ggttatttcc ctgagccagt gaccttgacc   540
tggaactctg gatccctgtc cagtggtgtg cacaccttcc cagctgtcct gcagtctgac   600
ctctacaccc tcagcagctc agtgactgta acctcgagca cctggcccag ccagtccatc   660
acctgcaatg tggcccaccc ggcaagcagc accaaggtgg acaagaaaat tgagcccaga   720
gggcccacaa tcaagccctg tcctccatgc aaatgcccag cacctaacct cttgggtgga   780
ccatccgtct tcatcttccc tccaaagatc aaggatgtac tcatgatctc cctgagcccc   840
atagtcacat gtgtggtggt ggatgtgagc gaggatgacc cagatgtcca gatcagctgg   900
tttgtgaaca acgtggaagt acacacagct cagacacaaa cccatagaga ggattacaac   960
agtactctcc gggtggtcag tgccctcccc atccagcacc aggactggat gagtggcaag  1020
gagttcaaat gcaaggtcaa caacaaagac ctcccagcgc ccatcgagag aaccatctca  1080
aaacccaaag ggtcagtaag agctccacag gtatatgtct tgcctccacc agaagaagag  1140
atgactaaga acaggtcac tctgacctgc atggtcacag acttcatgcc tgaagacatt  1200
tacgtggagt ggaccaacaa cgggaaaaca gagctaaact acaagaacac tgaaccagtc  1260
ctggactctg atggttctta cttcatgtac agcaagctga gagtgaaaaa gaagaactgg  1320
gtggaaagaa atagctactc ctgttcagtg gtccacgagg gtctgcacaa tcaccacacg  1380
actaagagct ctcccactc tcctggtaaa tga                               1413
```

<210> SEQ ID NO 23
<211> LENGTH: 470
<212> TYPE: PRT
<213> ORGANISM: Mus musculus

<400> SEQUENCE: 23

```
Met Glu Trp Arg Trp Ile Phe Leu Phe Leu Leu Ser Gly Thr Thr Gly
1               5                   10                  15

Val His Ser Glu Ile Gln Leu Gln Gln Ser Gly Pro Glu Leu Val Lys
            20                  25                  30

Pro Gly Ala Ser Val Lys Val Ser Cys Lys Ala Ser Gly Phe Pro Phe
            35                  40                  45

Ser Thr Tyr Asn Ile Tyr Trp Val Ile Gln Ser His Gly Lys Arg Leu
    50                  55                  60

Glu Trp Ile Gly Tyr Ile Asp Pro Tyr Asn Gly Thr Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met His Leu Asn Arg Leu Thr Ser Glu Asp Ser Ala Val
                100                 105                 110

Tyr Tyr Cys Ala Arg Arg Trp Tyr Thr Tyr Asp Gly Asp Trp Phe Ala
            115                 120                 125

Tyr Trp Gly Gln Gly Thr Leu Val Thr Val Ser Ala Ala Lys Thr Thr
        130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
            165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Thr Ser Ser Thr Trp Pro Ser Gln Ser Ile Thr Cys Asn Val
    210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
            245                 250                 255

Leu Leu Gly Gly Pro Ser Val Phe Ile Phe Pro Pro Lys Ile Lys Asp
            260                 265                 270

Val Leu Met Ile Ser Leu Ser Pro Ile Val Thr Cys Val Val Val Asp
        275                 280                 285

Val Ser Glu Asp Asp Pro Asp Val Gln Ile Ser Trp Phe Val Asn Asn
        290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
            325                 330                 335

Met Ser Gly Lys Glu Phe Lys Cys Lys Val Asn Asn Lys Asp Leu Pro
            340                 345                 350

Ala Pro Ile Glu Arg Thr Ile Ser Lys Pro Lys Gly Ser Val Arg Ala
        355                 360                 365

Pro Gln Val Tyr Val Leu Pro Pro Glu Glu Met Thr Lys Lys
370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
            405                 410                 415

Thr Glu Pro Val Leu Asp Ser Asp Gly Ser Tyr Phe Met Tyr Ser Lys
```

```
                    420             425             430
Leu Arg Val Glu Lys Lys Asn Trp Val Glu Arg Asn Ser Tyr Ser Cys
            435                 440                 445
Ser Val Val His Glu Gly Leu His Asn His His Thr Thr Lys Ser Phe
        450                 455                 460
Ser His Ser Pro Gly Lys
465                 470

<210> SEQ ID NO 24
<211> LENGTH: 711
<212> TYPE: DNA
<213> ORGANISM: Mus musculus

<400> SEQUENCE: 24
atggacatga ggacccctgc tcagtttctt ggaatcttgt tgctctggtt tccaggtatc    60
aaatgtgaca tcaagatgac ccagtctcca tcttccatgt atgtatctct aggagagaga   120
gtcactatca cttgcaaggc gagtcaggac attaataggt atttaagctg gttccagcag   180
aaaccaggga atctcctaa gaccctgatc tatcgtgcaa acagattgtt agatggagtc    240
ccatcaaggt tcagtggcag tggatctggg ctagattatt ctctcaccat cagcagcctg   300
gagtatgaag atatgggaaa ttattattgt ctacagtatg atgagtttcc attcacgttc   360
ggctcgggga caaagttgga aataaaacgg gctgatgctg caccaactgt atccatcttc   420
ccaccatcca gtgagcagtt aacatctgga ggtgcctcag tcgtgtgctt cttgaacaac   480
ttctacccca agacatcaa tgtcaagtgg aagattgatg gcagtgaacg acaaaatggc    540
gtcctgaaca gttggactga tcaggacagc aaagacagca cctacagcat gagcagcacc   600
ctcacgttga ccaaggacga gtatgaacga cataacagct atacctgtga ggccactcac   660
aagacatcaa cttcacccat tgtcaagagc ttcaacagga atgagtgtta a             711

<210> SEQ ID NO 25
<211> LENGTH: 236
<212> TYPE: PRT
<213> ORGANISM: Mus musculus

<400> SEQUENCE: 25

Met Asp Met Arg Thr Pro Ala Gln Phe Leu Gly Ile Leu Leu Leu Trp
1               5                   10                  15
Phe Pro Gly Ile Lys Cys Asp Ile Lys Met Thr Gln Ser Pro Ser Ser
            20                  25                  30
Met Tyr Val Ser Leu Gly Glu Arg Val Thr Ile Thr Cys Lys Ala Ser
        35                  40                  45
Gln Asp Ile Asn Arg Tyr Leu Ser Trp Phe Gln Gln Lys Pro Gly Lys
    50                  55                  60
Ser Pro Lys Thr Leu Ile Tyr Arg Ala Asn Arg Leu Leu Asp Gly Val
65                  70                  75                  80
Pro Ser Arg Phe Ser Gly Ser Gly Ser Gly Leu Asp Tyr Ser Leu Thr
                85                  90                  95
Ile Ser Ser Leu Glu Tyr Glu Asp Met Gly Asn Tyr Tyr Cys Leu Gln
            100                 105                 110
Tyr Asp Glu Phe Pro Phe Thr Phe Gly Ser Gly Thr Lys Leu Glu Ile
        115                 120                 125
Lys Arg Ala Asp Ala Ala Pro Thr Val Ser Ile Phe Pro Pro Ser Ser
    130                 135                 140
Glu Gln Leu Thr Ser Gly Gly Ala Ser Val Val Cys Phe Leu Asn Asn
```

```
            145                 150                 155                 160
        Phe Tyr Pro Lys Asp Ile Asn Val Lys Trp Lys Ile Asp Gly Ser Glu
                    165                 170                 175

Arg Gln Asn Gly Val Leu Asn Ser Trp Thr Asp Gln Asp Ser Lys Asp
                    180                 185                 190

Ser Thr Tyr Ser Met Ser Ser Thr Leu Thr Leu Thr Lys Asp Glu Tyr
                    195                 200                 205

Glu Arg His Asn Ser Tyr Thr Cys Glu Ala Thr His Lys Thr Ser Thr
                210                 215                 220

Ser Pro Ile Val Lys Ser Phe Asn Arg Asn Glu Cys
        225                 230                 235

<210> SEQ ID NO 26
<211> LENGTH: 1413
<212> TYPE: DNA
<213> ORGANISM: Mus musculus

<400> SEQUENCE: 26
atggaatgga gatggatctt tctcttcctc ctgtcaggaa ctacaggtgt ccactctgag      60
atccagctgc agcagtctgg acctgaactg gtgaagcctg gggcttcagt gaaggtatca     120
tgcaaggctt ctggttttcc attctctacc tacaacatat actgggtgat ccagagccat     180
ggaaagagcc ttgagtggat tggatatatt gatccttaca atggtggtac ttcctacaac     240
cagaaattca ggggcaaggc cacattgact gttgacaagt cctccagcac agcctacatg     300
catctcaaca gcctgacttc tgaggactct gcagtctatt actgtgcaag aagatggtat     360
acttacgacg gggactggtt tgcttactgg ggccaaggga ctctggtcac tgtctctgca     420
gccaaaacaa cagccccatc ggtctatcca ctggcccctg tgtgtggaga tacaactggc     480
tcctcggtga ctctaggatg cctggtcaag ggttatttcc ctgagccagt gaccttgacc     540
tggaactctg gatccctgtc cagtggtgtg cacaccttcc cagctgtcct gcagtctgac     600
ctctacaccc tcagcagctc agtgactgta acctcgagca cctggcccag ccagtccatc     660
acctgcaatg tggcccaccc ggcaagcagc accaaggtgg acaagaaaat tgagcccaga     720
gggcccacaa tcaagccctg tcctccatgc aaatgcccag cacctaacct cttgggtgga     780
ccatccgtct tcatcttccc tccaaagatc aaggatgtac tcatgatctc cctgagcccc     840
atagtcacat gtgtggtggt ggatgtgagc gaggatgacc cagatgtcca gatcagctgg     900
tttgtgaaca acgtggaagt acacacagct cagacacaaa cccatagaga ggattacaac     960
agtactctcc gggtggtcag tgccctcccc atccagcacc aggactggat gagtggcaag    1020
gagttcaaat gcaaggtcaa caacaaagac ctcccagcgc ccatcgagag aaccatctca    1080
aaacccaaag ggtcagtaag agctccacag gtatatgtct tgcctccacc agaagaagag    1140
atgactaaga acaggtcac tctgacctgc atggtcacag acttcatgcc tgaagacatt    1200
tacgtggagt ggaccaacaa cgggaaaaca gagctaaact acaagaacac tgaaccagtc    1260
ctggactctg atggttctta cttcatgtac agcaagctga gtggaaaaa gaagaactgg    1320 gtggaaagaa atagctactc ctgttcagtg gtccacgagg gtctgcacaa tcaccacacg    1380
actaagagct ctcccactc tcctggtaaa tga                                  1413

<210> SEQ ID NO 27
<211> LENGTH: 470
<212> TYPE: PRT
<213> ORGANISM: Mus musculus
```

```
<400> SEQUENCE: 27

Met Glu Trp Arg Trp Ile Phe Leu Phe Leu Leu Ser Gly Thr Thr Gly
1               5                   10                  15

Val His Ser Glu Ile Gln Leu Gln Gln Ser Gly Pro Glu Leu Val Lys
            20                  25                  30

Pro Gly Ala Ser Val Lys Val Ser Cys Lys Ala Ser Gly Phe Pro Phe
        35                  40                  45

Ser Thr Tyr Asn Ile Tyr Trp Val Ile Gln Ser His Gly Lys Ser Leu
    50                  55                  60

Glu Trp Ile Gly Tyr Ile Asp Pro Tyr Asn Gly Gly Thr Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met His Leu Asn Ser Leu Thr Ser Glu Asp Ser Ala Val
            100                 105                 110

Tyr Tyr Cys Ala Arg Arg Trp Tyr Thr Tyr Asp Gly Asp Trp Phe Ala
        115                 120                 125

Tyr Trp Gly Gln Gly Thr Leu Val Thr Val Ser Ala Ala Lys Thr Thr
    130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Thr Ser Ser Thr Trp Pro Ser Gln Ser Ile Thr Cys Asn Val
    210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
                245                 250                 255

Leu Leu Gly Gly Pro Ser Val Phe Ile Phe Pro Pro Lys Ile Lys Asp
            260                 265                 270

Val Leu Met Ile Ser Leu Ser Pro Ile Val Thr Cys Val Val Val Asp
        275                 280                 285

Val Ser Glu Asp Asp Pro Asp Val Gln Ile Ser Trp Phe Val Asn Asn
    290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
            340                 345                 350

Ala Pro Ile Glu Arg Thr Ile Ser Lys Pro Lys Gly Ser Val Arg Ala
        355                 360                 365

Pro Gln Val Tyr Val Leu Pro Pro Pro Glu Glu Glu Met Thr Lys Lys
    370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415
```

```
Thr Glu Pro Val Leu Asp Ser Asp Gly Ser Tyr Phe Met Tyr Ser Lys
            420                 425                 430

Leu Arg Val Glu Lys Lys Asn Trp Val Glu Arg Asn Ser Tyr Ser Cys
        435                 440                 445

Ser Val Val His Glu Gly Leu His Asn His His Thr Thr Lys Ser Phe
    450                 455                 460

Ser His Ser Pro Gly Lys
465                 470

<210> SEQ ID NO 28
<211> LENGTH: 711
<212> TYPE: DNA
<213> ORGANISM: Mus musculus

<400> SEQUENCE: 28
atggacatga ggacccctgc tcagtttctt ggaatcttgt tgctctggtt tccaggtatc      60
aaatgtgaca tcaagatgac ccagtctcca tcttccatgt atgtatctct aggagagaga    120
gtcactatca cttgcaaggc gagtcaggac attaatagat atttaagctg gttccagcag    180
aaaccaggga atctcctaa gaccctgatc tatcgtgcaa acagaatgtt agatggggtc     240
ccatcaaggt tcagtggcag tggatctggg caagattatt ctctcaccat cagcagcctg    300
gaatacgaag atatgggaaa ttattattgt ctacagtatg atgagtttcc tttcacgttc    360
ggctcgggga caaagttgga aataaaacgg gctgatgctg caccaactgt atccatcttc    420
ccaccatcca gtgagcagtt aacatctgga ggtgcctcag tcgtgtgctt cttgaacaac    480 ttctaccccca agacatcaa tgtcaagtgg aagattgatg gcagtgaacg acaaaatggc    540
gtcctgaaca gttggactga tcaggacagc aaagacagca cctacagcat gagcagcacc    600
ctcacgttga ccaaggacga gtatgaacga cataacagct atacctgtga ggccactcac    660
aagacatcaa cttcacccat tgtcaagagc ttcaacagga atgagtgtta a              711

<210> SEQ ID NO 29
<211> LENGTH: 236
<212> TYPE: PRT
<213> ORGANISM: Mus musculus

<400> SEQUENCE: 29

Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
            20                  25                  30

Met Tyr Val Ser Leu Gly Glu Arg Val Thr Ile Thr Cys Lys Ala Ser
        35                  40                  45

Gln Asp Ile Asn Arg Tyr Leu Ser Trp Phe Gln Gln Lys Pro Gly Lys
    50                  55                  60

Ser Pro Lys Thr Leu Ile Tyr Arg Ala Asn Arg Met Leu Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Glu Asp Met Gly Asn Tyr Tyr Cys Leu Gln
            100                 105                 110

Tyr Asp Glu Phe Pro Phe Thr Phe Gly Ser Gly Thr Lys Leu Glu Ile
        115                 120                 125

Lys Arg Ala Asp Ala Ala Pro Thr Val Ser Ile Phe Pro Pro Ser Ser
    130                 135                 140
```

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
            165                 170                 175

Arg Gln Asn Gly Val Leu Asn Ser Trp Thr Asp Gln Asp Ser Lys Asp
        180                 185                 190

Ser Thr Tyr Ser Met Ser Ser Thr Leu Thr Leu Thr Lys Asp Glu Tyr
    195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235

<210> SEQ ID NO 30
<211> LENGTH: 109
<212> TYPE: DNA
<213> ORGANISM: Artificial
<220> FEATURE:
<223> OTHER INFORMATION: synthetic DNA

<400> SEQUENCE: 30
ggggacaagt ttgtacaaaa aagcaggctt cgaaggagat agaaccatgg agacagacac      60
actcctgcta tgggtactgc tgctctgggt tccaggttcc actggtgac                 109

<210> SEQ ID NO 31
<211> LENGTH: 30
<212> TYPE: DNA
<213> ORGANISM: Artificial
<220> FEATURE:
<223> OTHER INFORMATION: synthetic DNA

<400> SEQUENCE: 31
gacccagctt tcttgtacaa agtggtcccc                                       30

<210> SEQ ID NO 32
<211> LENGTH: 67
<212> TYPE: DNA
<213> ORGANISM: Artificial
<220> FEATURE:
<223> OTHER INFORMATION: synthetic DNA

<400> SEQUENCE: 32
caccatggag acagacacac tcctgctatg ggtactgctg ctctgggttc caggttccac      60
tggtgac                                                                67

<210> SEQ ID NO 33
<211> LENGTH: 23
<212> TYPE: DNA
<213> ORGANISM: Artificial
<220> FEATURE:
<223> OTHER INFORMATION: synthetic DNA

<400> SEQUENCE: 33
aggggccagt ggatagaccg atg                                              23

<210> SEQ ID NO 34
<211> LENGTH: 24
<212> TYPE: DNA
<213> ORGANISM: Artificial
<220> FEATURE:
<223> OTHER INFORMATION: synthetic DNA

<400> SEQUENCE: 34
ggctgttgtt ttggctgcag agac                                          24

<210> SEQ ID NO 35
<211> LENGTH: 24
<212> TYPE: DNA
<213> ORGANISM: Artificial
<220> FEATURE:
<223> OTHER INFORMATION: synthetic DNA

<400> SEQUENCE: 35
actggatggt gggaagatgg atac                                          24

<210> SEQ ID NO 36
<211> LENGTH: 24
<212> TYPE: DNA
<213> ORGANISM: Artificial
<220> FEATURE:
<223> OTHER INFORMATION: synthetic DNA

<400> SEQUENCE: 36
tggatacagt tggtgcagca tcag                                          24

<210> SEQ ID NO 37
<211> LENGTH: 43
<212> TYPE: DNA
<213> ORGANISM: Artificial
<220> FEATURE:
<223> OTHER INFORMATION: synthetic DNA

<400> SEQUENCE: 37
cactgaccct acgcgtatgg aatggagatg gatctttctc ttc                     43

<210> SEQ ID NO 38
<211> LENGTH: 40
<212> TYPE: DNA
<213> ORGANISM: Artificial
<220> FEATURE:
<223> OTHER INFORMATION: synthetic DNA

<400> SEQUENCE: 38
ataagaatgc ggccgctcat ttaccaggag agtgggagag                         40

<210> SEQ ID NO 39
<211> LENGTH: 39
<212> TYPE: DNA
<213> ORGANISM: Artificial
<220> FEATURE:
<223> OTHER INFORMATION: synthetic DNA

<400> SEQUENCE: 39
ttgcagccag gaacgcgtat ggacatgagg acccctgct                          39

<210> SEQ ID NO 40
<211> LENGTH: 40
<212> TYPE: DNA
<213> ORGANISM: Artificial
<220> FEATURE:
<223> OTHER INFORMATION: synthetic DNA

<400> SEQUENCE: 40
ataagaatgc ggccgcttaa cactcattcc tgttgaagct                         40

<210> SEQ ID NO 41
<211> LENGTH: 429

<210> SEQ ID NO 41
<211> LENGTH: 429
<212> TYPE: DNA
<213> ORGANISM: Mus musculus

<400> SEQUENCE: 41

```
atggctgtcc tggtgctgtt cctctgcctg gttgcatttc caagctgtgt cctgtcccag    60
gtgcagctga aggagtcagg gcctggcctg gtggcgccct cacagagcct ttccatcact   120
tgcactgtct ctgggttttc attaagcagc tatactatac actgggttcg ccagcctcca   180
ggaaggggtc tggagtggct gggagtgata tgggctggtg aagcacaaa ctataattcg   240
gctctcatgt ctagactgcg catcagcaaa gacacctcca ggagccaagt tttcctaaaa   300
gtgaacagtc tgcaaactga tgactcagcc atatactact gtgccagaaa tgacttcggc   360
tacgggtttg cttactgggg ccaagggact ctggtcactg tctctgcagc caaaacaaca   420
gccaatcgg                                                           429
```

<210> SEQ ID NO 42
<211> LENGTH: 420
<212> TYPE: DNA
<213> ORGANISM: Mus musculus

<400> SEQUENCE: 42

```
atgaagttgc ctgttaggct gttggtgctg atgttctgga ttcctgcttc cagcagcgat    60
gttttgatga cccaaactcc actctccctg cctgtcagtc ttggagatca agcctccatc   120
tcttgcagat ctagtcagag ccttgtacat actactggaa acacctattt agaatggtat   180
ttgcagaaac caggccagtc tccaaagctc ctgatctaca agtttcccg ccgattttct   240
ggggtcccag acaggttcag tggcactgga tcagggacag atttcacact caggatcagc   300
agagtggagg ctgcggatct gggaatttat tactgctttc agggttcaca tattcctcct   360
acgttcggtg ctgggaccaa actggagcgg aaacgggctg atgctgcacc aactgtatcc   420
```

<210> SEQ ID NO 43
<211> LENGTH: 143
<212> TYPE: PRT
<213> ORGANISM: Mus musculus

<400> SEQUENCE: 43

```
Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Ser Ser Tyr Thr Ile His Trp Val Arg Gln Pro Pro Gly Arg Gly Leu
    50                  55                  60

Glu Trp Leu Gly Val Ile Trp Ala Gly Gly Ser Thr Asn Tyr Asn Ser
65                  70                  75                  80

Ala Leu Met Ser Arg Leu Arg Ile Ser Lys Asp Thr Ser Arg Ser Gln
                85                  90                  95

Val Phe Leu Lys Val Asn Ser Leu Gln Thr Asp Asp Ser Ala Ile Tyr
            100                 105                 110

Tyr Cys Ala Arg Asn Asp Phe Gly Tyr Gly Phe Ala Tyr Trp Gly Gln
        115                 120                 125

Gly Thr Leu Val Thr Val Ser Ala Ala Lys Thr Thr Ala Asn Arg
    130                 135                 140
```

```
<210> SEQ ID NO 44
<211> LENGTH: 140
<212> TYPE: PRT
<213> ORGANISM: Mus musculus

<400> SEQUENCE: 44

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Thr Thr Gly Asn Thr Tyr Leu Glu Trp Tyr Leu Gln Lys Pro
    50                  55                  60

Gly Gln Ser Pro Lys Leu Leu Ile Tyr Lys Val Ser Arg Arg Phe Ser
65                  70                  75                  80

Gly Val Pro Asp Arg Phe Ser Gly Thr Gly Ser Gly Thr Asp Phe Thr
                85                  90                  95

Leu Arg Ile Ser Arg Val Glu Ala Ala Asp Leu Gly Ile Tyr Tyr Cys
            100                 105                 110

Phe Gln Gly Ser His Ile Pro Pro Thr Phe Gly Ala Gly Thr Lys Leu
        115                 120                 125

Glu Arg Lys Arg Ala Asp Ala Ala Pro Thr Val Ser
    130                 135                 140

<210> SEQ ID NO 45
<211> LENGTH: 5
<212> TYPE: PRT
<213> ORGANISM: Mus musculus

<400> SEQUENCE: 45

Ser Tyr Thr Ile His
1               5

<210> SEQ ID NO 46
<211> LENGTH: 16
<212> TYPE: PRT
<213> ORGANISM: Mus musculus

<400> SEQUENCE: 46

Val Ile Trp Ala Gly Gly Ser Thr Asn Tyr Asn Ser Ala Leu Met Ser
1               5                   10                  15

<210> SEQ ID NO 47
<211> LENGTH: 9
<212> TYPE: PRT
<213> ORGANISM: Mus musculus

<400> SEQUENCE: 47

Asn Asp Phe Gly Tyr Gly Phe Ala Tyr
1               5

<210> SEQ ID NO 48
<211> LENGTH: 16
<212> TYPE: PRT
<213> ORGANISM: Mus musculus

<400> SEQUENCE: 48

Arg Ser Ser Gln Ser Leu Val His Thr Thr Gly Asn Thr Tyr Leu Glu
1               5                   10                  15
```

```
<210> SEQ ID NO 49
<211> LENGTH: 7
<212> TYPE: PRT
<213> ORGANISM: Mus musculus

<400> SEQUENCE: 49

Lys Val Ser Arg Arg Phe Ser
1               5

<210> SEQ ID NO 50
<211> LENGTH: 9
<212> TYPE: PRT
<213> ORGANISM: Mus musculus

<400> SEQUENCE: 50

Phe Gln Gly Ser His Ile Pro Pro Thr
1               5

<210> SEQ ID NO 51
<211> LENGTH: 43
<212> TYPE: DNA
<213> ORGANISM: Artificial
<220> FEATURE:
<223> OTHER INFORMATION: synthetic DNA

<400> SEQUENCE: 51
cactagagcc cccatacgcg tatggctgtc ctggtgctgt tcc          43

<210> SEQ ID NO 52
<211> LENGTH: 40
<212> TYPE: DNA
<213> ORGANISM: Artificial
<220> FEATURE:
<223> OTHER INFORMATION: synthetic DNA

<400> SEQUENCE: 52
ataagaatgc ggccgctcat ttacccggag agtgggagag              40

<210> SEQ ID NO 53
<211> LENGTH: 38
<212> TYPE: DNA
<213> ORGANISM: Artificial
<220> FEATURE:
<223> OTHER INFORMATION: synthetic DNA

<400> SEQUENCE: 53
tcctcaggtt gcctcacgcg tatgaagttg cctgttag                38

<210> SEQ ID NO 54
<211> LENGTH: 1383
<212> TYPE: DNA
<213> ORGANISM: Mus musculus

<400> SEQUENCE: 54
atggctgtcc tggtgctgtt cctctgcctg gttgcatttc caagctgtgt cctgtcccag      60
gtgcagctga aggagtcagg gcctggcctg gtggcgccct cacagagcct ttccatcact     120
tgcactgtct ctgggttttc attaagcagc tatactatac actgggttcg ccagcctcca     180
ggaaggggtc tggagtggct gggagtgata tggctggtg aagcacacaaa ctataattcg     240 gctctcatgt ctagactgcg catcagcaaa gacacctcca ggagccaagt tttcctaaaa     300
gtgaacagtc tgcaaactga tgactcagcc atatactact gtgccagaga tgacttcggc     360
tacgggtttg cttactgggg ccaagggact ctggtcactg tctctgcagc caaaacgaca     420
```

```
ccccatctg tctatccact ggcccctgga tctgctgccc aaactaactc catggtgacc      480
ctgggatgcc tggtcaaggg ctatttccct gagccagtga cagtgacctg gaactctgga      540
tccctgtcca gcggtgtgca caccttccca gctgtcctgc agtctgacct ctacactctg      600
agcagctcag tgactgtccc ctccagcacc tggcccagcg agaccgtcac ctgcaacgtt      660
gcccacccgg ccagcagcac caaggtggac aagaaaattg tgcccaggga ttgtggttgt      720
aagccttgca tatgtacagt cccagaagta tcatctgtct tcatcttccc cccaaagccc      780
aaggatgtgc tcaccattac tctgactcct aaggtcacgt gtgttgtggt agacatcagc      840
aaggatgatc ccgaggtcca gttcagctgg tttgtagatg atgtggaggt gcacacagct      900
cagacgcaac cccgggagga gcagttcaac agcactttcc gctcagtcag tgaacttccc      960
atcatgcacc aggactggct caatggcaag gagttcaaat gcagggtcaa cagtgcagct     1020
ttccctgccc ccatcgagaa aaccatctcc aaaaccaaag cagaccgaa ggctccacag      1080 gtgtacacca ttccacctcc caaggagcag atggccaagg ataaagtcag tctgacctgc     1140
atgataacag acttcttccc tgaagacatt actgtggagt ggcagtggaa tgggcagcca     1200
gcggagaact acaagaacac tcagcccatc atggacacag atggctctta cttcgtctac     1260
agcaagctca atgtgcagaa gagcaactgg gaggcaggaa atactttcac ctgctctgtg     1320
ttacatgagg gcctgcacaa ccaccatact gagaagagcc tctcccactc tccgggtaaa     1380
tga                                                                  1383

<210> SEQ ID NO 55
<211> LENGTH: 717
<212> TYPE: DNA
<213> ORGANISM: Mus musculus

<400> SEQUENCE: 55
atgaagttgc ctgttaggct gttggtgctg atgttctgga ttcctgcttc cagcagcgat        60
gttttgatga cccaaactcc actctccctg cctgtcagtc ttggagatca agcctccatc       120
tcttgcagat ctagtcagag ccttgtacat actactggaa acacctattt agaatggtat       180
ttgcagaaac caggccagtc tccaaagctc ctgatctaca aaatttcccg ccgatttttct      240 ggggtcccag acaggttcag tggcagtgga tcagggacag atttcacact caggatcagc       300
agagtggagg ctgcggatct gggaatttat tactgttttc agggttcaca tattcctcct       360
acgttcggtg ctgggaccaa actggagcgg aaacggctg atgctgcacc aactgtatcc        420
atcttcccac catccagtga gcagttaaca tctggaggtg cctcagtcgt gtgcttcttg       480
aacaacttct accccaaaga catcaatgtc aagtggaaga ttgatggcag tgaacgacaa       540
aatggcgtcc tgaacagttg gactgatcag gacagcaaag acagcaccta cagcatgagc       600
agcaccctca cgttgaccaa ggacgagtat gaacgacata cagctatac ctgtgaggcc        660 actcacaaga catcaacttc acccattgtc aagagcttca caggaatga gtgttaa           717

<210> SEQ ID NO 56
<211> LENGTH: 460
<212> TYPE: PRT
<213> ORGANISM: Mus musculus

<400> SEQUENCE: 56

Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30
```

-continued

Pro Ser Gln Ser Leu Ser Ile Thr Cys Thr Val Ser Gly Phe Ser Leu
        35                  40                  45

Ser Ser Tyr Thr Ile His Trp Val Arg Gln Pro Pro Gly Arg Gly Leu
50                  55                  60

Glu Trp Leu Gly Val Ile Trp Ala Gly Gly Ser Thr Asn Tyr Asn Ser
65                  70                  75                  80

Ala Leu Met Ser Arg Leu Arg Ile Ser Lys Asp Thr Ser Arg Ser Gln
                85                  90                  95

Val Phe Leu Lys Val Asn Ser Leu Gln Thr Asp Asp Ser Ala Ile Tyr
            100                 105                 110

Tyr Cys Ala Arg Asp Asp Phe Gly Tyr Gly Phe Ala Tyr Trp Gly Gln
        115                 120                 125

Gly Thr Leu Val Thr Val Ser Ala Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460

<210> SEQ ID NO 57
<211> LENGTH: 238
<212> TYPE: PRT
<213> ORGANISM: Mus musculus

<400> SEQUENCE: 57

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Thr Thr Gly Asn Thr Tyr Leu Glu Trp Tyr Leu Gln Lys Pro
    50                  55                  60

Gly Gln Ser Pro Lys Leu Leu Ile Tyr Lys Ile Ser Arg Arg Phe Ser
65                  70                  75                  80

Gly Val Pro Asp Arg Phe Ser Gly Ser Gly Ser Gly Thr Asp Phe Thr
                85                  90                  95

Leu Arg Ile Ser Arg Val Glu Ala Ala Asp Leu Gly Ile Tyr Tyr Cys
            100                 105                 110

Phe Gln Gly Ser His Ile Pro Pro Thr Phe Gly Ala Gly Thr Lys Leu
        115                 120                 125

Glu Arg Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 58
<211> LENGTH: 48
<212> TYPE: DNA
<213> ORGANISM: Artificial
<220> FEATURE:
<223> OTHER INFORMATION: synthetic DNA

<400> SEQUENCE: 58
gacagatggg ggtgtcgttt tagcgctaga gacagtgacc agagtccc        48

<210> SEQ ID NO 59
<211> LENGTH: 48
<212> TYPE: DNA
<213> ORGANISM: Artificial
<220> FEATURE:
<223> OTHER INFORMATION: synthetic DNA

<400> SEQUENCE: 59
gggactctgg tcactgtctc tagcgctaaa acgacacccc catctgtc        48

```
<210> SEQ ID NO 60
<211> LENGTH: 43
<212> TYPE: DNA
<213> ORGANISM: Artificial
<220> FEATURE:
<223> OTHER INFORMATION: synthetic DNA

<400> SEQUENCE: 60
cactgaccct aagcttatgg aatggagatg gatctttctc ttc          43

<210> SEQ ID NO 61
<211> LENGTH: 36
<212> TYPE: DNA
<213> ORGANISM: Artificial
<220> FEATURE:
<223> OTHER INFORMATION: synthetic DNA

<400> SEQUENCE: 61
ggctgttgtg ctagctgcag agacagtgac cagagt                  36

<210> SEQ ID NO 62
<211> LENGTH: 40
<212> TYPE: DNA
<213> ORGANISM: Artificial
<220> FEATURE:
<223> OTHER INFORMATION: synthetic DNA

<400> SEQUENCE: 62
attgcagcca ggagaattca tggacatgag gacccctgct              40

<210> SEQ ID NO 63
<211> LENGTH: 39
<212> TYPE: DNA
<213> ORGANISM: Artificial
<220> FEATURE:
<223> OTHER INFORMATION: synthetic DNA

<400> SEQUENCE: 63
ggtgcagcat ccgtacgttt tatttccaac tttgtcccc               39
```

ANTIBODY AGAINST HUMAN PROSTAGLANDIN E2 RECEPTOR EP4

CROSS-REFERENCE TO RELATED APPLICATIONS

This application is a Divisional of copending U.S. application Ser. No. 14/864,707, filed on Sep. 24, 2015, which is a Divisional of U.S. application Ser. No. 13/876,763, filed on Mar. 28, 2013, now U.S. Pat. No. 9,175,080, issued on Nov. 3, 2015, which is a 371 of International Application No. PCT/JP2011/072190, filed Sep. 28, 2011, which claims the benefit of priority from the prior Japanese Patent Application No. 2010-218158, filed on Sep. 29, 2010, the entire contents of all of which are incorporated herein by references.

TECHNICAL FIELD

The present invention relates to a monoclonal antibody against a human prostaglandin $E_2$ receptor subtype EP4.

BACKGROUND ART

Prostaglandin (PG), as well as thromboxane, is a physiologically active substance known as "prostanoid," and it is a lipid having a prostanoic acid skeleton. Prostanoid such as prostaglandin is biosynthesized from arachidonic acid that is released from a membrane phospholipid by the action of phospholipase A2. Prostaglandin is classified into groups A to J, based on differences in the types of an oxygen atom attached to the 5-membered ring thereof and a double bond. In addition, prostaglandin is classified into groups 1 to 3, based on the number of double bonds on the side chain of the prostanoic acid skeleton. For instance, prostaglandin E (PGE) includes $PGE_1$, $PGE_2$ and $PGE_3$, which are different from one another in terms of the number of double bonds on the prostanoic acid skeleton side chain.

Regarding PG, $PGH_2$ is generated from $PGG_2$ that is biosynthesized from arachidonic acid by the action of cyclooxygenase I (COX-I) or cyclooxygenase II (COX-II), and then, $PGD_2$, $PGE_2$, $PGF_2$, and the like are generated based on a difference in the cleavage of the bond between oxygen atoms. Thereafter, $PGA_2$, $PGC_2$ and the like are generated from $PGE_2$. Each PG generation reaction occurs by the action of a specific enzyme, and it is considered that such enzyme has tissue specificity and generates PG suitable for the function of each tissue.

Among various PGs, it is considered that PGE plays various important biological activities and that, through the mediation of its specific receptor, PGE is associated with regulation of the immune system, as well as vasodilatation, a decrease in blood pressure and uterine contraction. The $PGE_2$ receptor is a seven transmembrane G-protein-coupled receptor, as with other PG receptors. The $PGE_2$ receptor is abbreviated as EP, and it was revealed that EP has 4 types of subtypes (EP1, EP2, EP3 and EP4). Each subtype is associated with various phenomena in vivo. That is, EP1 is associated with an increase in intracellular $Ca^{2+}$ concentration; EP2 and EP4 are associated with an increase in cAMP level; and EP3 is associated with a decrease in cAMP level (Non Patent Literature 1). The 4 types of subtypes have high homology to one another in terms of protein structure.

It has been reported that when a low-molecular-weight compound antagonist having high selectivity to EP4 is administered to mice that had been induced to have experimental autoallergic encephalomyelitis or contact hypersensitivity, accumulation of both TH1 and TH17 cells in the regional lymph node is reduced, and the progression of the disease is suppressed (Non Patent Literature 2). It has been demonstrated that $PGE_2$ promotes production of IL-23 in dendritic cells, as a result of an increase in cAMP level mediated by the activation of EP4. In addition, it has also been demonstrated that, in TH17 cells, $PGE_2$ is involved in proliferation of the TH17 cells in coordination with IL-23. Thus, it has been demonstrated that an increase in cAMP level mediated by the activation of EP4 plays an important role for intracellular signaling in TH17 cells (Non Patent Literature 3). These reports suggest that the $PGE_2$ receptor antagonist, in particular, an EP4-selective antagonist be effective for the treatment of diseases caused by immunological abnormality, with which TH1 or TH17 is associated, such as multiple sclerosis, rheumatoid arthritis, inflammatory bowel disease and contact dermatitis (Non Patent Literature 2).

It has been reported that many types of cancer cells overexpress COX-II when compared with normal cells. Moreover, it has also been reported that $PGE_2$ acts on cancer tissues or tissues around the cancer tissues and is involved in the progression of cancer. For example, it has been described that $PGE_2$ is involved in infiltration of refractory inflammatory breast cancer cells or lung cancer cells into a metastatic tissue (Non Patent Literatures 4 and 5). Furthermore, it has been known that $PGE_2$ is associated with proliferation of non-small cell lung cancer cells, colon cancer cells, inflammatory breast cancer cells, B lymphocytes, prostatic cancer cells and melanoma, via EP4.

$PGE_2$ has been known to inhibit the function of NK cells which have an action to directly attack cancer cells. One of the mechanisms of $PGE_2$ to inhibit the activity of NK cells is an increase in intracellular cAMP level mediated by the activation of EP4 (Non Patent Literature 6). It has also been known that Treg cells that possibly suppress immunity to cancer are activated via EP4, and the possibility of decreasing the immune system to cancer cells in vivo has been suggested (Non Patent Literature 7). According to these reports, it is apparent that $PGE_2$ is important for the progression of cancer. Hence, clinical studies have been conducted using non-selective inhibitors to COX involved ingeneration of $PGE_2$. However, sufficient therapeutic results could not be obtained due to the side effects of the inhibitors. The $PGE_2$ receptor antagonist, in particular, an EP4-selective antagonist directly suppresses proliferation of cancer cells and boosts the host immune system to cancer. Accordingly, it is anticipated that an antibody that selectively binds to the EP4 receptor will be effective for the treatment of various types of cancers such as breast cancer, colon cancer, lung cancer, prostatic cancer, skin cancer and B-lymphoma.

Conventionally, non-specific COX inhibitors have been applied for the relief of pain. However, it has been known that such non-specific inhibitors cause side effects such as heartburn, indigestion, nausea, abdominal distension, diarrhea, gastralgia, peptic ulcer or gastrointestinal bleeding. In recent years, COX-II selective inhibitors (e.g. celecoxib and rofecoxib) have been developed for the purpose of treating pain. However, it has been suggested that such COX-II selective inhibitors develop severe cardiovascular disorder in specific patients, and thus it has been desired to develop a drug for relieving pain based on a different mode of action. Among PGs generated by COX, $PGE_2$ is known to enhance the hypersensitivity of pain sense. It has been demonstrated by multiple animal experiments that, among $PGE_2$ receptors, EP4 is particularly associated with the enhancement of the hypersensitivity of pain sense. For example, it has been known that the expression of EP4 is enhanced in the dorsal root ganglion (GRG) in a rat model of inflammatory pain, and that a comparatively selective EP4 antagonist (AH23848) relieves the sensitivity of pain in the aforementioned model (Non Patent Literature 8). Moreover, in an analysis using EP4 knock-out mice as well, the same results could be obtained (Non Patent Literature 9). These reports suggest that a pharmaceutical product for selectively blocking the function of EP4 be effective for the treatment of diseases associated with immunological abnormality, cancer and pain, while having fewer side effects.

As methods for selectively blocking the function of EP4, several low-molecular-weight compound antagonists have been reported. However, none of such compound antagonists have been successful as pharmaceutical products. Such low-molecular-weight compound antagonists would be improved in terms of binding selectivity to $PGE_2$ receptor subtypes (EP1-4) or alleviation of binding affinity for thromboxane or other prostanoid receptors. It is concerned that the same side effects as those of COX inhibitors are generated unless sufficient receptor selectivity is secured.

An antibody selectively binding to the EP4 receptor is expected to have higher selectivity than low-molecular-weight compounds. Furthermore, since an antibody drug generally has a longer half-life in blood than low-molecular-weight compounds, it is expected to have drug effects for a long period of time by a single administration. Such antibody drug is effective for chronic diseases (e.g. rheumatoid arthritis, colitis, cancer, etc.).

In general, as a main action mechanism of an antibody drug directed at a membrane protein (receptor), the antibody has recognized cells expressing the protein, and has then removed the cells based on complement-dependent cytotoxicity (CDC) and antibody-dependent cell-mediated cytotoxicity (ADCC). However, since CDC or ADCC is associated with activation of inflammatory cells such as macrophage, such antibody drug is not necessarily suitable for the treatment of diseases caused by immunological abnormality or pain. Accordingly, when a monoclonal antibody capable of selectively inhibiting EP4 is applied for the treatment of diseases caused by immunological abnormality or pain, it is desirably a functional antibody that depends on neither CDC nor ADCC. That is to say, an antibody for selectively blocking EP4-dependent intracellular signaling is desirable. To date, Japanese Patent No. 3118460 (Patent Literature 1) discloses a method for obtaining an antibody against EP4. However, there have not yet been any reports regarding a specific antibody that EP4-specifically suppresses the function of EP4 at a low dose and binds to neither EP1, EP2 nor EP3. In addition, it has been known that it is difficult to obtain a functional antibody against a seven-transmembrane receptor by the general method for obtaining a monoclonal antibody described in Japanese Patent No. 3118460.

CITATION LIST

Patent Literature

Patent Literature 1: Japanese Patent No. 3118460
Non Patent Literature
Non Patent Literature 1: Sugimoto et al., J. Biol. Chem., 282, 11613-11617, 2007
Non Patent Literature 2: Yao et al., Nat. Med., 15, 633-640, 2009
Non Patent Literature 3: Sakata et al., J Pharmacol Sci., 112(1): 1-5. 2010

Non Patent Literature 4: Robertson FM Cancer. 2010 Jun. 1; 116 (11 Suppl): 2806-14.
Non Patent Literature 5: Martinet L. Biochem Pharmacol. 2010 Sep. 15; 80(6): 838-45.
Non Patent Literature 6: Sharma SD, Mol Cancer Ther. 2010 March; 9(3): 569-80.
Non Patent Literature 7: Sharma S et al., Cancer Res. 2005 Jun. 15; 65(12): 5211-20
Non Patent Literature 8: Lin C.-R. et al., J Pharmacology and Experimental Therapeutics 2006, 319: 3 (1096-1103)
Non Patent Literature 9: Popp L. et al., European Journal of Pain. 2009, 13: 7 (691-703)

SUMMARY OF INVENTION

Technical Problem

It is an object of the present invention to provide an antibody against a human $PGE_2$ receptor subtype EP4, which is useful as a therapeutic agent for diseases caused by immunological abnormality, tumor and pain, a pharmaceutical composition comprising the aforementioned anti-human EP4 antibody, and the like.

Solution to Problem

The present inventors have attempted to produce a monoclonal antibody against a human $PGE_2$ receptor subtype EP4. As a result, the inventors have succeeded in obtaining an antibody that specifically binds to the extracellular domain of the subtype EP4 and suppresses the function of EP4 (e.g. the function to increase intracellular cAMP level), thereby completing the present invention.

Specifically, the present invention includes the following (1) to (21).

(1) An antibody that binds to the extracellular domain of a $PGE_2$ receptor subtype EP4 and inhibits the function of EP4, or a functional fragment thereof.

(2) The antibody according to (1) above or a functional fragment thereof, wherein the antibody is a monoclonal antibody.

(3) The antibody according to (2) above or a functional fragment thereof, wherein the antibody is produced from hybridomas with the international depositary accession Nos. FERM BP-11402 and FERM BP-11403.

(4) The antibody according to any one of (1) to (3) above or a functional fragment thereof, wherein the function of EP4 is to increase the intracellular cAMP level.

(5) The antibody according to any one of (1) to (3) above or a functional fragment thereof, wherein the antibody specifically binds to the extracellular domain of EP4, and comprises any one of the following (A), (B), or (C), with regard to the amino acid sequences of its complementarity determining regions 1-3 (CDR1-3): (A) the antibody has
heavy chain CDR1 comprising the amino acid sequence shown in SEQ ID NO: 5,
heavy chain CDR2 comprising the amino acid sequence shown in SEQ ID NO: 6,
heavy chain CDR3 comprising the amino acid sequence shown in SEQ ID NO: 7,
light chain CDR1 comprising the amino acid sequence shown in SEQ ID NO: 8,
light chain CDR2 comprising the amino acid sequence shown in SEQ ID NO: 9, and
light chain CDR3 comprising the amino acid sequence shown in SEQ ID NO: 10;

(B) the antibody has
heavy chain CDR1 comprising the amino acid sequence shown in SEQ ID NO: 15,
heavy chain CDR2 comprising the amino acid sequence shown in SEQ ID NO: 16,
heavy chain CDR3 comprising the amino acid sequence shown in SEQ ID NO: 17,
light chain CDR1 comprising the amino acid sequence shown in SEQ ID NO: 18,
light chain CDR2 comprising the amino acid sequence shown in SEQ ID NO: 19, and
light chain CDR3 comprising the amino acid sequence shown in SEQ ID NO: 20; or
(C) the antibody has
heavy chain CDR1 comprising the amino acid sequence shown in SEQ ID NO: 45,
heavy chain CDR2 comprising the amino acid sequence shown in SEQ ID NO: 46,
heavy chain CDR3 comprising the amino acid sequence shown in SEQ ID NO: 47,
light chain CDR1 comprising the amino acid sequence shown in SEQ ID NO: 48,
light chain CDR2 comprising the amino acid sequence shown in SEQ ID NO: 49, and
light chain CDR3 comprising the amino acid sequence shown in SEQ ID NO: 50.

(6) The antibody according to any one of (1) to (5) above or a functional fragment thereof, wherein the antibody specifically binds to the extracellular domain of EP4, and comprises any one of the following (a), (b), or (c), with regard to the amino acid sequences of its heavy chain variable region and light chain variably region:
(a) the antibody has a heavy chain variable region comprising the amino acid sequence shown in SEQ ID NO: 2, and a light chain variable region comprising the amino acid sequence shown in SEQ ID NO: 4;
(b) the antibody has a heavy chain variable region comprising the amino acid sequence shown in SEQ ID NO: 12, and a light chain variable region comprising the amino acid sequence shown in SEQ ID NO: 14; or
(c) the antibody has a heavy chain variable region comprising the amino acid sequence shown in SEQ ID NO: 43, and a light chain variable region comprising the amino acid sequence shown in SEQ ID NO: 44.

(7) An antibody that binds to the extracellular domain of EP4 and inhibits the function of EP4, or a functional fragment thereof, wherein the antibody binds to the same epitope, to which the antibody according to any one of (3) to (6) above binds.

(8) The antibody according to any one of (1) to (7) above or a functional fragment thereof, wherein the antibody is a humanized antibody or a chimeric antibody.

(9) The antibody according to any one of (1) to (7) above or a functional fragment thereof, wherein the antibody is a human antibody.

(10) The antibody according to any one of (1) to (9) above or a functional fragment thereof, wherein the antibody is an antibody fragment, a single-chain antibody, or a diabody.

(11) A nucleic acid encoding the heavy chain variable region or light chain variable region of the antibody according to (5) or (6) above, wherein the nucleic acid is shown in SEQ ID NO: 1, SEQ ID NO: 3, SEQ ID NO: 11, SEQ ID NO: 13, SEQ ID NO: 41, or SEQ ID NO: 42.

(12) A vector comprising the nucleic acid according to (11) above.

(13) A cell into which the vector according to (12) above is introduced.

(14) A pharmaceutical composition comprising the antibody according to any one of (1) to (10) above or a functional fragment thereof.

(15) The pharmaceutical composition according to (14) above, which is used for prevention or treatment of a disease that develops or progresses due to abnormality in the function of EP4.

(16) The pharmaceutical composition according to (15) above, wherein the disease to be treated is an immunological disease.

(17) The pharmaceutical composition according to (15) above, wherein the disease to be treated is tumor.

(18) The pharmaceutical composition according to (15) above, wherein the disease to be treated is pain.

(19) An antibody-immobilized carrier, wherein the anti-EP4 antibody according to any one of (1) to (10) above or a functional fragment thereof is immobilized on a carrier.

(20) The antibody-immobilized carrier according to (19) above, which is used such that blood comprising EP4-expressing cells is allowed to come into contact with the carrier, and the EP4-expressing cells are then removed from the body fluid.

(21) A kit for measuring the expression level of EP4 on a cell surface, which comprises the anti-EP4 antibody according to any one of (1) to (10) above.

Advantageous Effects of Invention

According to the present invention, an antibody that EP4-specifically suppresses the function of EP4 has been provided for the first time.

According to the present invention, the EP4-related medicament of the present invention is able to treat or prevent EP4-related immunological diseases, tumor and pain. In particular, using the antibody of the present invention having higher binding selectivity to a subtype EP4 than low-molecular-weight compounds, therapeutic effects with fewer side effects can be provided.

Using the antibody-immobilized carrier of the present invention, EP4-expressing cells can be selectively removed from the blood of a patient affected with cancer, autoimmune disease or the like.

Using the kit for measuring the expression level of EP4 of the present invention, EP4-expressing cells can be detected in the blood of a patient affected with cancer, autoimmune disease or the like, and then, using the detected cells, the condition of the disease can be evaluated.

BRIEF DESCRIPTION OF DRAWINGS

FIG. 1 shows the results of flow cytometry, which analyzed the binding of a mouse isotype control antibody, NBG016-mAb14 and NBG016-mAb21 to the parent Flp-In-CHO cell line and the CHO cell line stably expressing human EP4.

FIG. 2 shows the results of flow cytometry, which analyzed the binding of a mouse isotype control antibody and NBG016-mAb9 to the parent Flp-In-CHO cell line and the CHO cell line stably expressing human EP4.

FIG. 3 shows the results obtained by analyzing the suppressive effects of a mouse isotype control antibody, NBG016-mAb14 and NBG016-mAb21 on $PGE_2$-induced increase in cAMP level.

FIG. 4 shows the results obtained by analyzing the suppressive effects of a mouse isotype control antibody and NBG016-mAb9 on $PGE_2$-induced increase in cAMP level.

FIG. 5 shows the results of flow cytometry, which analyzed the binding of NBG016-mAb14 to 293FT cells, into which each of human EP1-4 and mouse EP1-4 genes had been introduced.

FIG. 6 shows the results of flow cytometry, which analyzed the binding of NBG016-mAb9 to 293FT cells, into which each of human EP1-4 and mouse EP1-4 genes had been introduced.

FIG. 7 shows the results of flow cytometry, which analyzed the binding of a mouse isotype control antibody, NBG016-mAb14 and NBG016-mAb21 to lymphocyte subsets in human peripheral blood.

FIG. 8 shows the results of flow cytometry, which analyzed the binding of a mouse isotype control antibody and NBG016-mAb9 to lymphocyte subsets in human peripheral blood.

FIG. 9 shows the results of immunostaining the human monocytic THP1 cell line treated with PMA, using an anti-EP4 antibody.

FIG. 10 shows the results of flow cytometry, which analyzed the binding of a culture supernatant of antibody gene-non-introduced cells and a culture supernatant of recombinant antibody NBG016-mAb9 gene-expressing cells to the parent Flp-In-CHO cell line and the CHO cell line stably expressing human EP4.

FIG. 11 shows the results of flow cytometry, which analyzed the binding of a mouse isotype control antibody, the recombinant antibody NBG016-mAb14 and the recombinant antibody NBG016-mAb21 to the parent Flp-In-CHO cell line and CHO cell line stably expressing human EP4.

FIG. 12(A) shows the results of flow cytometry, which analyzed the binding of a mouse isotype control antibody and the mouse IgG1 antibody NBG016-mAb21 to the parent Flp-In-CHO cell line and the CHO cell line stably expressing human EP4. FIG. 12(B) shows the results obtained by analyzing the suppressive effects of a mouse isotype control antibody and the mouse IgG1 antibody NBG016-mAb21 on $PGE_2$-induced increase in cAMP level.

FIG. 13 shows the results of flow cytometry, which analyzed the binding of a culture supernatant of antibody gene-non-introduced cells, a culture supernatant of human chimeric antibody NBG016-mAb 14 gene-expressing cells, and a culture supernatant of human chimeric antibody NBG016-mAb21 gene-expressing cells, to the parent Flp-In-CHO cell line and the CHO cell line stably expressing human EP4.

DESCRIPTION OF EMBODIMENTS

The present invention relates to an antibody that binds to the extracellular domain of a human $PGE_2$ receptor subtype EP4 and suppresses the function of EP4, or a functional fragment thereof, and a medicament comprising the antibody or a functional fragment thereof.

Definition of EP4 Protein

As an EP4 protein serving as an antigen in the present invention, a recombinant protein prepared from cDNA encoding the EP4 protein or the like can be used. Alternatively, a suitable cell that expresses EP4 on the surface thereof may be used as an antigen. A nucleic acid sequence encoding a human EP4 protein can be searched in published database such as GenBank (e.g. Accession No.: NM_000958). Using a probe, a primer pair for PCR amplification, or the like produced based on the aforementioned gene sequence or the like, DNA (e.g. cDNA) encoding EP4 can be prepared from a suitable DNA library. Alternatively, total cDNA can be prepared by an artificial DNA synthesis method. As an example, an amino acid sequence corresponding to human EP4 is shown in SEQ ID NO: 21. Human EP4 has been known to have various types of variants such as amino acid substituted variants, as well as that shown in SEQ ID NO: 21. The term "human EP4" is used in the present invention to include the aforementioned variants, as long as it has the function of EP4.

The intracellular and extracellular domains of human EP4 are considered to correspond to the below-mentioned portions in the amino acid sequence shown in SEQ ID NO: 21. The left term indicates amino acid numbers, and the right term indicates the relevant domain. It is to be noted that the boundary between individual domains may include some range (1 to 5 amino acid residues, preferably 1 to 3 amino acid residues, and more preferably 1 or 2 amino acid residues).

1 to 19: N-terminal domain
44 to 54: Intracellular first loop domain
80 to 96: Extracellular first loop domain
116 to 135: Intracellular second loop domain
161 to 184: Extracellular second loop domain
212 to 267: Intracellular third loop domain
296 to 312: Extracellular third loop domain
333 to 488: C-terminal domain Definition of Antibody or Functional Antibody The antibody of the present invention that suppresses the function of EP4 includes a monoclonal antibody and a polyclonal antibody. The functional fragments of the present antibody include antibody fragments such as Fab or F(ab')$_2$, and single-chain antibodies. As far as it is a polypeptide (or a polypeptide complex) that constitutes a part of an antibody and suppresses the function of EP4, all types of polypeptides are included in the scope of the present invention.

Definition of Functional Antibody Specific to EP4 and Evaluation Method therefor Examples of the function of EP4 include an increase in intracellular cAMP level and activation of Phosphoinositide 3-kinase (P13K). It has been known that these intracellular changes regulate proliferation of cancer cells, proliferation of T lymphocytes, and generation of cytokines. The specific binding of the antibody of the present invention to the extracellular domain of a human $PGE_2$ receptor subtype EP4 can be proved as follows. A nucleic acid sequence encoding a human EP4 protein is inserted into an expression vector, and the vector is then introduced into suitable host cells (e.g. mammalian cells such as CHO cells, yeast cells, insect cells, etc.). Non-destructive, EP4-expressing host cells or EP4-non-expressing host cells, which do not comprise an insertion, deletion, substitution or the like of amino acids, are allowed to come into contact with the antibody of the present invention, and they are allowed to react with each other for a certain period of time. After excessive antibody has been washed off, the cells are subjected to ELISA, RIA or flow cytometry, so that the amount of antibody binding to the cells is measured. If a larger amount of the antibody of the present invention binds to the EP4-expressing host cells than to the non-expressing host cells, the results can show the specific binding of the antibody of the present invention to the extracellular domain of EP4. Moreover, there is constructed an expression vector into which a nucleic acid sequence encoding a human- or mouse-derived EP1, EP2, EP3 or EP4 protein has been inserted. Then, receptor-expressing host cells are analyzed in the same manner as described above. Thus, it can be demonstrated that the antibody of the present invention binds to human EP4-expressing host cells more strongly than to other receptor-expressing cells, and preferably that the binding of the antibody of the present invention to cells that express receptors other than human EP4 cannot be found.

The fact that the antibody of the present invention is an antibody that inhibits the function of EP4 can be explained as follows. A nucleic acid sequence encoding a human EP4 protein is inserted into an expression vector, and the vector is then introduced into suitable host cells (e.g. mammalian cells such as CHO cells, yeast cells, insect cells, etc.). The human EP4-expressing host cells are allowed to come into contact with the antibody with a concentration of 0.01 to 30 μg/mL, and then, the cells are further allowed to come into contact with $PGE_2$ with a concentration of $10^{-12}$ to $10^{-6}$ M. Thereafter, an increase in intracellular cAMP level is measured by a suitable method. When the antibody of the present invention is added to the cells, it is able to suppress a $PGE_2$-induced increase in cAMP level in a dose-dependent manner.

Moreover, the present antibody with a concentration of 0.01 to 10 μg/mL is allowed to come into contact with a cell line that naturally expresses human EP4 (e.g. human macrophage cells), and $PGE_2$ with a concentration of $10^{-12}$ to $10^{-6}$ M is further allowed to come into contact with the cells. Thereafter, the generation of cytokines or chemokines by inflammatory stimulus (e.g. lipopolysaccharide (LPS)) is examined. It has been known that $PGE_2$ suppresses the generation of cytokines by LPS stimulus through the mediation of EP4 or EP2. The activity of the antibody of the present invention to inhibit the function of EP4 can be evaluated using, as an indicator, the fact that the present antibody recovers the suppression of cytokine generation by $PGE_2$, through the mediation of EP4. Likewise, the activity of the present antibody to inhibit the function of EP4 can also be evaluated using, as an indicator, the effect of the present antibody to inhibit the generation of IL-23 enhanced by $PGE_2$ from human peripheral blood dendritic cells.

Furthermore, when a cancer cell line derived from human bladder cancer, breast cancer, cervical cancer, colorectal cancer, esophageal cancer, cancer of the head and neck, skin cancer, lung cancer, oral cancer, prostatic cancer or multiple myeloma (e.g. MDA-MB-231 cells, HCA-7 cells, HT-29 cells, etc.) is allowed to come into contact with $PGE_2$, the proliferative activity of the cells is enhanced. After the antibody of the present invention has previously been allowed to come into contact with these cells, the activity of the present antibody to inhibit the function of $PGE_2$ can be evaluated using, as an indicator, the fact that an increase in the proliferative activity of the cells caused by $PGE_2$ is reduced.

The antibody of the present invention binds only to human EP4 and does not react with mouse EP4. Accordingly, it is difficult to evaluate by animal tests the drug effects of the antibody of the present invention regarding immunological abnormality or pain. On the other hand, regarding the antitumor effects of the present antibody, cells highly expressing EP4, which have been established from the above-mentioned human cancer tissues, are grafted into immunodeficient mice in an amount of $10^6$ to $10^7$ cells per mouse. Immediately after the graft of the cells, the antibody of the present invention is intraperitoneally or subcutaneously administered to the mice at a dose of 0.1 to 0.5 mg/mouse. When compared with an isotype control antibody administration group, tumor formation or metastasis frequency can be significantly reduced in the administration group, to which the antibody of the present invention has been administered. Thus, it can be demonstrated that the antibody of the present invention has an antitumor effect.

Detailed Definition of the Antibody of the Present Invention

Examples of the antibody of the present invention and a functional fragment thereof include: monoclonal antibodies produced from hybridomas having international depositary accession numbers FERM BP-11402 (NBG016-mAb14) and FERM BP-11403 (NBG016-mAb21); and monoclonal antibodies prepared by the methods described in the aftermentioned Examples.

Moreover, other examples of the antibody of the present invention and a functional fragment thereof include: an antibody which have a heavy chain variable region comprising the amino acid sequence shown in SEQ ID NO: 2 and a light chain variable region comprising the amino acid sequence shown in SEQ ID NO: 4; an antibody which have a heavy chain variable region comprising the amino acid sequence shown in SEQ ID NO: 12 and a light chain variable region comprising the amino acid sequence shown in SEQ ID NO: 14; an antibody which have a heavy chain variable region comprising the amino acid sequence shown in SEQ ID NO: 43 and a light chain variable region comprising the amino acid sequence shown in SEQ ID NO: 44; an antibody which have a heavy chain comprising the amino acid sequence shown in SEQ ID NO: 23 and a light chain comprising the amino acid sequence shown in SEQ ID NO: 25; an antibody which have a heavy chain comprising the amino acid sequence shown in SEQ ID NO: 27 and a light chain comprising the amino acid sequence shown in SEQ ID NO: 29; an antibody which have a heavy chain comprising the amino acid sequence shown in SEQ ID NO: 56 and a light chain comprising the amino acid sequence shown in SEQ ID NO: 57; functional fragments of the aforementioned antibodies; an antibody consisting of a heavy chain and/or a light chain having an amino acid sequence(s) comprising a deletion, substitution or addition of one or several amino acids, with respect to the amino acid sequence(s) of a heaving chain and/or a light chain that constitute(s) the aforementioned antibodies; and functional fragments thereof that suppress the function of EP4.

Definition of Epitope Identical to that of the Antibody of the Present Invention Further, a particularly preferred example of the antibody of the present invention and a functional fragment thereof is an antibody having an epitope overlapped with (or identical to) the epitope of any one of the monoclonal antibodies isolated in Examples. In the present invention, such an antibody is referred to as an antibody binding to substantially the same site. Whether or not two antibodies bind to substantially the same site can be determined, for example, by performing a competition experiment. Specifically, when the binding of the anti-EP4 antibody to EP4 described in Examples is competitively inhibited by a secondary anti-EP4 antibody, it is determined that the primary antibody and the secondary antibody bind to substantially the same antigenic site. Thus, an antibody binding to substantially the same site as the EP4 binding site of the antibody isolated in Examples, which has an action to inhibit the function of EP4, is included in the present invention.

Method for Obtaining the Antibody of the Present Invention

The anti-EP4 antibody of the present invention may be a monoclonal antibody, a polyclonal antibody, or a functional fragment thereof. Of these, a monoclonal antibody is preferable because it can stably produce an antibody that is homogenous as a pharmaceutical composition. The term "monoclonal" suggests the properties of an antibody obtained from a group of substantially homogenous antibodies. Thus, this term is not used to mean that the antibody is produced by a specific method. For instance, the monoclonal antibody used in the present invention may be produced, for example, by a hybridoma method (Kohler and Milstein, Nature 256: 495 (1975)) or a recombination method (U.S. Pat. No. 4,816,567). The monoclonal antibody used in the present invention may also be isolated from a phage antibody library (Clackson et al., Nature 352: 624-628 (1991); Marks et al., J. Mol. Biol. 222: 581-597 (1991)). Particular examples of the monoclonal antibody used in the present invention include: a "chimeric" antibody (immunoglobulin), in which a portion of the heavy chain and/or light chain of the monoclonal antibody used in the present invention is derived from specific species or a specific antibody class or subclass, and a remaining portion of the chain(s) is derived from another antibody class or subclass; an antibody variant; and a functional fragment thereof (U.S. Pat. No. 4,816,567; Morrison et al., Proc. Natl. Acad. Sci. USA 81: 6851-6855 (1984)).

When the antibody of the present invention is a polyclonal antibody, it can be prepared by injecting a mixture of an immunogen and an adjuvant into, for example, a mammalian host animal. In general, an antigen used as an immunogen and/or an adjuvant are injected into the subcutis of a host animal several times. Examples of such an adjuvant include a Complete Freund's adjuvant and monophosphoryl lipid A-trehalose dicorynomycolate (MPL-TDM). After completion of the treatment with an immunogen, a desired antibody against EP4, which has been generated in blood, can be obtained using, as indicators, EP4-binding specificity and an action to suppress the function of EP4.

On the other hand, when the antibody of the present invention is a monoclonal antibody, it can be prepared, for example, by a hybridoma method.

This method includes the following 4 steps of: (i) immunizing a host animal or host animal-derived cells with a human EP4 protein; (ii) recovering monoclonal antibody-secreting (or potentially secreting) lymphocytes; (iii) fusing the lymphocytes with immortalized cells; and (iv) selecting cells that secrete a desired monoclonal antibody. A mouse, a rat, a guinea pig, a hamster, or another suitable host animal is selected as an animal to be immunized, and then, an immunogen is injected into the selected animal.

After completion of the immunization, lymphocytes obtained from the host animal are fused with an immortalized cell line using a fusion agent such as polyethylene glycol, so as to establish hybridoma cells. As fusion cells, a rat or mouse myeloma cell line is used, for example. After completion of the cell fusion, the cells are allowed to grow in a suitable medium that contains one or more substrates that inhibit the growth or survival of unfused lymphocytes and immortalized cell line. According to an ordinary technique, parent cells that lack the enzyme, hypoxanthine-guanine phosphoribosyl transferase (HGPRT or HPRT), are used. In this case, hypoxanthine, aminopterin and thymidine are added to a medium that inhibits the growth of the HGPRT-deficient cells and allows the growth of hybridomas (HAT medium). From the thus obtained hybridomas, those producing desired antibodies can be selected, and then, a monoclonal antibody of interest can be obtained from a medium in which the hybridomas grow according to an ordinary method.

The thus prepared hybridomas are cultured in vitro, or are cultured in vivo in the ascites of a mouse, a rat, a guinea pig, a hamster, etc., so that an antibody of interest can be prepared from a culture supernatant or ascites.

The nucleic acid of the present invention encodes the heavy chain variable region or light chain variable region of the antibody of the present invention. The nucleic acid of the present invention that encodes the heavy chain variable region or light chain variable region may be inserted into a vector, and the vector may be then expressed in cells.

The type of the vector is not particularly limited, and it may be selected, as appropriate, depending on the type of a host cell into which the vector is to be introduced, and the like. Also, the vector may be introduced into host cells suitable for the expression of an antibody (e.g. mammalian cells such as CHO cells, yeast cells, insect cells, etc.), so that a recombinant antibody can be prepared.

Definition of the Chimeric Antibody of the Present Invention and Production Method thereof The embodiment of the anti-EP4 antibody of the present invention includes a genetically recombinant antibody. The type of such a genetically recombinant antibody is not particularly limited. Examples of the genetically recombinant antibody include a chimeric antibody, a humanized antibody and a human antibody. The term "chimeric antibody" is used herein to mean an antibody in which an animal-derived variable region is ligated to a different animal-derived constant region, and particularly, an antibody in which a mouse-derived antibody variable region is ligated to a human-derived antibody constant region (see Proc. Natl. Acad. Sci. U.S.A., 81, 6851-6855, (1984), etc.). When a chimeric antibody is produced, an antibody comprising such a ligation of a variable region to a constant region can be easily constructed according to a genetic recombination technique well known to a person skilled in the art. Herein, with regard to mouse-derived antibody variable regions, the heavy chain variable region preferably consists of the amino acid sequence shown in, for example, SEQ ID NO: 2 or SEQ ID NO: 12, and the light chain variable region preferably consists of the amino acid sequence shown in, for example, SEQ ID NO: 4 or SEQ ID NO: 14. The chimeric heavy chain or chimeric light chain of the present invention is inserted into a vector. The type of a vector is not particularly limited. The vector may be selected, as appropriate, depending on the type of a host cell into which it is to be introduced, and the like. Also, the vector may be introduced into host cells suitable for the expression of an antibody (e.g. mammalian cells such as CHO cells, yeast cells, insect cells, etc.), so that a recombinant antibody can be prepared.

Definition of the Humanized Antibody of the Present Invention and Production Method thereof The chimeric antibody of the present invention includes a human(ized) antibody. The humanized antibody is an antibody in which a framework region is derived from a human and CDR is a mouse-derived region. The humanized antibody can be produced by first grafting CDR from the variable region of a mouse antibody into a human variable region to reconstitute heavy chain and light chain variable regions, and then ligating the thus humanized, reconstituted human variable region to a human constant region. Such a method for producing a humanized antibody is well known in the present technical field (see, for example, Nature, 321, 522-525 (1986); J. Mol. Biol., 196, 901-917 (1987); Queen C et al., Proc. Natl. Acad. Sci. USA, 86: 10029-10033 (1989)). Herein, the type of a mouse-derived CDR sequence used for the anti-EP4 antibody of the present invention is not limited. For instance, examples of the heavy chain CDR1 to 3 include the amino acid sequences shown in SEQ ID NOS: 5 to 7, and examples of the light chain CDR1 to 3 include the amino acid sequences shown in SEQ ID NOS: 8 to 10 and the amino acid sequences shown in SEQ ID NOS: 18 to 20.

In order to allow a humanized antibody heavy chain or a humanized antibody light chain to express in host cells, the humanized antibody heavy chain or the humanized antibody light chain may be inserted into a vector. The type of such a vector is not particularly limited, and it can be selected, as appropriate, depending on the type of a host cell into which it is to be introduced, and the like. Also, the vector may be introduced into host cells suitable for the expression of an antibody (e.g. mammalian cells such as CHO cells, yeast cells, insect cells, etc.), and an antibody is reconstituted in the host cells, so that a recombinant antibody can be prepared.

Definition of the Human Antibody of the Present Invention and Production Method thereof The human antibody (complete human antibody) is an antibody in which a hyper variable region that is an antigen-binding site of a variable region, a remaining region of the variable region, and a constant region have the same structures as those of a human antibody. However, the hyper variable region may also be derived from another animal. Such a human antibody can be easily produced by a person skilled in the art according to a known technique. The human antibody can be obtained, for example, by a method using a human antibody-producing mouse having a human chromosomal fragment comprising the heavy chain and light chain genes of a human antibody (see Tomizuka, K. et al., Nature Genetics, (1997) 16, 133-143; Kuroiwa, Y. et. al., Nuc. Acids Res., (1998) 26, 3447-3448; Yoshida, H. et. al., Animal Cell Technology: Basic and Applied Aspects, (1999) 10, 69-73 (Kitagawa, Y., Matsuda, T. and Iijima, S. eds.), Kluwer Academic Publishers; Tomizuka, K. et. al., Proc. Natl. Acad. Sci. USA, (2000) 97, 722-727, etc.), or by a method of obtaining a phage display-derived human antibody selected from a human antibody library (Wormstone, I. M. et. al, Investigative Ophthalmology & Visual Science., (2002) 43(7), 2301-8; Carmen, S. et. al., Briefings in Functional Genomics and Proteomics, (2002) 1(2), 189-203; Siriwardena, D. et. al., Opthalmology, (2002) 109(3), 427-431, etc.).

Functional Fragment of the Antibody of the Present Invention

The functional fragment of the antibody of the present invention means a partial region of the anti-EP4 antibody. Examples of such a functional fragment include Fab, Fab', $F(ab')_2$, Fv (a variable fragment of antibody), a single-chain antibody (a heavy chain, a light chain, a heavy chain variable region, a light chain variable region, etc.), scFv, a diabody (a scFv dimer), dsFv (a disulfide-stabilized variable region), and a peptide comprising CDR as at least a portion thereof. Fab is an antibody fragment having antigen-binding activity obtained by digesting an antibody molecule with the protease papain, wherein about an N-terminal half of the heavy chain binds to the light chain as a whole via a disulfide bond.

Fab can be produced by digesting an antibody molecule with papain to obtain a fragment thereof. Fab can also be produced by, for example, constituting a suitable expression vector into which DNA encoding the Fab has been inserted, then introducing the vector into suitable host cells (e.g. mammalian cells such as CHO cells, yeast cells, insect cells, etc.), and then allowing it to express in the cells.

$F(ab')_2$ is an antibody fragment having antigen-binding activity obtained by digesting an antibody molecule with the protease pepsin, which is slightly greater than Fab that binds to another Fab via a disulfide bond at hinge region. $F(ab')_2$ can be obtained by digesting an antibody molecule with the protease pepsin, or it can also be produced by binding the after-mentioned Fab to another Fab via a thioether bond or a disulfide bond. Alternatively, $F(ab')_2$ can also be produced according to a genetic engineering method, as with Fab.

Fab' is an antibody fragment having antigen-binding activity obtained by cleaving the disulfide bond at hinge region of the above-described $F(ab')_2$. Fab' can also be produced according to a genetic engineering method, as in the case of Fab and the like.

scFv is an antibody fragment having antigen-binding activity that is a VH-linker-VL or VL-linker-VH polypeptide, wherein a single heavy chain variable region (VH) is ligated to a single light chain variable region (VL) using a suitable peptide linker. Such scFv can be produced by obtaining cDNAs encoding the heavy chain variable region and light chain variable region of an antibody and then treating them according to a genetic engineering method.

Diabody is an antibody fragment having divalent antigen-binding activity, in which scFv is dimerized. Regarding the divalent antigen-binding activity, this activity may be an activity of binding to either two identical antigens, or two different antigens. The diabody can be produced by obtaining cDNAs encoding the heavy chain variable region and light chain variable region of an antibody, then constructing cDNA expressing scFV, in which the heavy chain variable region is ligated to the light chain variable region using a peptide linker, and then treating the cDNA according to a genetic engineering method.

dsFv is a polypeptide which comprises a heavy chain variable region and a light chain variable region each including a substitution of one amino acid residue with a cysteine residue, in which VH binds to VL via a disulfide bond between the cysteine residues. The amino acid residue to be substituted with the cysteine residue can be selected based on antibody structure prediction according to the method of Reiter et al. or the like. Such dsFv can be produced by obtaining cDNAs encoding the heavy chain variable region and light chain variable region of the antibody and then constructing DNA encoding the dsFv according to a genetic engineering method.

A peptide comprising CDR is constituted such that it comprises at least one region of CDR (CDR1-3) of the heavy chain or light chain. A peptide, which comprises multiple CDR regions, is able to bind to another peptide directly or via a suitable peptide linker. In the case of a peptide comprising CDR, DNA encoding the CDR of the heavy chain or light chain of the antibody is constructed, and it is then inserted into an expression vector. The type of the vector is not particularly limited, and it may be selected, as appropriate, depending on the type of a host cells into which the vector is to be introduced, and the like. The vector is introduced into host cells suitable for the expression of an antibody (e.g. mammalian cells such as CHO cells, yeast cells, insect cells, etc.), so that the peptide can be produced. Alternatively, such a peptide comprising CDR can also be produced by chemical synthesis methods such as an Fmoc method (fluorenylmethyloxycarbonyl method) and a tBoc method (t-butyloxycarbonyl method).

Purification of the Antibody of the Present Invention

A method for purifying the antibody of the present invention is not particularly limited, and a known method can be adopted. For example, a culture supernatant of the above-described hybridoma cells or recombinant cells is recovered, and then, the antibody of the present invention can be purified from the culture supernatant by the combined use of known methods such as various types of chromatography, salting-out, dialysis and membrane separation. When the isotype of an antibody is IgG, the antibody can be simply purified by affinity chromatography using protein A.

Medicament Comprising the Antibody of the Present Invention

The antibody of the present invention or a functional fragment thereof can be used in a medicament comprising, as an active ingredient, the antibody or a functional fragment thereof. The medicament of the present invention can be used to treat or prevent EP4-related immunological diseases, tumor, and pain.

Examples of the EP4-related immunological diseases include: psoriasis; multiple sclerosis; rheumatoid arthritis; systemic lupus erythematosus; inflammatory bowel diseases such as Crohn's disease; type I diabetes and complications thereof (e.g. diabetic retinopathy, diabetic microangiopathy, diabetic nephropathy, macular degeneration, etc.); polymyositis; Sjogren's syndrome; asthma; atopic dermatitis and contact dermatitis; immunodeficiency disorder; and organ transplantation.

The medicament of the present invention can be used to treat or prevent pain, namely, nociceptive pain and neuropathic pain. Examples of the nociceptive pain include: pain caused by activation of somatic and visceral nociceptors, such as pathologic deformation of articulations and chronic arthralgia (e.g. arthritis including rheumatoid arthritis, osteoarthritis, rheumatoid spondylitis, osteoarthritis, gouty arthritis, and juvenile arthritis) (including the alleviation of disease and the maintenance of articular structure); lumbago and neck pain; musculoskeletal pain; myositis; bone fracture; distortion, bruise; pain attended with fibromyalgia syndrome; pain associated with tumor and the treatment thereof; pain attended with influenza or other viral infectious diseases (common cold, etc.); rheumatic fever; visceral pain; pain attended with functional intestinal diseases (e.g. irritable bowel syndrome, non-cardiac chest pain, non-ulcer dyspepsia, etc.); pain attended with myocardial ischemia; dental pain; post-surgical and post-dental-treatment pain; postpartum pain; primary headache disorder (e.g. migraine headache, tension headache, cluster headache, and other primary headache disorders); secondary headache disorder (e.g. headache caused by the head and neck injury, headache caused by vascular disorder of the head and neck, headache caused by non-vascular intracranial diseases, headache caused by substance abuse or substance withdrawal, headache caused by infectious diseases, headache caused by homeostatic disorders, headache or prosopalgia caused by the disorders of the cranium, neck, eye, ear, nose, sinus, tooth, mouse or other face and cranium constitutional tissues, drug induced headache, and pain attended with migraine headache).

Examples of the neuropathic pain include: physical injury or ablation; phantom limb pain; pain caused by chronic inflammatory symptom; postherpetic neuralgia; diabetic neuropathy; nonspecific lumbago; backache; sciatica; neuropathy associated with tumor and the treatment thereof; HIV-related neuropathy; carpal tunnel syndrome; chronic alcoholism; hypothyroidism; trigeminal neuralgia; trigeminal/autonomic headache; uraemia; avitaminosis; multiple sclerosis; fibromyalgia syndrome; and pain attended with toxin.

The medicament of the present invention is effective for the treatment or prevention of tumor. The meaning of the treatment of tumor includes not only the entire or partial inhibition of the growth, diffusion or metastasis of tumor, or the entire or partial elimination of tumor cells, but it also includes the partial or entire resolution of symptoms attended with the tumor (pain, anorexia, weight reduction, etc.).

The treatment or prevention of tumor is directed at the overgrowth of benign tumor and polyp, the overgrowth of malignant tumor and polyp, and neoplasm.

Examples of the overgrowth of benign tumor and polyp include: squamous cell papilloma; basal cell carcinoma; transitional cell papilloma; adenocarcinoma; gastrinoma; cholangiocellular adenoma; hepatocellular adenoma; nephridial adenoma; oncocytoma; glomus tumor; melanocytic nevus; fibroma; myxoma; lipoma; leiomyoma; rhabdomyoma; benign teratoma; angioma; osteoma; chondroma; and meningioma.

Examples of the overgrowth of malignant tumor and polyp include: hepatic cell carcinoma; cholangiocarcinoma; renal cell carcinoma; squamous-cell carcinoma; basal cell carcinoma; transitional cell carcinoma; adenocarcinoma; malignant gastrinoma; malignant melanoma; fibrosarcoma; myxosarcoma; liposarcoma; leiomyosarcoma; rhabdomyosarcoma; malignant teratoma; angiosarcoma; Kaposi's sarcoma; osteosarcoma; chondrosarcoma; lymphangiosarcoma; malignant meningioma; non Hodgkin's lymphoma; Hodgkin's lymphoma; leukemia; and encephaloma.

Examples of the neoplasm include: epithelial cell-derived neoplasm (epithelial carcinoma), basal cell carcinoma, and adenocarcinoma; labial cancer, oral cancer, esophageal cancer, gastrointestinal cancer such as small intestinal cancer and stomach cancer, colon cancer, rectal cancer, liver cancer, bladder cancer, pancreatic cancer, ovarian cancer, cervical cancer, lung cancer, and breast cancer; skin cancer such as squamous-cell carcinoma and basal cell carcinoma, prostatic cancer, and renal cell carcinoma; and known other cancers that affect systemic epithelial, mesenchymal or blood cells.

There can be provided an antibody-drug conjugate which comprises the antibody of the present invention and a compound having antitumor activity and/or cytotoxicity. According to a genetic recombination technique, the protein toxin used as a compound having antitumor activity and/or cytotoxicity is fused with an antibody gene on the gene, so that it can be expressed as a single protein. The thus obtained protein is generally referred to as immunotoxin. Examples of the compound having antitumor activity include doxorubicin and mitomycin C. A method for producing an antibody-drug conjugate is not particularly limited. An example of the method is a method of coupling an antibody with a drug via a disulfide bond or a hydrazone bond.

Pharmaceutical Composition Comprising the Antibody of the Present Invention

The present invention includes a medicament or a pharmaceutical composition. In addition to the above-described antibody of the present invention or a functional fragment thereof, a physiologically acceptable salt thereof may also be used as an active ingredient of the medicament of the present invention. When an acidic group is present, examples of such a salt include: alkaline metal and alkaline earth-metal salts such as lithium, sodium, potassium, magnesium or calcium; amine salts such as ammonia, methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine or L-glucamine; and salts formed with basic amino acids such as lysine, δ-hydroxylysine or arginine. When a basic group is present, examples of such a salt include: salts formed with mineral acids such as hydrochloric acid, hydrobromic acid, sulfuric acid, nitric acid or phosphoric acid; salts formed with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid or salicylic acid; and salts formed with acidic amino acids such as aspartic acid or glutamic acid.

As the medicament of the present invention, the antibody of the present invention or a functional fragment thereof, which is an active ingredient of the medicament, may directly be administered. In general, however, the medicament of the present invention is desirably administered in the form of a pharmaceutical composition comprising one or two or more pharmaceutical additives, as well as the antibody of the present invention or a functional fragment thereof used as an active ingredient. As an active ingredient of the medicament of the present invention, a combination of two or more types of the antibodies of the present invention or functional fragments thereof may be used. Known other agents may also be added to the above-mentioned pharmaceutical composition.

The type of the pharmaceutical composition is not particularly limited. Examples of the dosage form include a tablet, a capsule, a granule, a powder medicine, syrup, a suspension, a suppository, an ointment, a cream, a gel, a patch, an inhalant, and an injection. These pharmaceutical preparations are prepared according to an ordinary method. In the case of a liquid agent, it may adopt a form in which the agent is dissolved or suspended in water or another suitable medium before use. Moreover, in the case of a tablet or a granule, it may be coated according to a well-known method. In the case of an injection, it is prepared by dissolving the compound of the present invention in water. The present compound may also be dissolved in a normal saline or a dextrose solution, as necessary, and a buffer or a preservative may also be added to such a solution. The pharmaceutical composition may be provided in any given pharmaceutical form used for oral or parenteral administration. For example, the pharmaceutical composition may be prepared in the form of a pharmaceutical composition used for oral administration, such as a granule, a parvule, a powder medicine, a hard capsule, a soft capsule, syrup, an emulsion, a suspension or a liquid agent, or it may be prepared in the form of a pharmaceutical composition used for parenteral administration (intravenous administration, intramuscular administration or subcutaneous administration), such as an injection, a drop, a percutaneous absorption agent, a transmucosal absorption agent, a transnasal agent, an inhalant or a suppository. In the case of an injection or a drop, it may be prepared in a powdery form such as a freeze-dried form, and it may be then dissolved in a suitable aqueous medium such as a normal saline before use. Also, a sustained-release preparation coated with a polymer or the like can be directly administered into the brain.

The types of pharmaceutical additives used in the production of the pharmaceutical composition, the ratio of the pharmaceutical additives to the active ingredient, and a method for producing the pharmaceutical composition may be appropriately determined by a person skilled in the art, depending on the form of the pharmaceutical composition to be produced. As such pharmaceutical additives, inorganic or organic substances, or solid or liquid substances can be used. In general, such pharmaceutical additives can be added at a weight percentage of 1% to 90% based on the weight of the active ingredient. Specific examples of such substances used as pharmaceutical additives include lactose, glucose, mannit, dextrin, cyclodextrin, starch, suclose, magnesium aluminometasilicate, synthetic aluminum silicate, carboxymethylcellulose sodium, hydroxypropyl starch, carboxymethylcellulose calcium, ion-exchange resin, methyl cellulose, gelatin, gum Arabic, hydroxypropyl cellulose, hydroxypropylmethyl cellulose, polyvinylpyrrolidone, polyvinyl alcohol, light anhydrous silicic acid, magnesium stearate, talc, tragacanth, bentonite, Veegum, titanium oxide, sorbitan fatty acid ester, sodium lauryl sulfate, glycerin, fatty acid glycerin ester, purified lanolin, glycerinated gelatin, polysorbate, macrogol, vegetable oil, wax, liquid paraffin, white petrolatum, fluorocarbon, non-ionic surfactant, propylene glycol, and water.

In order to produce a solid preparation used for oral administration, the active ingredient is mixed with an excipient ingredient such as lactose, starch, crystalline cellulose, calcium lactate or silicic acid anhydride to prepare a powder medicine. Otherwise, a binder such as saccharose, hydroxypropyl cellulose or polyvinylpyrrolidone, a disintegrator such as carboxymethyl cellulose or carboxymethylcellulose calcium, or other additives are further added to the above obtained mixture, as necessary, and the obtained mixture is then subjected to wet granulation or dry granulation, so as to prepare a granule. In order to produce a tablet, such a powder medicine or a granule may be subjected to a tablet-making operation, directly or with addition of a lubricant such as magnesium stearate or talc. The prepared granule or tablet may be coated with an enteric coating base such as hydroxypropylmethylcellulose phthalate or a methacrylic acid-methyl methacrylate polymer, so as to prepare an enteric coated drug. Otherwise, it may be coated with ethyl cellulose, carnauba wax or hydrogenated oil, so as to prepare a long-acting preparation. Moreover, in order to produce a capsule, a powder medicine or a granule is filled into a hard capsule, or the active ingredient is coated with a gelatin film, directly or after being dissolved in glycerin, polyethylene glycol, sesame oil, olive oil or the like, thereby producing a soft capsule.

In order to produce an injection, the active ingredient, together with a pH adjuster such as hydrochloric acid, sodium hydroxide, lactose, lactic acid, sodium, sodium monohydrogen phosphate or sodium dihydrogen phosphate, and an isotonizing agent such as sodium chloride or glucose, as necessary, is dissolved in a distilled water for injection, and the obtained solution is subjected to aseptic filtration and is then filled into an ampule. Otherwise, mannitol, dextrin, cyclodextrin, gelatin or the like may be further added to the above obtained solution, and the obtained mixture may be then subjected to vacuum freeze-drying, so as to prepare an injection which is dissolved before use. Furthermore, lecithin, polysorbate 80, polyoxyethylene hydrogenated castor oil or the like is added to the active ingredient, and it is emulsified in water, so as to prepare an emulsion for injection.

In order to produce a rectal administration agent, the active ingredient, together with a suppository base such as cacao butter, tri-, di- and mono-glyceride of fatty acid, or polyethylene glycol, is moisturized and melted, and the resultant is then poured into a mold, followed by cooling. Otherwise, the active ingredient may be dissolved in polyethylene glycol or soybean oil or the like, and it may be then coated with a gelatin film or the like.

The dose and administration frequency of the medicament of the present invention are not particularly limited. These factors can be appropriately selected by a doctor's judgment, depending on conditions such as the purpose of preventing and/or treating deterioration and/or progression of a disease to be treated, the type of the disease, the body weight and age of a patient, and the severity of the disease. In general, the dose of the present medicament is approximately 0.01 to 1000 mg (the weight of the active ingredient) per adult per day via oral administration. The medicament can be applied once or divided over several administrations per day, or every several days. When the medicament is used as an injection, it is desirable that the medicament be continuously or intermittently administered at a dose of 0.001 to 400 mg (the weight of the active ingredient) per adult per day.

The medicament of the present invention can be prepared as a sustained-release preparation such as an implantable tablet and a delivery system encapsulated into a microcapsule, using a carrier capable of preventing the sustained-release preparation from immediately being removed from the body. Examples of the carrier that can be used herein include biodegradable and biocompatible polymers, such as ethylene vinyl acetate, polyanhydride, polyglycolic acid, collagen, polyorthoester, and polylactic acid. Such materials can be easily prepared by a person skilled in the art. In addition, a liposome suspension can also be used as a pharmaceutically acceptable carrier. The type of useful liposome is not limited. Such liposome is prepared as a lipid composition comprising phosphatidyl choline, cholesterol and PEG-induced phosphatidylethanol (PEG-PE) by being passed through a filter with a suitable pore size, such that it has a size suitable for use, and it is then purified by a reverse phase evaporation method.

The medicament of the present invention can be prepared as a pharmaceutical composition in the form of a kit, and it can be included in a container or package, together with an instruction manual for administration. When the pharmaceutical composition of the present invention is provided in the form of a kit, different constituents in the composition are wrapped with different containers, and they are then mixed immediately before use. Thus, different constituents are wrapped, separately, because it makes possible to preserve active constituents for a long period of time without losing the functions of the active constituents.

A reagent contained in the kit is supplied into a container made of a material that effectively keeps the activity of the constituents for a long period of time, does not adsorb the constituents on the inner surface thereof, and does not alter the quality of the constituents. For example, a sealed glass ampule may comprise a buffer enclosed in the presence of neutral non-reactive gas such as nitrogen gas. The ampule is constituted with glass, an organic polymer such as polycarbonate or polystyrene, ceramic, metal, or any other suitable materials that are commonly used to retain the reagent.

Moreover, the kit may also comprise an instruction manual. The instruction manual for the present kit may be printed on a paper and/or may be recorded on an electrically or electromagnetically readable medium, such as a floppy (registered trademark) disk, CD-ROM, DVD-ROM, a Zip disk, a videotape or an audiotape, and it may be then provided to a user in such a form. A detailed instruction manual may be actually included with the kit, or it may be published on the website that is designated by a kit manufacturer or distributer or noticed through an e-mail or the like.

Furthermore, the present invention includes a method for preventing or treating EP4-related immunological diseases, tumor and pain, which comprises administering to a patient and the like the medicament or pharmaceutical composition of the present invention.

The term "treat" is used herein to mean inhibition or alleviation of the progression and deterioration of the pathological condition of a mammal affected with a disease that develops due to abnormality in the function of EP4 (e.g. abnormal increase in the function, etc.). Thus, this is a treatment carried out for the purpose of inhibiting or alleviating the progression and deterioration of the above-mentioned disease.

On the other hand, the term "prevent" is used herein to mean previous inhibition of the development of, or affecting with a disease that develops due to abnormality in the function of EP4 (e.g. abnormal increase in the function, etc.) in a mammal that is likely to be affected with the aforementioned disease. Thus, this is a treatment carried out for the purpose of previously inhibiting the development of various symptoms of the disease.

The "mammal" to be treated means any given animal belonging to Mammalia, and the type of the mammal is not particularly limited. Examples of the mammal used herein include humans, pet animals such as a dog, a cat or a rabbit, and livestock animals such as a bovine, a swine, sheep or a horse. The particularly preferred "mammal" is a human.

The Antibody-Immobilized Carrier of the Present Invention

The present invention includes an antibody-immobilized carrier. The antibody-immobilized carrier of the present invention is formed by immobilizing the anti-human EP4 antibody of the present invention on a carrier. In a preferred embodiment, the antibody-immobilized carrier of the present invention is allowed to come into contact with blood containing EP4-expressing cells, so that it can be used to remove the EP4-expressing cells from the body fluid. The anti-human EP4 antibody immobilized on a carrier may be of only one type, or of two or more types.

A specific form of the antibody-immobilized carrier of the present invention is, for example, the antibody of the present invention immobilized on a water-insoluble carrier, which is then filled into a container. Herein, all types of materials can be used as such water-insoluble carriers. In terms of moldability, sterilization and low cytotoxicity, preferred materials include: synthetic polymers such as polyethylene, polypropylene, polystyrene, acrylic resin, nylon, polyester, polycarbonate, polyacrylamide or polyurethane; natural polymers such as agarose, cellulose, cellulose acetate, chitin, chitosan or alginate; inorganic materials such as hydroxyapatite, glass, alumina or titania; and metallic materials such as stainless steel or titanium.

Examples of the form of a carrier include a granular form, a flocculent form, a woven fabric, a non-woven fabric, a spongy porous form, and a platy form. From the viewpoint of a large surface area per volume, a granular form, a flocculent form, a woven fabric, a non-woven fabric, and a spongy porous form are preferable. For example, peripheral blood is supplied through a porous filter in which a container has previously been filled with an antibody-immobilized water-insoluble carrier, so that disease-associated EP4-expressing cells can be efficiently removed.

The antibody-immobilized carrier of the present invention can be combined with other components, so as to produce a kit for removing EP4-expressing cells. Examples of other components include an anticoagulant and an extracorporeal circulation circuit.

Diagnostic Kit Comprising the Anti-EP4 Antibody of the Present Invention

The anti-EP4 antibody of the present invention can be provided in the form of a diagnostic kit. The diagnostic kit of the present invention comprises an antibody, and may also comprise a labeling substance, or a secondary antibody or a labeled substance thereof. The labeled substance of antibody means an antibody labeled with an enzyme, a radioisotope, a fluorescent compound, a chemiluminescent compound, etc. In addition to the aforementioned components, the diagnostic kit of the present invention may comprise other reagents used for carrying out the detection of the present invention, for example, if the labeled substance is an enzyme-labeled substance, the diagnostic kit may also comprise an enzyme substrate (a coloring substrate, etc.), an enzyme substrate solution, an enzyme reaction termination solution, an analyte diluent, and the like. Furthermore, the present diagnostic kit may also comprise various types of buffers, sterilized water, various types of cell culture vessels, various types of reactors (e.g. Eppendorf tube, etc.), a blocking agent (Bovine Serum Albumin (BSA), Skim milk, and serum components such as Goat serum), a washing agent, a surfactant, various types of plates, an antiseptic agent such as sodium azide, an experimental operation manual (instruction manual), and the like. Examples of the measurement method applied herein include ELISA, EI, RIA, fluorescence immunoassay (FIA), luminescence immunoassay, and flow cytometry. Among these methods, flow cytometry is particularly preferable in terms of simplicity and high sensitivity. In addition, the diagnostic kit of the present invention can be used in combination with another antibody kit comprising an antibody that recognizes a cell surface antigen.

The diagnostic kit of the present invention is allowed to react with the blood cells of a patient affected with cancer, autoimmune disease or the like, so that the ratio of EP4-expressing cells in the blood can be detected. By combining the present diagnostic kit with another cell surface antigen antibody, the ratio of EP4-expressing cells in a specific cell population (e.g. dendritic cells, TH17 cells, or Treg cells) can be detected. By evaluating an increase or decrease in the ratio of the EP4-expressing cells, the condition of the disease can be evaluated.

Hereinafter, the present invention will be described more in detail in the following examples. However, these examples are not intended to limit the scope of the present invention.

EXAMPLES (1) Production of Human EP4 Expression Vector pcDNA-DEST40-hEP4

The sequence 5'-GGGGACAAGTTTGTA-CAAAAAAGCAGGCTTCGAAGGAGATAGAAC-CATGGA GACAGACACACTCCTGC-TATGGGTACTGCTGCTCTGGGTTCCAGGTTCCACTG GTGAC-3' (SEQ ID NO: 30) was added to the 5'-terminus of a sequence, which had been prepared by removing a stop codon from the ORF sequence of the human EP4 gene registered in Genbank (Accession No. NM_000958), and the sequence 5'-GACCCAGCTTTCTTGTA-CAAAGTGGTCCCC-3' (SEQ ID NO: 31) was added to the 3'-terminus thereof, thereby synthesizing DNA. Using Gateway System (Invitrogen), the thus synthesized DNA was incorporated into a pDONR221 vector (manufactured by Invitrogen), so as to prepare pDONR-hEP4. The nucleotide sequence of the insert was determined according to an ordinary method, and it was confirmed that the sequence included no errors. Subsequently, using Gateway System, the sequence containing the human EP4 gene was incorporated into the pcDNA-DEST40 vector (manufactured by Invitrogen) to obtain pcDNA-DEST40-hEP4. Human EP4 expressed from this plasmid is a fusion protein in which V5 and 6 x HIS tags were added to the C-terminus. The plasmid DNA of pcDNA-DEST40-hEP4 was prepared by transforming *Escherichia coli* (DH5α) according to an ordinary method and then amplifying it, and then using PureLink HiPure Plasmid Filter Maxiprep Kit (manufactured by Invitrogen) in accordance with an instruction manual included therewith.

(2) Preparation of Human EP4-Expressing 293FT Cells

10 μg of the above-described plasmid DNA of pcDNA-DEST40-hEP4 was introduced into 293FT cells (manufactured by Invitrogen) plated on a 100-mm collagen I coated cell culture dish, using 25 μL of Lipofectamin 2000 (manufactured by Invitrogen) in accordance with an instruction manual included therewith. Twenty-four hours after the gene introduction, the cells were washed with HBSS (Hanks' Balanced Salt Solutions, manufactured by Invitrogen), were then removed from the cell culture dish using an enzyme-free cell dissociation buffer (manufactured by Invitrogen), and were then recovered by centrifugation. The EP4 gene-introduced 293FT cells and the gene-non-introduced 293FT cells were subjected to a cell membrane permeabilization using Cytofix/Cytoperm Kit (manufactured by BD). The resulting cells were mixed with an anti-V5 tag antibody (manufactured by Invitrogen), and the mixture was then incubated (4° C., 1 hour). Thereafter, the resultant was washed with a washing buffer (0.1% fetal bovine serum-containing PBS (Phosphate Buffered Saline, manufactured by Invitrogen)) three times, and was then stained with an Alexa488-labeled anti-mouse IgG antibody (manufactured by Invitrogen) used as a secondary antibody (4° C., 1 hour). Then, the resultant was again washed with a washing buffer three times, and was then analyzed with the flow cytometer Quanta SC MPL (manufactured by BECKMAN COULTER). As a result, since Alexa488 fluorescence positive signal was detected in only the gene-introduced 293FT cells, it could be confirmed that human EP4 was expressed in the cells.

Thus, this human EP4-expressing 293FT cell was used as a sensitizing antigen.

(3) Immunization

Antigen immunization was performed on 7-week-old female 129/Ola background mice. The human EP4-expressing 293FT cells described in (2) above were suspended in a normal saline, and thereafter, the suspension were intraperitoneally administered to the above-mentioned mice 5 times at administration intervals of 10 to 14 days.

(4) Production of Hybridoma

Three days after the 5$^{th}$ immunization, the spleen was removed from each mouse, and splenic cells were prepared. The splenic cells and mouse myeloma P3X63Ag8.653 cells (obtained from ECACC) were subjected to cell fusion according to an ordinary method using Polyethylene Glycol 4000 (manufactured by Merck). The fused cells were suspended in GIT Medium (manufactured by Wako Pure Chemical Industries, Ltd.) that contained 100 units/mL penicillin, 100 μg/mL streptomycin, non-essential amino acid, 2 mM L-glutamine, and NCTC-109 medium (all of which were manufactured by Invitrogen). The obtained suspension was then plated at a density of 100 μL/well on a 96-well plate, and it was then cultured at 37° C. in 5% $CO_2$. From the day following the cell fusion, the medium was exchanged with a medium formed by adding HAT Supplement (manufactured by Invitrogen) to the above-mentioned medium, and the culture was continued for 13 days after completion of the cell fusion. As a result, a colony of hybridomas (approximately 700 clones) was obtained.

(5) Construction of NS0 Cell Line Stably Expressing Human EP4

Using Gateway System, the recombination reaction between the pDONR-hEP4 described in (1) above and the pEF-DEST51 vector (manufactured by Invitrogen) was performed to obtain a plasmid pEF-DEST51-hEP4. Human EP4 expressed by this plasmid is a fusion protein in which V5 and 6× HIS tags were added to the C-terminus.

Using 35 μL of Lipofectamin LTX (manufactured by Invitrogen) and 14 μL of PlusReagent (manufactured by Invitrogen) in accordance with an instruction manual included therewith, 14 μg of the plasmid pEF-DEST51-hEP4 was introduced into $1 \times 10^7$ mouse myeloma NS0 cells (obtained fromCell Bank, RIKEN BioResource Center) that had been cultured in RPMI medium containing 10% fetal bovine serum, 100 units/mL penicillin, and 100 μg/mL streptomycin (manufactured by Invitrogen). From the day following the gene introduction, while the medium was exchanged with RPMI medium supplemented with 2.5 μg/mL antibiotic blasticidin (manufactured by Invitrogen) every 3 days, the culture was continuously carried out for 2 weeks. Blasticidin-resistant NS0 cells were cloned from the formed colonies according to a penicillin cup method.

The obtained blasticidin-resistant NS0 cells were blocked with FcBlock (manufactured by Becton, Dickinson and Company) at 4° C. for 15 minutes, and thereafter, the expression of an EP4 fusion protein was confirmed with the flow cytometer by the same method as described in (2) above. As a result, it could be confirmed that the obtained blasticidin-resistant NS0 cells stably expressed human EP4.

(6) Screening for Anti-EP4 Antibody-Producing Hybridoma

The NS0 cell line stably expressing human EP4 ($2 \times 10^5$ cells) produced in (5) above was stained by the same method as described in (2) above, and was then analyzed with a flow cytometer. A cell membrane permeabilization was not performed, and 50 μL of culture supernatant of the hybridoma obtained in (4) above was used as a primary antibody. As a result, an Alexa488 fluorescence positive reaction was found in supernatants in 21 wells. The cells in the positive well were cloned by limiting dilution. A culture supernatant after completion of the culture for 2 weeks was also subjected to a binding test with the NS0 cell line stably expressing human EP4 with a flow cytometer. The same cloning and binding test were repeated again, and 2 clones of anti-EP4 antibody-producing hybridomas were finally obtained. These hybridomas were named as NBG016-mAb14 and NBG016-mAb21.

The obtained hybridoma cells NBG016-mAb 14 and NBG016-mAb21 were deposited with the International Patent Organism Depositary, the National Institute of Advanced Industrial Science and Technology, an Independent Administrative Institution under the Ministry of Economy, Trade and Industry, at the AIST Tsukuba Central 6, Higashi 1-1-1, Tsukuba, Ibaraki, Japan (postal code: 305-8566), under accession Nos. FERM P-21978 and FERM P-21979, respectively, on Jun. 29, 2010 (the original deposition date). Thereafter, the original deposition was then transferred to an international deposition under the provisions of the Budapest Treaty (the notification date of "Certificate of Receipt of Original Deposition" and "Viabilty Certification": Sep. 5, 2011). Accession Nos. are FERM BP-11402 and FERM BP-11403, respectively.

(7) Purification of Anti-EP4 Antibody

The hybridoma cells NBG016-mAb 14 and NBG016-mAb21 were each continuously cultured in a serum-free CD-Hybridoma Medium (manufactured by Invitrogen), until approximately 90% of cells died, so as to produce antibodies. The cells were removed from 100 mL of the culture supernatant by centrifugation (1,500 rpm, 15 minutes), and the residue was then passed through HiTrap Protein G HP Column (manufactured by GE Healthcare Japan) to purify and concentrate IgG. To determine the subtype of an IgG and the type of a light chain, the thus purified IgG was examined using Iso Strip mouse monoclonal antibody isotyping kit (manufactured by Roche Diagnostics). As a result, they were both (IgG2a, κ). Hereinafter, the terms "NBG016-mAb14" and "NBG016-mAb21" indicate these purified antibodies. When the term "hybridoma" or "cell" is used, such term indicates a hybridoma that produces these antibodies.

As in the case of (2), (3), (4) and (6) above, hybridoma cells producing an anti-EP4 antibody with a different subtype were obtained. From a culture supernatant of this hybridoma, purified IgG, the subtype and light chain type of which were (IgG1, κ), was obtained in the same manner as described in (7) above. This purified antibody was referred to as NBG016-mAb9.

(8) Production of the CHO Cell Line Stably Expressing Human EP4

Using Gateway System, a human EP4 gene from pDONR-hEP4 was incorporated into the pEF5/FRT/V5-DEST vector (manufactured by Invitrogen) to obtain pEF-FRT-hEP4. Human EP4 expressed by this plasmid is a fusion protein in which V5 and 6× HIS tags were added to the C-terminus.

Using Lipofectamin 2000, the plasmids pEF-FRT-hEP4 and pOG44 (manufactured by Invitrogen) were simultaneously introduced into Flp-In-CHO cells (manufactured by Invitrogen) that had been cultured in Ham's F-12 medium (manufactured by Invitrogen) containing 10% fetal bovine serum, 100 units/mL penicillin and 100 μg/mL streptomycin. From the day following the gene introduction, the medium was exchanged with Ham's F-12 medium supplemented with 500 μg/mL antibiotic hygromycin (manufactured by Invitrogen), and while exchanging the medium with a fresh one every 3 days, the cells were cultured for 2 weeks. From the formed colonies, hygromycin-resistant cells were cloned according to a penicillin cup method.

A phycoerythrin (PE)-labeled anti-mouse IgG antibody (BECKMAN COULTER) was used as a secondary antibody, and the binding of the obtained hygromycin-resistant cells to an anti-V5 tag antibody was analyzed with a flow cytometer by the method described in (2) above. As a result, the obtained hygromycin-resistant Flp-In-CHO cells showed the positive signal of PE, and thus, it could be confirmed that the cells stably expressed human EP4. Hereinafter, this cell is referred to as a CHO cell line stably expressing human EP4.

(9) Binding Test of Anti-Human EP4 Antibody and Human EP4-Expressing Cells

The binding test of an anti-human EP4 antibody and a CHO cell line stably expressing human EP4 was carried out with flow cytometry by the method described in (6) above. The CHO cell line stably expressing human EP4 or the parent Flp-In-CHO cell line ($5 \times 10^5$ cells) was used. As a primary antibody, 1 μs of NBG016-mAb14, NBG016-mAb21, or a mouse isotype control antibody (manufactured by BioRegend) was used. As a secondary antibody, a PE-labeled anti-mouse IgG antibody was used.

The results are shown in FIG. 1. The parent Flp-In-CHO cell line is indicated with the histogram filled with grey color, whereas the cells stably expressing human EP4 are indicated with the black solid line. Both NBG016-mAb14 and NBG016-mAb21 bind only to the CHO cell line stably expressing human EP4. Thus, the results demonstrated that these antibodies specifically bind to human EP4.

Likewise, NBG016-mAb9 was also subjected to a binding test with the CHO cell line stably expressing human EP4. The results are shown in FIG. 2. The results demonstrated that NBG016-mAb9 also specifically binds to human EP4.

(10) Inhibition Test Regarding $PGE_2$-Induced cAMP Production by Antibodies

The CHO cell line stably expressing human EP4 or the parent Flp-In-CHO cell line was cultured in a medium containing 1 mM acetylsalicylic acid for 18 hours, and was then recovered from the cell culture dish using a cell dissociation buffer. The recovered cells were then dispensed into CulturPlate-96 (manufactured by PerkinElmer) at a density of 2,500 cells per well. NBG016-mAb14, NBG016-mAb21, or a mouse isotype control antibody was added to each well to a concentration of 0.05 to 30 µg/mL, and it was then left at room temperature for 15 minutes. Subsequently, $PGE_2$ (manufactured by Cayman) was added to each well to a concentration of $5\times10^{-11}$ M, and the obtained mixture was further left at room temperature for 30 minutes.

Using LANCE Ultra cAMP Kit (manufactured by PerkinElmer), a reaction was carried out in accordance with an instruction manual included with the kit. Then, the level of cAMP produced in the cells was measured using the plate reader ARVO 1420 HTS (manufactured by PerkinElmer).

The results are shown in FIG. 3. When the mouse isotype control antibody was added, it did not provide a significant inhibitory effect on $PGE_2$-induced cAMP production level. In contrast, when NBG016-mAb14 or NBG016-mAb21 was added, an inhibitory effect on cAMP production was observed in an antibody concentration-dependent manner. Using the data analysis software OriginPro 8.1 (manufactured by OriginLab), analysis was carried out with logistic function. As a result, the $IC_{50}$ value of NBG016-mAb 14 was found to be 0.15 µg/mL (approximately 1.0 nM), and the $IC_{50}$ value of NBG016-mAb21 was found to be 0.24 µg/mL (approximately 1.6 nM). From these results, it was demonstrated that NBG016-mAb 14 and NBG016-mAb21 were functional antibodies having antagonist activity on human EP4, and that these antibodies have receptor function-inhibiting activity that is equivalent to or greater than that of existing substances (e.g. low-molecular-weight compounds) having antagonist activity on human EP4.

Likewise, NBG016-mAb9 was also subjected to a test involving addition of $1.5\times10^{40}$ M $PGE_2$. The results are shown in FIG. 4. As a result of the above-described analysis, the $IC_{50}$ value of NBG016-mAb9 was found to be 4.6 µg/mL (approximately 28.8 nM). These results demonstrate that NBG016-mAb9 is also a functional antibody having antagonist activity on human EP4.

(11) Production of Expression Vectors for Human EP1-4 and Mouse EP1-4

To the 5'-terminus of a sequence, which had been formed by removing a stop codon from the ORF sequence of each of human EP1 (GenBank Accession No. NM_000955), human EP2 (GenBank Accession No. NM_000956), human EP3al (GenBank Accession No. X83857), mouse EP1 (GenBank Accession No. NM_013641), mouse EP2 (GenBank Accession No. NM_008964), mouse EP3 (GenBank Accession No. NM_011196) and mouse EP4 (GenBank Accession No. NM_008965), the sequence CACCATGGAGACA-GACACACTCCTGC-TATGGGTACTGCTGCTCTGGGTTCCAG GTTC-CACTGGTGAC (SEQ ID NO: 32) was added, so as to prepare a DNA fragment. This DNA fragment was amplified by PCR using KOD FX (manufactured Toyobo Co., Ltd.) according to an ordinary method. The amplified DNA was incorporated into the pENTR/D-TOPO vector (manufactured by Invitrogen), so as to prepare pENTR-hEP1, pENTR-hEP2, pENTR-hEP3, pENTR-mEP1, pENTR-mEP2, pENTR-mEP3, and pENTR-mEP4. The nucleotide sequence of each insert was determined according to an ordinary method, and it was confirmed that the sequences included no errors. Using these 7 types of plasmids and the plasmid pDONR-hEP4 produced in (1) above, individual inserts were incorporated into the pcDNA-DEST47 vector (manufactured by Invitrogen) by Gateway System. As a result, the following plasmids were obtained: pcDNA-DEST47-hEP1, pcDNA-DEST47-hEP2, pcDNA-DEST47-hEP3, pcDNA-DEST47-hEP4, pcDNA-DEST47-mEP1, pcDNA-DEST47-mEP2, pcDNA-DEST47-mEP3, and pcDNA-DEST47-mEP4. These plasmids express a fusion protein in which Cycle 3 Green Fluorescent Protein (GFP) has been added to the C-terminus of each $PGE_2$ receptor.

(12) Binding Specificity Test of Anti-EP4 Antibody

The pcDNA-DEST47-hEP1, pcDNA-DEST47-hEP2, pcDNA-DEST47-hEP3, pcDNA-DEST47-hEP4, pcDNA-DEST47-mEP1, pcDNA-DEST47-mEP2, pcDNA-DEST47-mEP3, and pcDNA-DEST47-mEP4 produced in (11) above (10 µg each) were each introduced into 293FT cells, using Lipofectamin 2000. On the following day, the cells were washed with HBSS, and were then removed from the cell culture dish using an enzyme-free cell dissociation buffer. The cells were then recovered by centrifugation. The thus recovered cells are referred to as 293FT cells transiently expressing EP.

The binding test of the anti-EP4 antibody of the present invention and the 293FT transiently expressing EP cells was carried out with a flow cytometer according to the method described in (6) above. 293FT cells ($5\times10^5$ cells) that transiently expressed each of 8 types of $PGE_2$ receptor subtypes were used. As a primary antibody, 1 µg of the anti-EP4 antibody NBG016-mAb14 or NBG016-mAb21, or a mouse isotype control antibody (manufactured by BioRegend) was used. As a secondary antibody, a PE-labeled anti-mouse IgG antibody was used.

As an example, the results of NBG016-mAb14 are shown in FIG. 5. Cells showing the positive signal of GFP-derived fluorescence were present, and thus, it could be confirmed that each $PGE_2$ receptor was expressed on 239FT cells. However, among the 8 types of cells, those showing positive signal of PE fluorescence were only human EP4-expressing cells. The same results were obtained from NBG016-mAb21. Thus, it was found that the anti-EP4 antibody of the present invention has strong specificity to human EP4. It was demonstrated that the present anti-EP4 antibody has $PGE_2$ receptor subtype-binding specificity that is higher than that of existing substances having antagonist activity on human EP4.

Likewise, the binding specificity of NBG016-mAb9 was examined. The results are shown in FIG. 6. Among the 8 types of cells each expressing any one of the 8 types of $PGE_2$ receptor subtypes, those showing positive signal of PE fluorescence were only human EP4-expressing cells. From these results, it was found that NBG016-mAb9 also has strong specificity to human EP4.

(13) Binding Test of Human Lymphocytes and Anti-EP4 Antibody

Frozen human peripheral blood mononuclear cells (manufactured by Cellular Technology Ltd.) were thawed using CTL-Anti-Aggregate-Wash Supplement (manufactured by Cellular Technology Ltd.) in accordance with an instruction manual included therewith.

The binding test of the anti-EP4 antibody of the present invention to human lymphocytes was carried out with a flow cytometer according to the method described in (6) above. The prepared human peripheral blood mononuclear cells ($9 \times 10^5$ cells) were mixed with 1.5 ps of NBG016-mAb14, NBG016-mAb21 or a mouse isotype control antibody, respectively as a primary antibody, and then mixed with an Alexa488-labeled anti-mouse IgG antibody as a second antibody. When an analysis was carried out using a flow cytometer, a cell population is divided into a lymphocyte subset and a monocyte/macrophage subset based on the dot plots of forward-scattered light and side scattered light, and the Alexa488 fluorescence intensity of the lymphocyte subset was then examined.

The analysis results with a flow cytometer are shown in FIG. 7. The results of the mouse isotype control antibody are shown with the histogram filled with grey color, whereas the results of the anti-EP4 antibody are shown with the black solid line. Since a majority of the human lymphocyte subset showed a positive signal of Alexa488 fluorescence only in the case of the reaction of the human lymphocytes with the anti-EP4 antibody, it was found that the human lymphocytes bound to the anti-EP4 antibody. From these results, it became clear that the anti-EP4 antibody of the present invention has an ability to bind to human endogenous EP4.

Likewise, NBG016-mAb9 was also subjected to a binding confirmation experiment with human lymphocytes. Human peripheral blood mononuclear cells were isolated from human fresh peripheral blood using Lymphoprep (manufactured by AXIS SHIELD) in accordance with an instruction manual included therewith, and thereafter, a CD14-netagive cellular fraction was separated using Anti-Human CD14 Microbeads (manufactured by Miltenyi Biotec) and was used as a human lymphocyte subset. The subsequent binding confirmation experiment was carried out as described above, using a fluorescein isothiocyanate (FITC)-labeled anti-mouse IgG antibody (manufactured by BECKMAN COULTER) as a secondary antibody. As shown in FIG. 8, a majority of the human lymphocytes bound to NBG016-mAb9, and thus, it was found that NBG016-mAb9 could also bind to human endogenous EP4.

(14) Immunostaining of PMA-Stimulated THP1 with Anti-EP4 Antibody

The human monocytic THP1 cell line was plated on a 4-well culture slide (manufactured by Becton, Dickinson and Company) at a density of $1.5 \times 10^5$ cells per well with RPMI medium containing 100 nM PMA (Phorbol 12-myristate 13-acetate, manufactured by Sigma-Aldrich), and it was then cultured for 3 days, so that the cells were differentiated into macrophage-like cells. After the removal of the medium, the cells were washed with PBS three times, and were then immobilized with 200 μL of 1% paraformaldehyde solution (wherein the cells were left at 4° C. for 30 minutes). The cells were washed with PBS three times again. Thereafter, 300 μL of 1% BSA (Bovine Serum Albumin, manufactured by Wako Pure Chemical Industries, Ltd.) that contained 1 mg/mL human gamma globulin (manufactured by Wako Pure Chemical Industries, Ltd.) was added to the resulting cells to block them (wherein the cells were left at rest at room temperature for 20 minutes). Subsequently, the resulting cells were washed with 0.1% Tween 20 (manufactured by MP Bio)-containing PBS (hereinafter referred to as a washing buffer for immunostaining) three times. Thereafter, 200 μL of NBG016-mAb14, NBG016-mAb21 or a mouse isotype control antibody, which had been adjusted to 1 mg/mL, was added to the cells, and the obtained mixture was then incubated at 4° C. for 1 hour. Thereafter, the resultant was washed with a washing buffer for immunostaining three times, and it was then stained with an FITC-labeled anti-mouse IgG antibody used as a secondary antibody (4° C., 1 hour). The slide was washed with a washing buffer for immunostaining three times, and was finally sealed with Propidium Iodide (PI)-containing VECTASHIELD Mounting Medium (manufactured by Vector Laboratories). The prepared slide was observed under a fluorescence microscope.

The fluorescence microscopic images of the immunostained THP1 cells are shown in FIG. 9. The left view is a stained image of the mouse isotype control antibody, wherein only the cell nucleus (grey) stained with PI can be observed in the center. The right view is a stained image of the anti-EP4 antibody, wherein FITC fluorescence (white) is observed in a granular state surrounding the cell nucleus. From these results, it was found that the antibody of the present invention binds to native EP4 on the surface of the cell membrane of the microphage-like cells that have been differentiated from the THP1 cell line by PMA.

(15) Inhibition of Cytokine Suppressive Effect of $PGE_2$ by Anti-EP4 Antibody $PGE_2$ has been known to suppress, via EP4 or EP2, the production of cytokine in microphage by LPS stimulation. Whether or not the antibody of the present invention would be able to recover the suppression of cytokine production by $PGE_2$ via EP4 was examined using PMA-differentiated THP1 that expressed an EP4 receptor. The THP1 cell line was plated on a 48-well cell culture plate at a density of $2.5 \times 10^5$ cells per well with 100 nM PMA-containing RPMI medium. After completion of the culture for 3 days, the medium was exchanged with an RPMI medium containing 3.0 μg/mL NBG016-mAb14, NBG016-mAb21 or a mouse isotype control antibody, and the obtained mixture was then incubated for 30 minutes. Subsequently, $PGE_2$ was added to the resultant at a concentration of 20 nM, and the obtained mixture was further incubated for 30 minutes. Then, LPS was added to the resultant at a concentration of 100 ng/mL, and the obtained mixture was further cultured for 18 hours. Thereafter, a culture supernatant was recovered, and the amount of TNFα in the culture supernatant was measured using TNFα Human DuoSet Kit (manufactured by R & D Systems) in accordance with an instruction manual included therewith.

Meanwhile, 0.5 mL of AlamarBlue (manufactured by MorphoSys) diluted to 10 times its volume with RPMI medium was added to the cells after the recovery of the culture supernatant. The obtained mixture was incubated for 4 hours, and thereafter, fluorescence intensity was measured using Plate Reader ARVO 1420 HTS under conditions consisting of an excitation wavelength of 535 nm and a detection wavelength of 595 nm. Based on the measurement results with this AlamarBlue, the ratio of relative surviving cell counts among individual wells was obtained, and the amount of TNFα produced per surviving cell count ratio was calculated. The degree at which the antibody of the present invention would be able to recover the suppression of cytokine production by $PGE_2$ was calculated based on the following standard. Specifically, the amount of TNFα in a well to which only LPS stimulation was given was defined as a recovery percentage of 100%, and the amount of TNFα in a well to which LPS stimulation and $PGE_2$ were given was defined as a recovery percentage of 0%. Under such conditions, the recovery percentage in a case in which LPS stimulation, $PGE_2$ and the present antibody were given was obtained.

The test results are shown in Table 1. Even if the mouse isotype control antibody was added, no significant change was found in the suppression of TNFα production by PGE$_2$. However, it was found that when NBG016-mAb14 or NBG016-mAb21 was added, TNFα production suppressed by PGE$_2$ was recovered up to approximately 50%. The same results were obtained from two independent tests. From these results, it became clear that NBG016-mAb 14 and NBG016-mAb21 are functional antibodies having antagonist activity on human endogenous EP4.

TABLE 1

| LPS | PGE$_2$ (3.0 μg/mL) | Antibody | TNFα level ± SD (pg/mL) | Recovery rate ± SD (%) |
|---|---|---|---|---|
| | | | Test 1 | |
| − | − | — | 177.1 | |
| + | − | — | 550.0 ± 21.8 | |
| + | + | — | 286.1 ± 16.7 | |
| + | + | NBG016-mAb14 | 423.4 ± 23.9 | 52.0 ± 12.9 |
| + | + | NBG016-mAb21 | 469.1 ± 48.1 | 69.3 ± 18.2 |
| + | + | Isotype control | 276.9 ± 11.1 | −3.9 ± 4.2 |
| | | | Test 2 | |
| − | − | — | 68.2 ± 8.5 | |
| + | − | — | 403.5 ± 37.1 | |
| + | + | — | 166.8 ± 15.7 | |
| + | + | NBG016-mAb14 | 281.5 ± 10.7 | 48.5 ± 4.5 |
| + | + | NBG016-mAb21 | 286.1 ± 19.5 | 50.4 ± 8.3 |
| + | + | Isotype control | 148.9 ± 15.4 | −7.6 ± 5.5 |

(16) Isolation and Analysis of cDNA Encoding Variable Region of Anti-EP4 Antibody Total RNA was extracted from approximately 1×10$^7$ hybridoma cells producing anti-EP4 antibodies (NBG016-mAb 14 and NBG016-mAb21) using Rneasy Mini Kit (manufactured by QIAGEN) in accordance with an instruction manual included with the kit. PCR was carried out according to a 5'-RACE (rapid amplification of cDNA ends) method using a 5'/3' RACE kit, 2$^{nd}$ Generation (manufactured by Roche Diagnostics), so as to amplify the variable region of a heavy chain or a light chain. Primers corresponding to mouse constant regions γ1 and κ were used as 3' primers. That is, the 3' primers used for amplifying the heavy chain variable region were 5'-AGGGGCCAGTGGATA-GACCGATG-3' (SEQ ID NO: 33) and 5'-GGCTGTTGTTTTGGCTGCAGAGAC-3' (SEQ ID NO: 34). On the other hand, the 3' primers used for amplifying the light chain variable region were 5'-ACTGGATGGTGG-GAAGATGGATAC-3' (SEQ ID NO: 35) and 5'-TGGATA-CAGTTGGTGCAGCATCAG-3' (SEQ ID NO: 36). Subsequently, each of the obtained amplified fragments was electrophoresed on agarose gel, and a band was then excised. DNA was purified by melting the gel. The purified DNA was incorporated into T-Vector pMD20 (manufactured by Takara Bio Inc.). Thereafter, the nucleotide sequence was analyzed, and its amino acid sequence was then determined. The sequence reaction was carried out using ABI Prism BigDye Terminator Cycle Sequencing Ready Reaction Kits Version 3.1 (Applied Biosystems), and the nucleotide sequence was determined using Applied Biosystems 3130×1 Genetic Analyzer (Applied Biosystems). As a result of the analysis of the nucleotide sequence, the nucleic acid sequence encoding the heavy chain variable region of NBG016-mAb 14 was as shown in SEQ ID NO: 1, and the nucleic acid sequence encoding the light chain variable region thereof was as shown in SEQ ID NO: 3. Moreover, the amino acid sequence of the heavy chain variable region thereof was as shown in SEQ ID NO: 2, and the amino acid sequence of the light chain variable region thereof was as shown in SEQ ID NO: 4.

Furthermore, the nucleic acid sequence encoding the heavy chain variable region of NBG016-mAb21 was as shown in SEQ ID NO: 11, and the nucleic acid sequence encoding the light chain variable region thereof was as shown in SEQ ID NO: 13. Moreover, the amino acid sequence of the heavy chain variable region thereof was as shown in SEQ ID NO: 12, and the amino acid sequence of the light chain variable region thereof was as shown in SEQ ID NO: 14.

From the above-described results, the amino acid sequences of CDR regions defined by Kabat et al. ((1991) Sequences of Proteins of Immunological Interest, Fifth edition, U. S. Department of Health and Human Services, U.S. Government Printing Office) were clarified.

The heavy chain CDR1-3 sequences of NBG016-mAb14 were SEQ ID NOS: 5 to 7, respectively. The light chain CDR1-3 sequences thereof were SEQ ID NOS: 8 to 10, respectively. In addition, the heavy chain CDR1-3 sequences of NBG016-mAb21 were SEQ ID NOS: 15 to 17, respectively. The light chain CDR1-3 sequences thereof were SEQ ID NOS: 18 to 20, respectively. The heavy chain CDR sequences of both clones were completely identical to each other.

Regarding NBG016-mAb9 as well, according to the above-described method, the heavy chain variable region was amplified using the primers shown in SEQ ID NO: 33 and SEQ ID NO: 34, and the light chain variable region was amplified using the primers shown in SEQ ID NO: 35 and SEQ ID NO: 36. Then, the sequences of variable regions were determined. The nucleic acid sequence encoding the heavy chain variable region of NBG016-mAb9 was as shown in SEQ ID NO: 41, and the nucleic acid sequence encoding the light chain variable region thereof was as shown in SEQ ID NO: 42. In addition, the amino acid sequence of the heavy chain variable region was as shown in SEQ ID NO: 43, and the amino acid sequence of the light chain variable region thereof was as shown in SEQ ID NO: 44.

The heavy chain CDR1-3 sequences of NBG016-mAb9 were SEQ ID NOS: 45 to 47, respectively. The light chain CDR1-3 sequences thereof were SEQ ID NOS: 48 to 50, respectively.

(17) Cloning of Anti-EP4 Antibody Gene

Using Oligo-dT Primer included with First Strand cDNA Synthesis Kit For RT-PCR (AMV) (manufactured by Roche Diagnostics), cDNA was synthesized in accordance with an instruction manual included therewith. Using the synthesized cDNA as a template, the full-length heavy chain and light chain genes of the anti-EP4 antibody of the present invention were amplified by PCR. The 5'-terminal sides of the heavy chain and light chain were designed using the nucleotide sequence determined by 5'-RACE as a reference, whereas the 3'-terminal sides thereof were designed using a constant region-specific sequence as a reference. The 5' primer used for amplifying the heavy chain gene was 5'-CACTGACCCTACGCGTATGGAATGGAGATG-GATCTTTCTCTTC-3' (SEQ ID NO: 37), and the 3' primer therefor was 5'-ATAAGAATGCGGCCGCTCATT-TACCAGGAGAGTGGGAGAG-3' (SEQ ID NO: 38). The 5' primers used for amplifying the light chain variable region were 5'-TTGCAGCCAGGAACGCGTATGGACAT-GAGGACCCCTGCT-3' (SEQ ID NO: 39) and 5'-ATAAGAATGCGGCCGCTTAACACTCATTCCTGTT-GAAGCT-3' (SEQ ID NO: 40). The obtained heavy chain and light chain amplification fragments were cleaved with the restriction enzymes MluI and NotI. Then, the heavy chain was inserted into pEHX1.1 (manufactured by Toyobo Co., Ltd.), and the light chain was inserted into the MluI-NotI site of pELX2.1 (manufactured by Toyobo Co., Ltd.). Thereafter, their nucleotide sequences were analyzed, and the amino acid sequences thereof were then determined.

As a result of the analysis of the nucleotide sequences, the nucleic acid sequence encoding the heavy chain of NBG016-mAb14 was as shown in SEQ ID NO: 22, and the nucleic acid sequence encoding the light chain thereof was as shown in SEQ ID NO: 24. Moreover, the amino acid sequence of the heavy chain thereof was as shown in SEQ ID NO: 23, and the amino acid sequence of the light chain thereof was as shown in SEQ ID NO: 25.

Furthermore, the nucleic acid sequence encoding the heavy chain of NBG016-mAb21 was as shown in SEQ ID NO: 26, and the nucleic acid sequence encoding the light chain thereof was as shown in SEQ ID NO: 28. Moreover, the amino acid sequence of the heavy chain thereof was as shown in SEQ ID NO: 27, and the amino acid sequence of the light chain thereof was as shown in SEQ ID NO: 29.

The amino acid sequences of the heavy chain and light chain variable regions were identical to the amino acid sequences analyzed by the above-described 5'-RACE method.

Regarding NBG016-mAb9 as well, cDNA was synthesized according to the above-described method, and using the synthesized cDNA as a template, the full-length heavy chain and light chain genes of NBG016-mAb9 were amplified by PCR. The 5' primer used for amplifying the heavy chain gene was 5'-CACTAGAGCCCCCAT-ACGCGTATGGCTGTCCTGGTGCTGTTCC-3' (SEQ ID NO: 51), and the 3' primer therefor was 5'-ATAAGAATGCGGCCGCTCATTTACCCG-GAGAGTGGGAGAG-3' (SEQ ID NO: 52). The 5' primers used for amplifying the light chain gene were 5'-TCCTCAGGTTGCCTCACGCGTAT-GAAGTTGCCTGTTAG-3' (SEQ ID NO: 53) and 5'-ATAAGAATGCGGCCGCTTAACACTCATTCCTGTT-GAAGCT-3' (SEQ ID NO: 40). The obtained heavy chain and light chain amplification fragments were cleaved with the restriction enzymes MluI and NotI. Then, the heavy chain was inserted into pEHX1.1 (manufactured by Toyobo Co., Ltd.), and the light chain was inserted into the MluI-NotI site of pELX2.1 (manufactured by Toyobo Co., Ltd.). Thereafter, their nucleotide sequences were analyzed, and the amino acid sequences thereof were then determined.

The nucleic acid sequence encoding the heavy chain of NBG016-mAb9 was as shown in SEQ ID NO: 54, and the nucleic acid sequence encoding the light chain thereof was as shown in SEQ ID NO: 55. In addition, the amino acid sequence of the heavy chain thereof was as shown in SEQ ID NO: 56, and the amino acid sequence of the light chain thereof was as shown in SEQ ID NO: 57.

(18) Confirmation of Whether the Obtained Antibody Gene Sequences Would Encode Anti-EP4 Antibody Recombinant antibodies of NBG016-mAb 14 and NBG016-mAb21 were produced using Mammalian Power-Express System (manufactured by Toyobo Co., Ltd.). That is, pELX2.1 into which the light chain gene had been inserted was cleaved with the restriction enzymes EcoRI and BglII, and was then electrophoresed on agarose gel to purify a fragment comprising the light chain gene. The purified light chain gene fragment was inserted into the EcoRI-BglII site of pEHX1.1 into which the heavy chain gene had been inserted, so as to produce a plasmid having the genes of both the light chain and the heavy chain. This plasmid was introduced into 293FT cells using Lipofectamin 2000, so that the cells transiently expressed the antibody.

Seventy-two hours after completion of the transduction, a cell culture supernatant was collected, and it was then subjected to a binding test with the CHO cell line stably expressing human EP4 with flow cytometry according to the method described in (6) above. As a control, a culture supernatant of antibody gene-non-introduced 293FT cells was used. As a result, the recombinant antibodies NBG016-mAb 14 and NBG016-mAb21 secreted into such a culture supernatant maintained an ability to bind to human EP4. From these results, it could be confirmed that the antibody gene sequences obtained in (17) above encode the anti-EP4 antibody.

A recombinant antibody of NBG016-mAb9 was also produced by the above-described method. That is, pELX2.1 into which the light chain gene had been inserted was cleaved with the restriction enzymes SalI and SpeI, and was then electrophoresed on agarose gel to purify a fragment comprising the light chain gene. The purified light chain gene fragment was inserted into the SalI-SpeI site of pEHX1.1 into which the heavy chain gene had been inserted, so as to produce a plasmid having the genes of both the light chain and the heavy chain. This plasmid was introduced into 293FT cells, so that the cells transiently expressed the antibody.

Seventy-two hours after completion of the transduction, a cell culture supernatant was collected, and it was then subjected to a binding test with the CHO cell line stably expressing human EP4 with flow cytometry according to the method described in (6) above. As a control, a culture supernatant of antibody gene-non-introduced 293FT cells was used. The results are shown in FIG. 10. In FIG. 10, the parent Flp-In-CHO cell line is indicated with the histogram filled with grey color, whereas the CHO cell line stably expressing human EP4 is indicated with the black solid line. Since the recombinant antibody NBG016-mAb9 secreted into the culture supernatant maintained an ability to bind to human EP4, it could be confirmed that the antibody gene sequences of NBG016-mAb9 obtained in (17) above encode the anti-EP4 antibody.

(19) Production of Recombinant Anti-EP4 Antibody Stably Expressing CHO Cells

A vector comprising the light chain and heavy chain genes of each of NBG016-mAb 14 and NBG016-mAb21 produced in (18) above was cleaved with the restriction enzyme SspI, and was then purified by ethanol precipitation. Using Lipofectamin 2000, the resultant was transduced into CHO-K1 cells (Cell Bank, RIKEN BioResource Center), and the obtained cells were then cultured in Ham's F12 medium containing 10% fetal bovine serum for 24 hours. Twenty-four hours later, the aforementioned medium was exchanged with another Ham's F12 medium containing 10% fetal bovine serum and 10 µg/mL puromycin, and then, the cells were cultured for 12 days, while exchanging the medium with a fresh one every 3 days. Twelve days later, a colony was separated by a penicillin cup method.

The separated CHO-K1 cells were plated on a 24-well plate, and were then cultured in Ham's F12 medium containing 10 µg/mL puromycin for 3 days. Three days later, the medium was exchanged with another Ham's F12 medium containing 10 µg/mL puromycin (to which fetal bovine serum had not been added), and the culture was further carried out for 72 hours. Thereafter, a culture supernatant was recovered.

Mouse IgG in the culture supernatant was detected by ELISA. A series of culture supernatant dilutions were prepared using PBS, were then dispensed into Maxisorp 96-well plate (manufactured by Nunc), and were then left at 4° C. overnight. On the following day, 3% BSA (manufactured by Sigma)-containing PBS was added to the culture, and the obtained mixture was then left at room temperature for 1 hour for blocking. The resultant was washed with 0.1% Tween 20-containing PBS, and a horse radish peroxidase (HRP)-labeled anti-mouse IgG antibody (manufactured by Millipore) diluted to 4,000 times with 1% BSA-containing PBS was then added to the resultant. The obtained mixture was left at room temperature for 1 hour. Thereafter, the reaction product was washed with 0.1% Tween 20-containing PBS, and 100 µL of coloring reagent (Sureblue TMB microwell peroxidase substrate, manufactured by Kirkegaard & Perry Laboratories) was then added thereto. The obtained mixture was left at room temperature for 5 minutes, and 100 µL of 1 N sulfuric acid was added to the mixture to terminate the reaction. Then, the absorbance at 450 nm was measured. As a result, the expression of IgG was confirmed in a culture supernatant of CHO-K1 cells established by introduction of a vector comprising the light chain and heavy chain genes.

(20) Binding Test of Recombinant Anti-EP4 Antibodies and CHO Cell Line Stably Expressing Human EP4

The recombinant antibody NBG016-mAb 14 and the recombinant antibody NBG016-mAb21 were purified from a culture supernatant of the cell line established in (19) above in the same manner as in (7) above. A binding test of each of the obtained purified recombinant anti-EP4 antibodies and the CHO cell line stably expressing human EP4 was carried out with a flow cytometer by the method described in (6) above. The purified recombinant anti-EP4 antibody or mouse isotype control antibody was used in an amount of 1 µg per $5 \times 10^5$ cells. As a secondary antibody, a PE-labeled anti-mouse IgG antibody was used.

The results are shown in FIG. 11. The parent Flp-In-CHO cell line is indicated with the histogram filled with grey color, whereas the CHO cell line stably expressing EP4 is indicated with the black solid line. Both the recombinant antibody NBG016-mAb 14 and the recombinant antibody NBG016-mAb21 bound only to the CHO cell line stably expressing human EP4 stably expressing. As a result, it was confirmed that the purified recombinant anti-EP4 antibodies maintained an ability to bind to human EP4.

(21) Expression Vector for Mouse IgG1 Antibody NBG016-mAb21

The subclass of the NBG016-mAb21 purified in (7) above was IgG2a. Thus, the subclass of the NBG016-mAb21 was modified to be IgG1 so as to produce the mouse IgG1 antibody NBG016-mAb21. The mouse IgG1 antibody NBG016-mAb21 gene was produced as follows by Overlapping PCR. Using the heavy chain gene of NBG016-mAb21 as a template, and also using 5'-CACTGACCC-TACGCGTATGGAATGGAGATGGATCTTTCTCTTC-3' (SEQ ID NO: 37) and 5'-GACAGATGGGGGTGTCGTTT-TAGCGCTAGAGACAGTGACCAGAGTCCC-3' (SEQ ID NO: 58), the variable region gene of NBG016-mAb21 was amplified by PCR. At the same time, using cDNA synthesized from the total RNA of a hybridoma producing mouse IgG1 as a template, and also using 5'-GGGACTCTGGT-CACTGTCTCTAGCGCTAAAACGACACCCC-CATCTGTC-3' (SEQ ID NO: 59) and 5'-ATAAGAATGCGGCCGCTCATTTACCAG-GAGAGTGGGAGAG-3' (SEQ ID NO: 38), a mouse IgG1 portion ranging from CH1 to the constant region gene was amplified by PCR. The thus amplified heavy chain variable region gene was mixed with the amplified CH1-constant region gene fragment, and the obtained mixture was then amplified by PCR using the primers of SEQ ID NO: 37 and SEQ ID NO: 38. The thus amplified DNA fragment was cleaved with the restriction enzymes MluI and NotI, and the cleaved fragment was then inserted into the MluI-NotI site of the expression vector pEHX1.1. The obtained expression vector was cleaved with the restriction enzymes EcoRI and BglII, and a light chain gene fragment (EcoRI-BglII fragment) of NBG016-mAb21 was then inserted therein, so as to produce an expression vector for the mouse IgG1 antibody NBG 016-mAb2.

(22) Method for Producing Cell Line Stably Expressing Mouse IgG1 Antibody NBG016-mAb21

Floating CHO-K1 cells (manufactured by Toyobo Co., Ltd.) ($2.5 \times 10^5$ cells/m1) cultured in 8 mM glutamine-containing EX-CELL CD CHO medium (manufactured by SAFC Bioscience) were dispensed in an amount of 1 ml into each of two wells of a 24-well plate. Thereafter, 136 µl of Opti-MEM, 15 µl of Lipofectamin 2000, and 4 µg of expression vector for mouse IgG1 antibody NBG016-mAb21 cleaved with the restriction enzyme SspI were blended, and the obtained mixture was left at room temperature for 20 minutes. Subsequently, the reaction product was added in an amount of 68 µl each to the wells containing CHO-K1, and the obtained mixture was then incubated in a $CO_2$ incubator for 24 hours. Twenty-hour hours later, the cells were suspended in 8 ml of EX-CELL CD CHO medium containing 8 mM glutamine, and the obtained suspension was dispensed in an amount of 4 ml into each of two wells of a 6-well plate. Then, 3 µl of 10 mg/ml puromycin was added to one well, and 4 µl of 10 mg/ml puromycin was added to the other well. While exchanging the medium with a fresh one every 3 or 4 days, the cells were cultured for 18 days. Thereafter, proliferating cells were recovered from the well, and the recovered cells were then suspended in Conditioned medium (a medium containing per ml: 700 ml of EX-CELL CD CHO medium, 300 ml of culture supernatant of floating CHO-K1 cells, and 1 ml or 0.75 ml of 10 mg/ml puromycin). The obtained suspension was dispensed in an amount of 200 µl into each well of a 96-well plate. One week later, 100 µl of Conditioned medium was added, and the obtained mixture was further culture for 1 week. Thereafter, the cells were subcultured several times, and 500 µl of drug-resistant cells ($4 \times 10^4$ cells/ml) were then added to a 24-well plate, followed by culture for 5 days. Five days later, the amount of the antibody in the culture supernatant was quantified using Mouse IgG EIA Kit (manufactured by Takara Bio Inc.), and antibody-producing cells were then screened. The thus obtained cells were defined as a CHO cell line stably expressing mouse IgG1 antibody NBG016-mAb21.

(23) Purification of Mouse IgG1 Antibody NBG016-mAb21

The CHO cell line stably expressing mouse IgG1 antibody NBG016-mAb21 was cultured in EX-CELL CD CHO medium containing 8 mM glutamine and 7.5 µg/ml puromycin for 10 days, so as to allow it to produce antibody. From 200 mL of this culture supernatant, purified IgG was obtained in the same manner as described in (7) above. Hereinafter, the obtained purified IgG was referred to as mouse IgG1 antibody NBG016-mAb21.

(24) Binding Test of Mouse IgG1 Antibody NBG016-mAb21 and Human EP4

A binding test of the mouse IgG1 antibody NBG016-mAb21 to the CHO cell line stably expressing human EP4 was carried out in the same manner as described in (9) above. The results are shown in FIG. 12(A). The parent Flp-In-CHO cell line is indicated with the histogram filled with grey color, whereas the CHO cell line stably expressing human EP4 is indicated with the black solid line. The mouse IgG1 antibody NBG016-mAb21 bound only to the human EP4 stably expressing CHO cell line stably expressing human EP4. As a result, it was confirmed that the produced mouse IgG1 antibody NBG016-mAb21 maintained an ability to bind to human EP4.

(25) Inhibitory Test Regarding $PGE_2$-Induced cAMP Production by Mouse IgG1 Antibody NBG016-mAb21

Whether or not $PGE_2$-induced cAMP production would be inhibited by the mouse IgG1 antibody NBG016-mAb21 was examined in the same manner as described in (10) above. The cells were allowed to react with the antibody at room temperature for 15 minutes, and $PGE_2$ was then added to the reaction mixture at a concentration of $1.5 \times 10^{10}$ M. The thus obtained mixture was further left at room temperature for 30 minutes. Using LANCE Ultra cAMP Kit (manufactured by PerkinElmer), and a reaction was carried out in accordance with an instruction manual included with the kit, so as to measure the level of cAMP.

The results are shown in FIG. 12(B). When a mouse isotype control antibody was added, it did not provide a significant inhibitory effect on $PGE_2$-induced cAMP production level. In contrast, when the mouse IgG1 antibody NBG016-mAb21 was added, a cAMP production inhibitory effect was observed in an antibody concentration-dependent manner. The $IC_{50}$ value was found to be 1.1 µg/mL (approximately 6.9 nM). From these results, it was demonstrated that even if NBG016-mAb21 is modified to a mouse IgG1 antibody, it could maintain antagonist activity on EP4.

(26) Production of Human Chimeric Antibodies NBG016-mAb14 and NBG016-mAb21

Using Mammalian PowerExpress System (manufactured by Toyobo Co., Ltd.), human chimeric antibodies in which the CH1 region and constant region of NBG016-mAb14 or NBG016-mAb21 were substituted with those of a human antibody gene. The heavy chain variable region gene of each of NBG016-mAb 14 and NBG016-mAb21 was amplified by PCR using 5'-CACTGACCCTAAGCTTATGGAATG-GAGATGGATCTTTCTCTTC-3' (SEQ ID NO: 60) and 5'-GGCTGTTGTGCTAGCTGCAGA-GACAGTGACCAGAGT-3' (SEQ ID NO: 61). The obtained heavy chain gene fragment was cleaved with the restriction enzymes HindIII and NheI, and the cleaved fragment was then inserted into the HindIII-NheI site of the expression vector pEHγX1.1. At the same time, the light chain variable region gene of each of NBG016-mAb 14 and NBG016-mAb21 was amplified by PCR using 5'-AT-TGCAGCCAGGAGAATTCATGGACAT-GAGGACCCCTGCT-3' (SEQ ID NO: 62) and 5'-GGTGCAGCATCCGTACGTTTTATTTC-CAACTTTGTCCCC-3' (SEQ ID NO: 63). The obtained light chain gene fragment was cleaved with the restriction enzymes BsiWI and EcoRI, and the cleaved fragment was then inserted into the BsiWI-EcoRI site of the expression vector pELκX2.1.

The light chain gene-inserted pELκ2.1 was cleaved with the restriction enzymes BglII, NotI and ScaI, and the cleaved fragment was then electrophoresed on agarose gel, so as to purify a fragment containing the light chain gene. The purified light chain gene fragment was incorporated into the BglII-NotI site of pEHγX1.1, into which the heavy chain gene had been inserted, thereby producing a plasmid that maintained the genes of both the light chain and the heavy chain. Using Lipofectamin 2000, this plasmid was introduced into 293FT cells, so that the cells transiently expressed the antibody.

Seventy-two hours after completion of the introduction, a cell culture supernatant was collected, and it was then subjected to a binding test with the CHO cell line stably expressing human EP4 with flow cytometry according to the method described in (6) above. As a control, a culture supernatant of antibody gene-non-introduced 293FT cells was used. As a secondary antibody, a PE-labeled anti-human IgG antibody (manufactured by Abcam) was used. The results are shown in FIG. 13. In FIG. 13, the parent Flp-In-CHO cell line is indicated with the histogram filled with grey color, whereas the CHO cell line stably expressing human EP4 is indicated with the black solid line. From the results shown in the figure, it could be confirmed that the human chimeric antibodies NBG016-mAb 14 and NBG016-mAb21 secreted into the culture supernatant each maintained an ability to bind to human EP4.

These results demonstrated that the nucleic acid sequence encoding the antibody provided by the present invention can be used to produce a recombinant antibody (e.g. a chimeric antibody, a humanized antibody, a human antibody, etc.) that maintains the function of the antibody of the present invention.

INDUSTRIAL APPLICABILITY

Since the antibody provided by the present invention specifically suppresses the function of a human $PGE_2$ receptor subtype EP4, the present antibody is anticipated to play an important role in providing a method for preventing or treating EP4-related diseases or in the development of a preventive or therapeutic agent for the aforementioned diseases.

SEQUENCE LISTING

TPC0033NBK-seq.ST25.txt

What is claimed is:

1. A monoclonal antibody or an antigen-binding fragment thereof, comprising:

heavy chain CDR1 comprising the amino acid sequence shown in SEQ ID NO: 45, heavy chain CDR2 comprising the amino acid sequence shown in SEQ ID NO: 46, heavy chain CDR3 comprising the amino acid sequence shown in SEQ ID NO: 47, light chain CDR1 comprising the amino acid sequence shown in SEQ ID NO: 48, light chain CDR2 comprising the amino acid sequence shown in SEQ ID NO: 49, and light chain CDR3 comprising the amino acid sequence shown in SEQ ID NO: 50;

wherein the antibody or antigen-binding fragment specifically binds to the extracellular domain of EP4, inhibits the function of EP4, and binds to neither EP1, EP2 nor EP3.

2. The monoclonal antibody or antigen-binding fragment thereof according to claim 1, wherein the antibody or antigen-binding fragment comprises:

a heavy chain variable region comprising the amino acid sequence shown in SEQ ID NO: 43, and a light chain variable region comprising the amino acid sequence shown in SEQ ID NO: 44;

wherein the antibody or antigen-binding fragment specifically binds to the extracellular domain of EP4, inhibits the function of EP4, and binds to neither EP1, EP2 nor EP3.

3. The monoclonal antibody or antigen-binding fragment thereof according to claim 1, wherein the antibody is a humanized antibody or a chimeric antibody.

4. The monoclonal antibody or antigen-binding antibody-binding fragment thereof according to claim 1, wherein the antigen-binding fragment is Fab, Fab', F(ab')2, Fv, scFv, a dimer of scFv or dsFv.

5. A pharmaceutical composition, comprising:

the monoclonal antibody or antigen-binding fragment thereof according to claim 1, or a physiologically acceptable salt thereof, and a pharmaceutically acceptable additive.

6. An antibody-immobilized carrier, comprising: a carrier, and the monoclonal antibody or antigen-binding fragment thereof according to claim 1, wherein the antibody or antigen-binding fragment thereof is immobilized on the carrier.

7. A kit for measuring the expression level of EP4 on a cell surface, comprising:
  the monoclonal antibody or antigen-binding fragment thereof according to claim 1, and a container or package.

8. The monoclonal antibody or antigen-binding fragment thereof according to claim 3, wherein the antigen-binding fragment is Fab, Fab', F(ab')2, Fv, scFv, a dimer of scFv or dsFv.

9. A pharmaceutical composition, comprising:
  the monoclonal antibody or antigen-binding fragment thereof according to claim 3, or physiologically acceptable salt thereof, and
  a pharmaceutically acceptable additive.

* * * * *